US007700274B2

(12) United States Patent
Morris et al.

(10) Patent No.: US 7,700,274 B2

(45) Date of Patent: Apr. 20, 2010

(54) COMPOSITIONS AND METHODS IN CANCER ASSOCIATED WITH ALTERED EXPRESSION OF KCNJ9

(75) Inventors: David W. Morris, Davis, CA (US); Eric K. Engelhard, Davis, CA (US)

(73) Assignee: Sagres Discovery, Inc., Emeryville, CA (US)

( * ) Notice: Subject to any disclaimer, the term of this patent is extended or adjusted under 35 U.S.C. 154(b) by 1141 days.

(21) Appl. No.: 10/105,871

(22) Filed: Mar. 20, 2002

(65) Prior Publication Data

US 2006/0121454 A1 Jun. 8, 2006

Related U.S. Application Data

(63) Continuation-in-part of application No. 10/034,650, filed on Dec. 20, 2001, now abandoned, and a continuation-in-part of application No. 09/798,586, filed on Mar. 2, 2001, now abandoned, and a continuation-in-part of application No. 09/747,377, filed on Dec. 22, 2000, now abandoned.

(51) Int. Cl.
*C12Q 1/68* (2006.01)

(52) U.S. Cl. .......................................................... 435/6

(58) Field of Classification Search ..................... 435/6, 435/7.23, 69.1, 183, 320.1, 325; 536/23.1, 536/23.2, 24.31, 24.3
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,469,863 | A | 9/1984 | Ts'o et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,816,567 | A | 3/1989 | Cabilly et al. |
| 5,034,506 | A | 7/1991 | Summerton et al. |
| 5,124,246 | A | 6/1992 | Urdea et al. |
| 5,216,141 | A | 6/1993 | Benner |
| 5,235,033 | A | 8/1993 | Summerton et al. |
| 5,359,100 | A | 10/1994 | Urdea et al. |
| 5,386,023 | A | 1/1995 | Sanghvi et al. |
| 5,445,934 | A | 8/1995 | Fodor et al. |
| 5,545,730 | A | 8/1996 | Urdea et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,571,670 | A | 11/1996 | Urdea et al. |
| 5,580,731 | A | 12/1996 | Chang et al. |
| 5,591,584 | A | 1/1997 | Chang et al. |
| 5,594,117 | A | 1/1997 | Urdea et al. |
| 5,594,118 | A | 1/1997 | Urdea et al. |
| 5,597,909 | A | 1/1997 | Urdea et al. |
| 5,602,240 | A | 2/1997 | De Mesmaeker et al. |
| 5,624,802 | A | 4/1997 | Urdea et al. |
| 5,625,126 | A | 4/1997 | Lonberg et al. |
| 5,633,425 | A | 5/1997 | Lonberg et al. |
| 5,635,352 | A | 6/1997 | Urdea et al. |
| 5,637,684 | A | 6/1997 | Cook et al. |
| 5,644,048 | A | 7/1997 | Yau |
| 5,661,016 | A | 8/1997 | Lonberg et al. |
| 5,681,697 | A | 10/1997 | Urdea et al. |
| 5,681,702 | A | 10/1997 | Collins et al. |
| 5,700,637 | A | 12/1997 | Southern |
| 5,759,776 | A | 6/1998 | Smith et al. |
| 5,776,683 | A | 7/1998 | Smith et al. |
| 5,928,870 | A | 7/1999 | Lapidus et al. |
| 6,074,825 | A | 6/2000 | Rundell et al. |
| 6,153,441 | A | 11/2000 | Appelbaum et al. |
| 6,812,339 | B1 * | 11/2004 | Venter et al. ............. 536/24.31 |

FOREIGN PATENT DOCUMENTS

| | | |
|---|---|---|
| WO | WO 87/05330 | 9/1987 |
| WO | WO 90/10448 | 9/1990 |
| WO | WO 91/04753 | 4/1991 |
| WO | WO 93/22443 | 11/1993 |
| WO | WO 95/25116 | 9/1995 |
| WO | WO 95/35505 | 12/1995 |
| WO | WO 97/27212 | 7/1997 |
| WO | WO 97/27213 | 7/1997 |
| WO | WO 01/94629 | 12/2001 |
| WO | WO0201950 | 1/2002 |
| WO | WO 02/22660 | 3/2002 |
| WO | WO 02/079434 | 10/2002 |
| WO | WO02079434 | 10/2002 |
| WO | WO 03/008583 | 1/2003 |
| WO | WO03008583 | 1/2003 |
| WO | WO 03/057146 | 7/2003 |
| WO | WO 03/057146 A2 * | 7/2003 |
| WO | WO03053224 | 7/2003 |
| WO | WO03057146 | 7/2003 |

OTHER PUBLICATIONS

Bowie et al. (1990), Science 247:1306-1310.*
Wells (1990), Biochemistry 29: 8509-8517.*
Yap et al (BMC Cancer Oct. 7, 2004:242).*
Pennica et al. 1998, PNAS USA 95:14717-14722.*
Pennica et al. (1998, PNAS USA 95:14717-14722).*
Tockman et al (Cancer Res., 1992, 52:2711s-2718s).*
Database GeneCore Accession No. U78076, created on May 14, 1999, last visited on Oct. 24, 2004. Lee et al. "Cloning of Mouse Sepiapterin Reductase Gene and Characterization of its promoter Region," Gene Sequence, *Biochim Biophys Acta* (1999). vol. 1445, No. 1 pp. 165-171. MPSRCH Search Report 2004, 1 page.

(Continued)

*Primary Examiner*—Sean E Aeder
(74) *Attorney, Agent, or Firm*—David Gay; Lisa E. Alexander

(57) ABSTRACT

The present invention relates to novel sequences for use in diagnosis and treatment of carcinomas, especially breast cancers. In addition, the present invention describes the use of novel compositions for use in screening methods.

5 Claims, 1 Drawing Sheet

OTHER PUBLICATIONS

International Search Report mailed on Nov. 10, 2004 for PCT patent application No. PCT/US02/41414 filed Dec. 26, 2002, 8 pages.
International Search Report mailed on Jul. 26, 2004, for PCT patent application No. PCT/US02/38582, filed on Dec. 2, 2002, 8 pages.
GenBank Accession No. AF357835. Sasaki, S.et al. (2000 ). "Cloning and Expression of Human B Cell-Specific Transcription Factor $BACH_2$ Mapped to Chromosome 6q15," *Oncogene* 19:3739-3749. (Abstract Only).
International Search Report mailed on Jun. 15, 2004, for PCT patent application No. PCT/US02/36071 filed on Nov. 8, 2002, 5 pages.
International Search Report mailed on Jun. 16, 2004, for PCT patent application No. PCT/US03/40082 filed on Dec. 15, 2003, 5 pages.
Sasaki, S.et al. (2000). "Cloning and Expression of Human B Cell-Specific Transcription Factor $BACH_2$ Mapped to Chromosome 6q15," *Oncogene* 19:3739-3749.
International Search Report mailed on Dec. 1, 2003, for PCT patent application No. PCT/US02/33835 filed on Oct. 22, 2002, 4 pages.
Berns, A. (Date unknown). "Table A: Retroviral Insertion Sties in EμMyc and EμMyc; Pim$1^{-1-}$; Pim $2^{-1-}$ Lymphomas[a]," published in the advance online issue of *Nature Genetics*, 13 pages total.
Berns, A. (Date unknown). "Web Fig A," describing PIM protein actions, published in the advance online issue of the *Nature Genetics*, 1 page total.
Campbell, A. M. (1984). "The Production and Characterization of Rodent and Human Hybridomas," Chapter 1 In *Monoclonal Antibody Technology*. Burdon, R. H and van Knippenberg, P. H., eds, Elsevier, pp. 1-32.
Database GenCore on STN, Accession No. U52152, Schoots et al. "Cloning of Four Inwardly Rectifying Potassium Channels from Human," Direction Submission Mar. 25, 1996 amino Acid and Nucleic acid Sequences.
Database GenCore on STN, on Accession No. AF275818, Yang et al. Jul. 23, 2000. "A Family of Novel PR- Domain (PRDM) Genes as Candidate Tumor Supressors".
Hunter, W. M. and Greenwood, F. C. (1962). "Preparation of Iodine-131 Labelled Human Growth Hormone of High Specific Activity," *Nature* 194:495-496.
Jiang, G-L et al. (2000). "The Yin-Yang of PR-Domain Family Genes in Tumorigenesis," *Histol. Histopathol.* 15(1):109-117.
Lohuizen, V. (Date unknown). "Web Table A," describing genomic positions insertion site sequences analyzed against the Celera Mouse Genome Database (CMGD Release 12), published in the advance online issue of *Nature Genetics*, 9 pages total.
Lohuizen, V. (Date unknown). "Web Table B," describing Genomic positions of insertion site sequences analyzed against the Ensemble Mouse Genome Database (Feb. 2002 freeze), published in the advance online issue of *Nature Genetics*, 12 pages total.
Lohuizen, V. (Date unknown). "Web Table C," listing GenBank Accession Numbers, published in the advance online issue of *Nature Genetics*, 11 pages total.
Sawai, H. et al. (1984). "Synthesis and Properties of Oligoadenylic Acids Containing 2'-5' Phosphoramide Linkage," *Chem. Lett.* pp. 805-808.
Schoots, O. et al. (1999). "Co-Expression of Human Kir3 Subunits Can Yield Channels with Different Functional Properties," *Cell Signal* 11(12):871-883.
Skinner, R. H. et al. (1991). "Use of the Glu-Glu-Phe C-Terminal Epitope for Rapid Purification of the Catalytic Domain of Normal and Mutant *Ras* GTPase-Activating Proteins," *J. Biol. Chem.* 266(22):14163-14166.
Allen, J. D. and Berns, A. (1996). "Complementation Tagging of Cooperating Oncogenes in Knockout Mice," *Cancer Biology* 7:299-306.
Altschul, S. F. and Gish, W. (1996). "Local Alignment Statistics" In *Methods in Enzymology* vol. 266, Academic Press, Inc., pp. 460-480.
Altschul, S. F. et al. (1990). "Basic Local Alignment Search Tool," *J. Mol. Biol.* 215:403-410.
Aplin, J. D. and Wriston, Jr., J. C. (1981). "Preparation, Properties, and Applications of Carbohydrate Conjugates of Proteins and Lipids," *CRC Crit. Rev. Biochem.* pp. 259-306.
Arenberg, D. A. et al. (2001). "The Murine CC Chemokine, 6C-Kine, Inhibits Tumor Growth and Angiogenesis in a Human Lung Cancer SCID Mouse Model," *Cancer Immunol. Immunother.* 49:587-592.
Ausubel, F. M. et al., eds. (1992). *Short Protocols in Molecular Biology*. Greene Publishing Associates and John Wiley & Sons, pp. iii-xviii (Table of Contents Only).
Bai, J. et al. (1999). "Sequence Comparison of JSRV with Endogenous Proviruses: Envelope Genotypes and a Novel ORF With Similarity to a G-Protein-Coupled Receptor," *Virology* 258:333-343.
Beaucage, S. L. and Iyer, R. P. (1993). "The Functionalization of Oligonucleotides Via Phosphoramidite Derivatives," *Tetrahedron* 49(10):1925-1963.
Boener, P. et al. (1991). "Production of Antigen-Specific Human Monoclonal Antibodies from in Vitro-Primed Human Splenocytes," *J. Immunol.* 147(1):86-95.
Bolli, M. et al. (1994). "α-Bicyclo-DNA: Synthesis, Characterization, and Pairing Properties of α-DNA-Analogues with Restricted Conformational Flexibility in the Sugar-Phosphate Backbone," Chapter 7 In *Carbohydrate Modifications in Antisense Research*. ACS Symposium Series 580 Shanghvi, Y. S and Cook, P. D, eds, American Chemical Society, Washington, pp. 100-117.
Brill, W. et al. (1989). "Synthesis of Oligodeoxynucleoside Phosphoridithioates via Thioamidites," *J. Am.Chem. Soc.* 111:2321-2322.
Brower, V. (1998). "Naked DNA Vaccines Come of Age," *Nature Biotechnology* 16:1304-1305.
Carlsson, C. et al. (1996). "Screening for Genetic Mutations," *Nature* 380:207 (1 page total).
Cole, S.P.C., et al. (1985). "The EBV-Hybridoma Technique and Its Application to Human Lung Cancer," In *Monoclonal Antibodies and Cancer Therapy*, Reisfeld, R. A. and Sell, S., ed., Alan R. Liss, New York, p. 77-96 (Includes Table of Contents).
Creighton, T. E., ed. (1983). "Posttranslational Covalent Modifications of Polypeptide Chains," Chapter 2.4 In *Proteins: Structure and Molecular Properties*. W. H. Freeman & Co., San Francisco pp. 78-86 (Includes Table of Contents).
David, G. S. and Reisfeld, R. A. (1974). "Protein Iodination with Solid State Lactoperoxidase," *Biochemistry* 13(5):1014-1021.
De Mesmaeker, A. et al. (1994). "Comparison of Rigid and Flexible Backbones in Antisense Oligonucleotides," *Bioorganic & Medicinal Chem. Lett.* 4(3):395-398.
De Mesmaeker, A. et al. (1994). "Novel Backbone Replacements for Oligonucleotides," Chapter 2 In *Carbohydrate Modifications in Antisense Research*. ACS Symposium Series 580 Shanghvi, Y. S and Cook, P. D, eds. American Chemical Society, Washington, pp. 24-39.
Dempcy, R. O. et al. (1995). "Synthesis of a Thymidyl Pentamer of Deoxyribonucleic Guanidine and Binding Studies with DNA Homopolynucleotides," *Proc. Natl Acad. Sci. USA* 92:6097-6101.
Desbois, C. et al. (1996). "Exclusion of *Int*-6 from PML Nuclear Bodies by Binding to the HTLV-I Tax Oncoprotein," *Science* 273:951-953.
Devereux et al. (1984). "A Comprehensive Set of Sequence Analysis Programs for the VAX," *Nuc. Acid. Res.* 12(1):387-395.
Doudney, K. et al. (2001). "Comparative Physical and Transcript Maps of ~ 1 Mb around *looptail*, a Gene for Severe Neural Tube Defects on Distal Mouse Chromosome 1 and Human Chromosome 1q22-q23," *Genomics* 72(2):180-192.
Eckstein. F., ed. (1991). *Oligonucleotides and Analogues: A Practical Approach*, Oxford University Press, vii-xvii. (Table of Contents Only).
Edge, A. S. B. et al. (1981). "Deglycosylation of Glycoproteins by Trifluoromerathneusulfonic Acid," *Anal. Biochem.* 118:131-137.
Egholm, M. (1993). "PNA Hybridizes to Complementary Oligonucleotides Obeying the Watson-Crick Hydrogenbonding," *Nature* 365:566-568.
Elgholm, M. et al. (1992). "Peptide Nucleic Acids (PNA). Oligonucleotide Analogues with an Achiral Peptide Backbone," *J. Am. Chem. Soc.* 114:1895-1897.
Erny, K. M. et al. (1996). "Involvement of the *Tpl-2lcot* Oncogene in MMTV Turmorigenesis," *Oncogene* 13:2015-2020.
Evan, G. I. et al. (1985). "Isolation of Monoclonal Antibodies Specific for Human c-myc Proto-Oncogene Product," *Biology* 5(12):3610-3616.

Fan, L. et al. (2000). "Cutting Edge: Ectopic Expression of the Chemokine TCA4/SLC is Sufficient to Trigger Lymphoid Neogenesis," *J. Immunol*. 164(8):3955-3959.
Feng, D. F. & Doolittle, R. F. (1987). "Progressive Sequence Alignment as a Prerequisite to Correct Phylogenetic Trees," *J. Mol. Evol*. 25:351-360.
Field, J. et al. (1988). "Purification of a RAS-Responsive Adenylyl Cyclase Complex from *Saccharomyces cerevisiae* by Use of a Epitope Addition Method," *Mol Cell. Biol*. 8(5):2159-2165.
Fishwild, D. M.et al. (1996). "High-Avidity Human IgGk Monoclonal Antibodies from a Novel Strain of Minilocus Transgenic Mice," *Nature Biotechnology* 14:845-851.
Gallahan, D. and Callahan, R. (1987). "Mammary Tumorigenesis in Feral Mice: Identification of a New *int* Locus in Mouse Mammary Tumor Virus (Czech II)-Induced Mammary Tumors," *J. Virol*. 61(1):66-74.
Gao, X. and Jeffs, W. P. (1994). "Unusual Conformation of a 3'-thioformacetal Linkage in a DNA Duplex," *J. Biomolecular NMR* 4:17-34.
Germer, S. et al. (2000). "High-Throughput SNP Allele-Frequency Determination in Pooled DNA Samples by Kinetic PCR," *Genome Res*. 10:258-266.
Goding, J. W. (1986). "Production of Monoclonal Antibodies," Chapter 3 In *Monoclonal Antibodies: Principles and Practice*, Academic Press, Inc. $2^{nd}$ edition, pp. 59-103.
Hansen, G. M. et al. (2000). "Genetic Profile of Insertion Mutations in Mouse Leukemias and Lymphomas," *Genome Res*. 10(2):237-243.
Heid, C. A et al. (1996). "Real Time Quantitative PCR," *Genome Research* 6:986-994.
Herdewjn, P. et al. (1994). "Hexopyranosyl-Like Oligonucleotides," Chapter 6 In *Carbohydrate Modifications in Antisense Research*. ACS Symposium Series 580, Shanghvi, Y. S and Cook, P. D, eds, American Chemical Society, Washington, pp. 80-99.
Higgins, D. G. and Sharp, P. M. (1989). "Fast and Sensitive Multiple Sequence Alignments on a Microcomputer," *CABIOS Communications* 5(2):151-153.
Hoogenboom, H. R. and Winter, G. (1992). "By-Passing Immunisation Human Antibodies from Synthetic Repertoires of Germline $V_H$ Gene Segments Rearranged in Vitro," *J. Mol. Biol*. 227:381-388.
Hopp, T. P. et al. (1988). "A Short Polypeptide Marker Sequence Useful for Recombinant Protein Identification and Purification," *Biotechnology* 6:1204-1210.
Horn, T. et al. (1996). "Oligonucleotides with Alternating Anionic and Cationic Phosphoramidate Linkages: Synthesis and Hybridization of Stereo-Uniform Isomers," *Tetrahedron Letters* 37(6):743-746.
Hwang, H. C. et al. (2002). "Identification of Oncognes Collaborating with $p27^{Kip1}$ Loss by Insertional Mutagenesis and High-Throughput Insertion Site Analysis," *Proc. Natl Acad. Sci. USA* 99(17):11293-11298 (Includes supporting information).
Jenkins, G. N. and Turner, N. J. (1995). "The Biosynthesis of Carbocyclic Nucleosides," *Chem. Soc. Rev*. pp. 169-176.
Jones, P. T. et al. (1986). "Replacing the Complementarity-Determining Regions in a Human Antibody with Those from a Mouse," *Nature* 321:522-525.
Jonkers, J. and Berns, A. (1996). "Retroviral Insertional Mutagenesis as a Strategy to Identify Cancer Genes," *Biochim. Biophys. Acta* 1287:29-57.
Joosten, M. et al. (2000). "Phenotyping of Evi 1, Evi 11/Cb2, and Evi 12 Transformed Leukemias Isolated from a Novel Panel of Cas-Br-M Murine Leukemia Virus-Infected Mice," *J. Virology* 268:308-318.
Jung, M. P. et al. (1994). "Hybridization of Alternating Cationic/Anionic Oligonucleotides to RNA Segments," *Nucleosides & Nucleotides* 13(6&7):1597-1605.
Karlin, S. et al. (1993). "Applications and Statistics for Multiple High-Scoring Segments in Molecular Sequences," *Proc. Natl Acad. Sci. USA* 90:5873-5787.
Köhler, G. and Milstein, C. (1975). "Continuous Cultures of Fused Cells Secreting Antibody of Predefined Specificity," *Nature* 256:495-497.
Kohno, T. et al. (2000). "Identification of Genes Associated with the Progression of Adult T-Cell Leukemia (ATL)," *Jpn J. Cancer Res*. 91:1103-1110.
Lee, F. S. et al. (1995). "Insertional Mutagenesis Identifies a Member of the *Wnt* Gene Family as a Candidate Oncogene in the Mammary Eptithelium of *int-2l/Fgf-3* Transgenic Mice." *Proc. Natl. Acad. Sci. USA* 92:2268-2272.
Lee, S. Wong et al. (1999). "Cloning of Mouse Sepiapterin Reductase Gene and Characterization of its Promoter Region," *Biochimica and Biophysica Acta* 1445(1):165-171.
Letsinger, R. L. et al. (1986). "Effects of Pendant Groups at Phosphorus on Binding Properties of d-ApA Analogues," *Nucl. Acids. Res* 14(8):3487-3499.
Letsinger, R. L. et al. (1988). "Cationic Oligonucleotides," *J. Am. Chem. Soc*. 110:4470-4471.
Letsinger, R.L. and Mungall, W. S. (1970). "Phosphoramidate Analogs of Oligonucleotides," *J. Org. Chem* 35(11):3800-3803.
Li, J. et al. (1999). "Leukaemia Disease Genes: Large-Scale Cloning and Pathway Predictions," *Nature Genetics* 23:348-353.
Lockhart, D. J. et al. (1996). "Expression Monitoring by Hybridization High-Density Oligonucleotide Arrays," *Nature Biotechnology* 14:1675-1680.
Lonberg, N. and Huszar, D. (1995). "Human Antibodies from Transgenic Mice," *Intern. Rev. Immunol*. 13:65-93.
Longberg, N. et al. (1994). "Antigen-Specific Human Antibodies from Mice Comprising Four Distinct Genetic Modifications," *Nature* 368:856-859.
Lund, A. H. et al. (2002). "Genome-Wide Retroviral Insertional Tagging of Genes Involved in Cancer in Cdkn2a-Deficient Mice," *Nature Genetics Advance online Publication* pp. 1-6.
Lutz-Freyermuth, C. et al. (1990). "Quantitative Determination That One of Two Potential RNA-Binding Domains of the A Protein Component of the U1 Small Nuclear Ribonucleoprotein Complex Binds with High Affinity to Stem-Loop II of U1 RNA," *Proc. Natl Acad. Sci. USA* 87:6393-6397.
MacArthur, C. A. et al. (1995). "*Fgf-8*, Activated by Proviral Insertion, Cooperates with the *Wnt-1* Transgene in Murine Mammary Tumorigenesis," *J. Virol*. 69(4):2501-2507.
Maddry, J. A. et al. (1994). "Synthesis of Nonionic Oligonucleotide Analogues," Chapter 3 In *Carbohydrate Modifications in Antisense Research*. Shanghvi, Y. S and Cook, P. D, eds, ACS Symposium Series 580, American Chemical Society, Washington, pp. 40-51.
Mag, M. et al. (1991). "Synthesis and Selective Cleavage of an Oligodeoynucleotide Containing a Bridged Internucleotide 5'-Phosphorotiate Linkage," *Nucleic Acids Res*. 19:1437-1441.
Marchetti, A. et al. (1995). "*Int-6*, a Highly Conserved, Widely Expressed Gene, is Mutated by Mouse Mammary Tumor Virus in Mammary Preneoplasia," *J. Virol*. 69:1932-1938.
Marks, J. D. et al. (1991). "By-Passing Immunization, Human Antibodies from V-Gene Libraries Displayed on Phage," *J. Mol. Biol*. 222:581-597.
Marks, J. D. et al. (1992). "By-Passing Immunization: Building High Affinity Human Antibodies by Chain Shuffling," *Bio/Technology* 10:779-783.
Martin, G. A. et al. (1992). "GAP Domains Responsible for Ras p21-Dependent Inhibition of Muscarinic Atrial K+ Channel Currents," *Science* 255:192-194.
Meier, C. and Engels, J.W. (1992). "Peptide Nucleic Acids (PNAs)—Unusual Properties of Nonionic Oligonucleotide Analogues," *Angew Chem. Int. Ed. Engl*. 31(8):1008-1010.
Mikkers ,H. et al. (2002). "High-Throughput Retroviral Tagging to Identify Components of Specific Signaling Pathways in Cancer," *Nature Genetics Advance Online Publication*, pp. 1-7.
Moore, A. S. (2001). "The Role of Chemoattraction in Cancer Metastases," *BioEssays* 23:674-676.
Morris, D. W. et al. (1986). "Transfer, by Selective Breeding, of the Pathogenic *Mtv-2* Endogenous Provirus from the GR strain to a Wild Mouse Line Free of Endogenous and Exogenous Mouse Mammary Tumor Virus," *J. Virol*. 58(2):247-252.
Morris, D. W. et al. (1990). "Insertion Mutation of the *Int-1* and *Int-2* Loci by Mouse Mammary Tumor Virus in Premalignant and Malignant Neoplasms from the GR Mouse Strain," *J. Virol*. 64(4):1794-1802.
Morrison, S. L. (1994). "Success in Specification," *Nature* 368:812-813.

Müller, A. et al. (2001). "Involvement of Chemokine Receptors in Breast Cancer Metastasis," *Nature* 410:50-56.
Needleman, S. B. and Wunsch, C. D. (1970). "A General Method Applicable to the Search for Similiarities in the Amino Acid Sequence of Two Proteins," *J. Mol. Biol.* 48:443-453.
Neuberger, M. (1996). "Generating High-Avidity Human Mabs in Mice," *Nature Biotechnology* 14:826 (1 page total).
Nusse, R. and Varmus, H. E. (1982). "Many Tumors Induced by the Mouse Mammary Tumor Virus Contain a Provirus Integrated in the Same Region of the Host Genome," *Cell* 31:99-109.
Nygren, H. (1982). "Conjugation of Horseradish Peroxidase to Fab Fragments with Different Homobifunctional and Heterobifunctional Cross-Linking Reagents," The J. *Histochem and Cytochem* 30(5):407-412.
Paborsky, L. R. et al. (1990). "Mammalian Cell Transient Expression of Tissue Factor for the Production of Antigen," *Protein Engineering* 3(6):547-553.
Pain, D. and Surolia, A. (1999). "Preparation of Protein A-Peroxidase Monoconjugate Using A Heterobifunctional Reagent, and its Use In Enzyme Immunoassays," *J. Immunol. Meth*. 40:219-230.
Palmarini, M. and Surolia, A. (1981). "Jaagsiekte Sheep Retrovirus is Necessary and Sufficient to Induce a Contagious Lung Cancer in Sheep," *J. Virol*. 73(8):6964-6972.
Pauwels, R. et al. (1986). "Biological Activity of New 2-5A Analogues," *Chemica Scripta* 26:141-145.
Pearson, W. R. & Lipman, D. J. (1988). "Improved Tools for Biological Sequence Comparison," *Proc. Natl. Acad. Sci USA* 85:2444-2448.
Peters, G. et al. (1983). "Tumorigenesis by Mouse Mammary Turmor Virus: Evidence for a Common Region for Provirus Integration in Mammary Tumors," *Cell* 33:369-377.
Peters, G. et al. (1989). "The Mouse Homolog of the *Hst/k-FGF* Gene is Adjacent to *int-2* and is Activated by Proviral Insertion in Some Virally Induced Mammary Tumors," *Proc. Natl. Acad. Sci. USA* 86:5678-5682.
Pierce (1994). "Cross-Linking," *Pierce Catalog and Handbook* pp. 155-200.
Presta, L. G. (1992). "Antibody Engineering", *Current Opinion in Structural Biology* 2:593-596.
Rawls, R. L. (1997). "Optimistic About Antisense," *C & E News* pp. 35-40.
Riechmann, L. et al. (1988). "Reshaping Human Antibodies for Therapy," *Nature* 332:323-327.
Roelink, H. et al. (1990). "*Wnt-3*, a Gene Activated by Proviral Insertion in Mouse Mammary Tumors is Homologous to *int-1/Wnt-1* and is Normally Expressed in Mouse Embryos and Adult Brain," *Proc. Natl. Acad. Sci USA* 87:4519-4523.
Sambrook, J. et al., eds. (1989). *Molecular Cloning, a Laboratory Manual*, Second Edition. Cold Spring Harbor Laboraroty Press. pp. xi-xxxviii. (Table of Contents Only).
Scopes, R. K.,ed. (1982). *Protein Purification: Principles and Practice*. Springer-Verlag, New York, Heidelberg, Berlin, pp. xi-xiii.
Shiramizu, B. et al. (1994). "Identification of a Common Clonal Human Immunodeficiency Virus Integration Site in Human Immunodeficiency Virus-Associated Lymphomas," *Cancer Res*. 54:2069-2072.
Smith, T. F. and Waterman, M. S. (1981). "Comparison of Biosequences," *Adv. Appl. Math*. 2:482-489.
Sojar, H. T. and Bahl, O. P. (1987). "A Chemical Method for the Deglycosylation of Proteins," *Archives of Biochemistry and Biophysics* 259(1):52-57.
Sorensen, A. B. et al. (1993). "Amplification and Sequence Analysis of DNA Flanking Integrated Proviruses by a Simple Two-Step Polymerase Chain Reaction Method," *Journal of Virology* 67(12):7118-7124.
Sorensen, A. B. et al. (1996). "Sequence Tags of Provirus Integration Sites in DNAs of Tumors Induced by the Murine Retrovirus SL3-3," *Journal of Virology* 70(6):4063-4070.
Sorensen, A. B. et al. (2000). "Sintl, a Common Integration Site in SL3-3-Induced T-Cell Lymphomas, Harbors a Putative Proto-Oncogene with Homology to the Septin Gene Family," *Journal of Virology* 74(5):2161-2168.
Sprinzl, M. et al. (1977). "Enzymatic Incorporation of ATP and CTP Analogues Into the 3' End of tRNA," *Eur. J. Biochem* 81:579-589.
Stein, C. A. and Cohen, J. S. (1988). "Oligodeoxynucleotides as Inhibitors of Gene Expression: A Review," *Cancer Res*. 48:2659-2668.
Sternsdorf, T. et al. (1997). "Nuclear Dots: Actors on Many Stages," *Immunobiology* 198:307-331.
Suzuki, T. et al. (2002). "New Genes Involved in Cancer Identified by Retroviral Tagging," *Nature Genetics Advance Online Publication* pp. 1-9.
Suzuki, T. et al. (2002). "Web Note A, CIS Definition, Retroviral Tagging in the Post-Genome Era Identifies New Genes Involved in Cancer". (1 page total).
Thotakura, N. R. and Bahl, O. P. (1987). "Enzymathic Deglycosylation of Glycoproteins," In *Methods in Enzymology* vol. 138. Academic Press, Inc., pp. 350-359.
Tijssen (1993). "Overview of Principles of Hybridization and the strategy of nucleic acid assays," Chapter 2 In *Laboratory Techniques in Biochemistry and Molecular Biology*, Hybridization with Nucleic Acid Probes vol. 24 Van der Vliet, P. C., ed. Elsevier, Amsterdam, London, New York, and Tokyo, vol. 24 pp. 20-78.
Van der Krol, A. R et al. (1988). "Modulation of Eurkaryotic Gene Expression by Complementary RNA or DNA Sequences," *Biotechniques* 6(10):958-976.
Varmus, H. E. (1983). "Using Retroviruses as Insertional Mutagens to Identify Cellular Oncogenes," In *Oncogenes and Retroviruses: Evaluation of Basic Findings and Clinical Potential*. Alan R. Liss, Inc., New York. pp. 23-35.
Vaughn, J. et al. (2000). "Genomic Structure and Expression of Human *KCNJ9* (Kir3.3/GIRK3)," *Biochem. Biophys. Res. Commun*. 274(2):302-309.
Verhoeyen, M. et al. (1988). "Reshaping Human Antibodies: Grafting an Antilysozyme Activity," *Science* 239:1534-1536.
von Kiedrowski, G. et al. (1991). "Parabolic Growth of a Self-Replicating Hexadeoxynucleotide Bearing a 3'-5'-Phosphoamidate Linkage," *Angew. Chem. Int. Ed. Engl* 30(4):423-426.
Washington University. (2002). "Washington University BLAST Archives" located at <http://blast.wustl.edu> visited on Dec. 15, 2002, three pages.
Wolford, J. K. (2001). "Analysis of Linkage Disequilibrium Between Polymorphisms in the *KCNJ9* Gene with Type 2 Diabetes Mellitus in Pima Indians," *Mol. Genet. Metab*. 73(1):97-103.
Zhang, W-X and Yang, S. Y. (2000). "Cloning and Characterization of a New Member of the T-Box Gene Family," *Genomics* 70(1):41-48.
Zlokarnik, G. et al. (1998). "Quantitation of Transcription and Clonal Selection of Single Living Cells with β-Lactamase as Reporter," *Science* 279:84-88.
Database EMBL, Nov. 6, 2003, Morris, DW, "Mouse Kcnj9 carcinoma associated coding sequence, Seq. ID No. 1579", Database Accession No. ADA03061.
Database EMBL, Dec. 4, 2003, Morris, DW, "Mouse Kcnj9, Seq. ID No. 627", Database Accession No. ADB72799.
Lesage, Florian et al., "Cloning provides evidence for a family of inward rectifier and G-protein coupled K+ channels in the brain", FEBS Letters, vol. 353, No. 1, 1994, pp. 37-42.
Hansen, G. M., et al., "Genetic profile of insertion mutations in mouse leukemias and lymphomas", Genome Research, Cold Spring Harbor Laboratory Press, Woodbury, NY, US, vol. 10, No. 2, Feb. 2, 2000, pp. 237-243.
Hwang, Harry C., et al., "Identification of oncogenes collaborating with p27Kip1 loss by insertional mutagenesis and high-throughput insertion site analysis", Proceedings of the National Academy of Sciences of the United States of America, vol. 99, No. 17, Aug. 20, 2002, pp. 11293-11298.
Jetten, A. M., et al., "The ROR Nuclear Orphan Receptor Subfamily: Critical Regulators of Multiple Biological Processes", Progress in Nucleic Acid Research and Molecular Biology, Academic Press, US, vol. 69, 2001, pp. 205-247.
Joosten, M., et al., "Phenotyping of Evil, Evil1/Cb2, and Evil2 Transformed Leukemias Isolated from a Novel Panel of Cas-Br-M Murine Leukemia Virus-Infected Mice", Virology, Academic Press, Orlando, US, vol. 268, No. 2, Mar. 15, 2000, pp. 308-318.

Lesage, F., et al., “Cloning provides evidence for a family of inward rectifier and G-protein coupled K+ channels in the brain”, FEBS Letters, vol. 353, No. 1, 1994, pp. 37-42.
Li, J., et al., “Leukaemia disease genes: Large-scale cloning and pathway predictions”, Nature Genetics, Nature America, New York, US, vol. 23, No. 3, Nov. 1999, pp. 348-353.
Kurebayashi, Shogo, et al., “Accelerated apoptosis in thymocytes and induction of T cell lymphoma formation in RORgamma-deficient mice”, Proceedings of the American Association for Cancer Research Annual Meeting, vol. 42, Mar. 2001, p. 552.
Medvedev, A., et al., “Cloning of a cDNA encoding the murine orphan receptor RZR/RORgamma and characterization of its response element”, Gene: An International Journal on Genes and Genomes, Elsevier, Amsterdam, NL, vol. 181, No. 1-2, Nov. 28, 1996, pp. 199-206.
Medvedev, A., et al., “Genomic Structure and Chromosomal Mapping of the Nuclear Orphan Receptor RORgamma (RORC) Gene”, Genomics, Academic Press, San Diego, US, vol. 46, No. 1, Nov. 15, 1997, pp. 93-102.
Morris, David W., “Mouse Kcnj9 cDNA”, Seq. ID No. 627; Database Accession No. ADB72799.
Morris, David W., “Mouse Kcnj9 carcinoma associated coding sequence”, Seq. ID No. 1579, Database Accession No. ADA03061.
Ueda, Eiichiro, et al., “Abnormal thymopoiesis and development of T cell lymphoma formation in RORgamma-deficient mice”, Faseb Journal, vol. 15, No. 5, Mar. 8, 2001, p. A1193.
Ueda, Eiichiro, et al., “High incidence of T-cell lymphomas in mice deficient in the retinoid-related orphan receptor RORgamma”, Cancer Research, vol. 62, No. 3, Feb. 1, 2002, pp. 901-909.
Lesage et al. “Cloning provides evidence for a family of inward rectifier and G-protein coupled $K^+$ channels in the brain,” *FEBS Letters* 353:37-42 (1994).

* cited by examiner

COMPOSITIONS AND METHODS IN CANCER ASSOCIATED WITH ALTERED EXPRESSION OF KCNJ9

The present application is a continuing application of U.S. application entitled Novel Compositions and Methods for Cancer, U.S. Ser. No. 10/034,650, filed Dec. 20, 2001, and U.S. Ser. No. 09/747,377, filed Dec. 22, 2000, and Ser. No. 09/798,586, filed Mar. 2, 2001 all of which are expressly incorporated herein by reference.

FIELD OF THE INVENTION

The present invention relates to novel sequences for use in diagnosis and treatment of cancer, especially carcinomas including breast cancer, as well as the use of the novel compositions in screening methods.

BACKGROUND OF THE INVENTION

Oncogenes are genes that can cause cancer. Carcinogenesis can occur by a wide variety of mechanisms, including infection of cells by viruses containing oncogenes, activation of protooncogenes in the host genome, and mutations of protooncogenes and tumor suppressor genes.

There are a number of viruses known to be involved in human cancer as well as in animal cancer. Of particular interest here are viruses that do not contain oncogenes themselves; these are slow-transforming retroviruses. They induce tumors by integrating into the host genome and affecting neighboring protooncogenes in a variety of ways, including promoter insertion, enhancer insertion, and/or truncation of a protooncogene or tumor suppressor gene. The analysis of sequences at or near the insertion sites led to the identification of a number of new protooncogenes.

With respect to lymphoma and leukemia, murine leukemia retrovirus (MuLV), such as SL3-3 or Akv, is a potent inducer of tumors when inoculated into susceptible newborn mice, or when carried in the germline. A number of sequences have been identified as relevant in the induction of lymphoma and leukemia by analyzing the insertion sites; see Sorensen et al., J. of Virology 74:2161 (2000); Hansen et al., Genome Res. 10(2):237-43 (2000); Sorensen et al., J. Virology 70:4063 (1996); Sorensen et al., J. Virology 67:7118 (1993); Joosten et al., Virology 268:308 (2000); and Li et al., Nature Genetics 23:348 (1999); all of which are expressly incorporated by reference herein.

In addition, breast cancer is one of the most significant diseases that affects women. At the current rate, American women have a 1 in 8 risk of developing breast cancer by age 95 (American Cancer Society, 1992). Treatment of breast cancer at later stages is often futile and disfiguring, making early detection a high priority in medical management of the disease.

KCNJ9 (Kir 3.3, GIRK3) is a member of the G-protein-activated inwardly rectifying potassium (GIRK) channel family. Vaughn J. et al., *Biochem Biophys Res Commun* (2000) Aug. 2; 274(2):302-9. In particular, the KCNJ9 gene encodes a G-protein-coupled inwardly rectifying potassium channel. Wolford J. K. et al., *Mol Genet Metab* (2001) May; 73(1):97-103.

The gene spans approximately 7.6 kb and contains one noncoding and two coding exons separated by approximately 2.2 and approximately 2.6 kb introns, respectively. Fourteen single nucleotide polymorphisms (SNPs), including one that predicts a Val366Ala substitution, and an 8 base-pair (bp) insertion/deletion have been identified, and earlier expression studies have revealed the presence of the transcript in various human tissues including pancreas, and two major insulin-responsive tissues: fat and skeletal muscle.

The comparative gene content and order are identical between mouse and human, indicating a high degree of conservation between the two species in the KCNJ9 region. Doudney K. et al., *Genomics* (2001) Mar. 1; 72(2):180-92. The genomic organization of the KCNJ9 locus on chromosome 1q21-23=makes it a candidate gene for Type II diabetes mellitus in the Pima Indian population. KCNJ9, however, has not before been associated with or implicated in cancer. All references cited herein are expressly incorporated in their entirety.

As demonstrated below, mutations that interrupt the KCNJ9 coding sequence result in cancer. Moreover, altered expression of KCNJ9 correlate with cancer, in particular with breast cancer.

Accordingly, it is an object of the invention to provide sequences involved in cancer and in particular in oncogenesis and breast cancer.

SUMMARY OF THE INVENTION

In accordance with the objects outlined above, the present invention provides methods for screening for compositions which modulate carcinomas, especially breast cancer. Also provided herein are methods of inhibiting proliferation of a cell, preferably a breast cancer cell. Methods of treatment of carcinomas, including diagnosis, are also provided herein.

In one aspect, a method of screening drug candidates comprises providing a cell that expresses a carcinoma associated (CA) gene or fragments thereof, such as KCNJ9. Preferred embodiments of CA genes are genes which are differentially expressed in cancer cells, preferably lymphatic, breast, prostate or epithelial cells, compared to other cells. Preferred embodiments of CA genes used in the methods herein include, but are not limited to the nucleic acids selected from Table 1. The method further includes adding a drug candidate to the cell and determining the effect of the drug candidate on the expression of the CA gene.

In one embodiment, the method of screening drug candidates includes comparing the level of expression in the absence of the drug candidate to the level of expression in the presence of the drug candidate.

Also provided herein is a method of screening for a bioactive agent capable of binding to a CA protein (CAP), the method comprising combining the CAP and a candidate bioactive agent, and determining the binding of the candidate agent to the CAP.

Further provided herein is a method for screening for a bioactive agent capable of modulating the activity of a CAP. In one embodiment, the method comprises combining the CAP and a candidate bioactive agent, and determining the effect of the candidate agent on the bioactivity of the CAP.

Also provided is a method of evaluating the effect of a candidate carcinoma drug comprising administering the drug to a patient and removing a cell sample from the patient. The expression profile of the cell is then determined. This method may further comprise comparing the expression profile of the patient to an expression profile of a healthy individual.

In a further aspect, a method for inhibiting the activity of an CA protein is provided. In one embodiment, the method comprises administering to a patient an inhibitor of a CA protein preferably selected from the group consisting of the sequences outlined in Table 1 or their complements.

A method of neutralizing the effect of a CA protein, preferably a protein encoded by a nucleic acid selected from the group of sequences outlined in Table 1, is also provided. Preferably, the method comprises contacting an agent specific for said protein with said protein in an amount sufficient to effect neutralization.

Moreover, provided herein is a biochip comprising a nucleic acid segment which encodes a CA protein, preferably selected from the sequences outlined in Table 1.

Also provided herein is a method for diagnosing or determining the propensity to carcinomas, especially breast cancer by sequencing at least one carcinoma or breast cancer gene of an individual. In yet another aspect of the invention, a method is provided for determining carcinoma including breast cancer gene copy number in an individual.

Novel sequences are also provided herein. Preferred compositions include the sequences set forth in Table 1. Other aspects of the invention will become apparent to the skilled artisan by the following description of the invention.

DETAILED DESCRIPTION OF THE INVENTION

Figure 1:
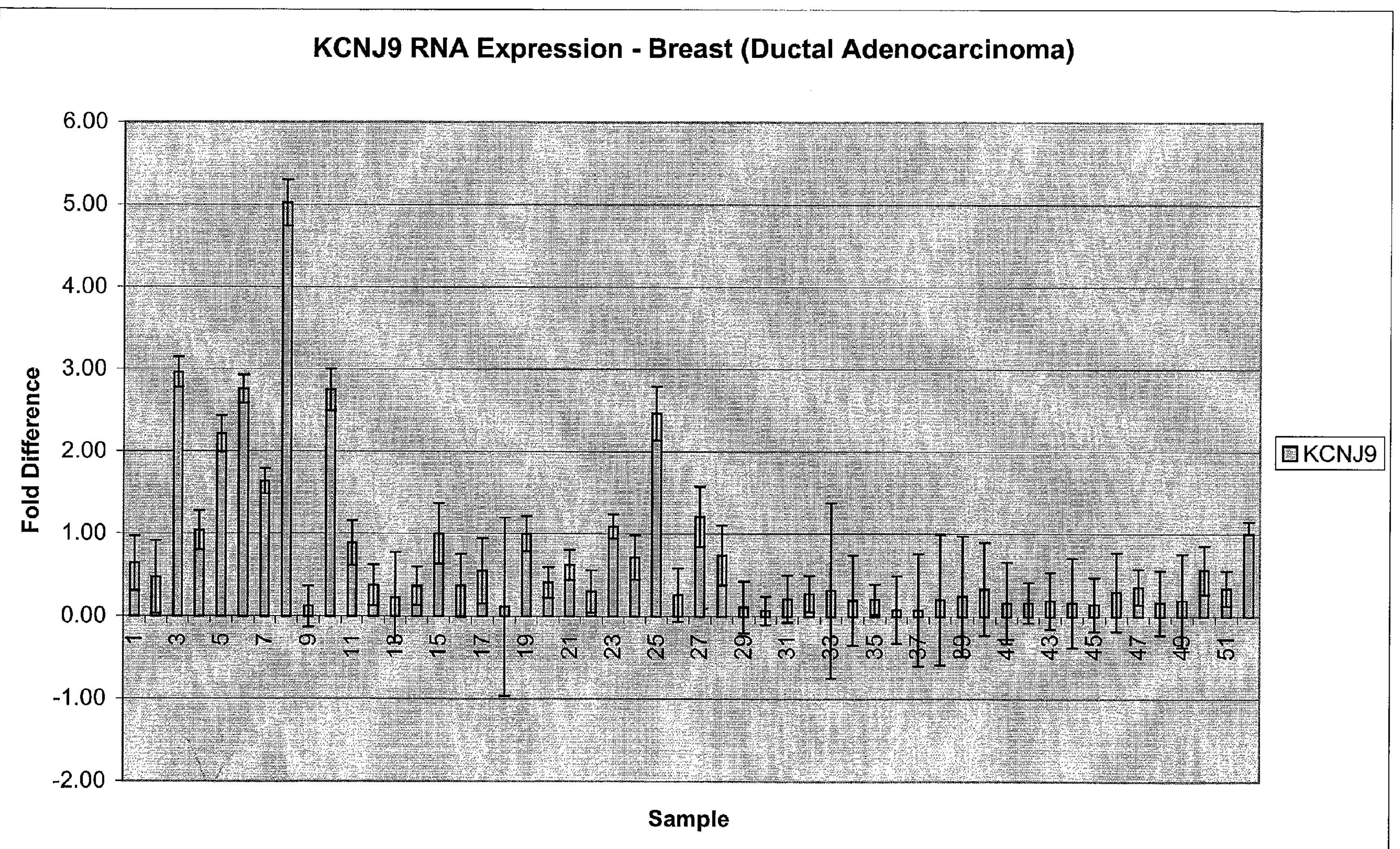
FIG. 1 depicts mRNA expression of KCNJ9 in breast cancer tissue compared with expression in normal tissue. Samples 1-50 are breast cancer samples. Samples 51 and 52 are normal tissue. Bars represent the mean of expression level. Error bars represent standard deviation.

The present invention is directed to a number of sequences associated with carcinomas, especially lymphoma, breast cancer or prostate cancer. The relatively tight linkage between clonally-integrated proviruses and protooncogenes forms "provirus tagging", in which slow-transforming retroviruses that act by an insertion mutation mechanism are used to isolate protooncogenes. In some models, uninfected animals have low cancer rates, and infected animals have high cancer rates. It is known that many of the retroviruses involved do not carry transduced host protooncogenes or pathogenic trans-acting viral genes, and thus the cancer incidence must therefor be a direct consequence of proviral integration effects into host protooncogenes. Since proviral integration is random, rare integrants will "activate" host protooncogenes that provide a selective growth advantage, and these rare events result in new proviruses at clonal stoichiometries in tumors.

The use of oncogenic retroviruses, whose sequences insert into the genome of the host organism resulting in carcinoma, allows the identification of host sequences involved in carcinoma. These sequences may then be used in a number of different ways, including diagnosis, prognosis, screening for modulators (including both agonists and antagonists), antibody generation (for immunotherapy and imaging), etc. However, as will be appreciated by those in the art, oncogenes that are identified in one type of cancer such as breast cancer have a strong likelihood of being involved in other types of cancers as well. Thus, while the sequences outlined herein are initially identified as correlated with breast cancer, they can also be found in other types of cancers as well, outlined below.

Accordingly, the present invention provides nucleic acid and protein sequences that are associated with carcinoma, herein termed "carcinoma associated" or "CA" sequences. In a preferred embodiment, the present invention provides nucleic acid and protein sequences that are associated with carcinomas which originate in mammary tissue, which are known as breast cancer sequences or "BA".

Suitable cancers which can be diagnosed or screened for using the methods of the present invention include cancers classified by site or by histological type. Cancers classified by site include cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, nos; ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); cancers of the lymphomas (hodgkin's disease and non-hodgkin's lymphoma), multiple myeloma, and leukemias (lymphocytic leukemia; myeloid leukemia; monocytic leukemia; and other leukemias).

Other cancers, classified by histological type, that may be associated with the sequences of the invention include, but are not limited to, Neoplasm, malignant; Carcinoma, NOS; Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Branchiolo-alveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Nonencapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extra-mammary paraganglioma, malignant; Pheochromocytoma; Glomangiosarcoma; Malignant melanoma, NOS; Amelanotic melanoma; Superficial spreading melanoma; Malig melanoma in giant pigmented nevus; Epithelioid cell melanoma; Blue nevus, malignant; Sarcoma, NOS; Fibrosarcoma, NOS; Fibrous histiocytoma, malignant;

Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovarii, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

In addition, the genes may be involved in other diseases, such as but not limited to diseases associated with aging or neurodegenerative diseases.

Association in this context means that the nucleotide or protein sequences are either differentially expressed, activated, inactivated or altered in carcinomas as compared to normal tissue. As outlined below, CA sequences include those that are up-regulated (i.e. expressed at a higher level), as well as those that are down-regulated (i.e. expressed at a lower level), in carcinomas. CA sequences also include sequences which have been altered (i.e., truncated sequences or sequences with substitutions, deletions or insertions, including point mutations) and show either the same expression profile or an altered profile. In a preferred embodiment, the CA sequences are from humans; however, as will be appreciated by those in the art, CA sequences from other organisms may be useful in animal models of disease and drug evaluation; thus, other CA sequences are provided, from vertebrates, including mammals, including rodents (rats, mice, hamsters, guinea pigs, etc.), primates, farm animals (including sheep, goats, pigs, cows, horses, etc). In some cases, prokaryotic CA sequences may be useful. CA sequences from other organisms may be obtained using the techniques outlined below.

CA sequences can include both nucleic acid and amino acid sequences. In a preferred embodiment, the CA sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an CA protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In a preferred embodiment, the CA sequences are nucleic acids. As will be appreciated by those in the art and is more fully outlined below, CA sequences are useful in a variety of applications, including diagnostic applications, which will detect naturally occurring nucleic acids, as well as screening applications; for example, biochips comprising nucleic acid probes to the CA sequences can be generated. In the broadest sense, then, by "nucleic acid" or "oligonucleotide" or grammatical equivalents herein means at least two nucleotides covalently linked together. A nucleic acid of the present invention will generally contain phosphodiester bonds, although in some cases, as outlined below (for example in antisense applications or when a candidate agent is a nucleic acid), nucleic acid analogs may be used that have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:

566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done for a variety of reasons, for example to increase the stability and half-life of such molecules in physiological environments for use in anti-sense applications or as probes on a biochip.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. As will be appreciated by those in the art, the depiction of a single strand "Watson" also defines the sequence of the other strand "Crick"; thus the sequences described herein also includes the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

An CA sequence can be initially identified by substantial nucleic acid and/or amino acid sequence homology to the CA sequences outlined herein. Such homology can be based upon the overall nucleic acid or amino acid sequence, and is generally determined as outlined below, using either homology programs or hybridization conditions.

The CA sequences of the invention were initially identified as described herein; basically, infection of mice with murine leukemia viruses (MLV) resulted in lymphoma. The sequences were subsequently validated by determining expression levels of the gene product, i.e. mRNA, in breast cancer samples.

The CA sequences outlined herein comprise the insertion sites for the virus. In general, the retrovirus can cause carcinomas in three basic ways: first of all, by inserting upstream of a normally silent host gene and activating it (e.g. promoter insertion); secondly, by truncating a host gene that leads to oncogenesis; or by enhancing the transcription of a neighboring gene. For example, retrovirus enhancers, including SL3-3, are known to act on genes up to approximately 200 kilobases of the insertion site.

In a preferred embodiment, CA sequences are those that are up-regulated in carcinomas; that is, the expression of these genes is higher in carcinoma tissue as compared to normal tissue of the same differentiation stage. "Up-regulation" as used herein means at least about 50%, more preferably at least about 100%, more preferably at least about 150%, more preferably, at least about 200%, with from 300 to at least 1000% being especially preferred.

In a preferred embodiment, CA sequences are those that are down-regulated in carcinomas; that is, the expression of these genes is lower in carcinoma tissue as compared to normal I tissue of the same differentiation stage. "Down-regulation" as used herein means at least about 50%, more preferably at least about 100%, more preferably at least about 150%, more preferably, at least about 200%, with from 300 to at least 1000% being especially preferred.

In a preferred embodiment, CA sequences are those that are altered but show either the same expression profile or an altered profile as compared to normal lymphoid tissue of the same differentiation stage. "Altered CA sequences" as used herein refers to sequences which are truncated, contain insertions or contain point mutations.

CA proteins of the present invention may be classified as secreted proteins, transmembrane proteins or intracellular proteins.

In a preferred embodiment the CA protein is an intracellular protein. Intracellular proteins may be found in the cytoplasm and/or in the nucleus. Intracellular proteins are involved in all aspects of cellular function and replication (including, for example, signaling pathways); aberrant expression of such proteins results in unregulated or disregulated cellular processes. For example, many intracellular proteins have enzymatic activity such as protein kinase activity, protein phosphatase activity, protease activity, nucleotide cyclase activity, polymerase activity and the like. Intracellular proteins also serve as docking proteins that are involved in organizing complexes of proteins, or targeting proteins to various subcellular localizations, and are involved in maintaining the structural integrity of organelles.

An increasingly appreciated concept in characterizing intracellular proteins is the presence in the proteins of one or more motifs for which defined functions have been attributed. In addition to the highly conserved sequences found in the enzymatic domain of proteins, highly conserved sequences have been identified in proteins that are involved in protein-protein interaction. For example, Src-homology-2 (SH2) domains bind tyrosine-phosphorylated targets in a sequence dependent manner. PTB domains, which are distinct from SH2 domains, also bind tyrosine phosphorylated targets. SH3 domains bind to proline-rich targets. In addition, PH domains, tetratricopeptide repeats and WD domains to name only a few, have been shown to mediate protein-protein interactions. Some of these may also be involved in binding to phospholipids or other second messengers. As will be appreciated by one of ordinary skill in the art, these motifs can be identified on the basis of primary sequence; thus, an analysis of the sequence of proteins may provide insight into both the enzymatic potential of the molecule and/or molecules with which the protein may associate.

In a preferred embodiment, the CA sequences are transmembrane proteins. Transmembrane proteins are molecules that span the phospholipid bilayer of a cell. They may have an intracellular domain, an extracellular domain, or both. The intracellular domains of such proteins may have a number of functions including those already described for intracellular proteins. For example, the intracellular domain may have enzymatic activity and/or may serve as a binding site for additional proteins. Frequently the intracellular domain of transmembrane proteins serves both roles. For example certain receptor tyrosine kinases have both protein kinase activity and SH2 domains. In addition, autophosphorylation of tyrosines on the receptor molecule itself, creates binding sites for additional SH2 domain containing proteins.

Transmembrane proteins may contain from one to many transmembrane domains. For example, receptor tyrosine kinases, certain cytokine receptors, receptor guanylyl cyclases and receptor serine/threonine protein kinases contain a single transmembrane domain. However, various other proteins including channels and adenylyl cyclases contain numerous transmembrane domains. Many important cell surface receptors are classified as "seven transmembrane domain" proteins, as they contain 7 membrane spanning regions. Important transmembrane protein receptors include, but are not limited to insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g. IL-1 receptor, IL-2 receptor, etc.

Characteristics of transmembrane domains include approximately 20 consecutive hydrophobic amino acids that may be followed by charged amino acids. Therefore, upon analysis of the amino acid sequence of a particular protein, the localization and number of transmembrane domains within the protein may be predicted.

The extracellular domains of transmembrane proteins are diverse; however, conserved motifs are found repeatedly among various extracellular domains. Conserved structure and/or functions have been ascribed to different extracellular motifs. For example, cytokine receptors are characterized by a cluster of cysteines and a WSXWS (W=tryptophan, S=serine, X=any amino acid) (SEQ ID NO: 7) motif. Immunoglobulin-like domains are highly conserved. Mucin-like domains may be involved in cell adhesion and leucine-rich repeats participate in protein-protein interactions.

Many extracellular domains are involved in binding to other molecules. In one aspect, extracellular domains are receptors. Factors that bind the receptor domain include circulating ligands, which may be peptides, proteins, or small molecules such as adenosine and the like. For example, growth factors such as EGF, FGF and PDGF are circulating growth factors that bind to their cognate receptors to initiate a variety of cellular responses. Other factors include cytokines, mitogenic factors, neurotrophic factors and the like. Extracellular domains also bind to cell-associated molecules. In this respect, they mediate cell-cell interactions. Cell-associated ligands can be tethered to the cell for example via a glycosylphosphatidylinositol (GPI) anchor, or may themselves be transmembrane proteins. Extracellular domains also associate with the extracellular matrix and contribute to the maintenance of the cell structure.

CA proteins that are transmembrane are particularly preferred in the present invention as they are good targets for immunotherapeutics, as are described herein. In addition, as outlined below, transmembrane proteins can be also useful in imaging modalities.

It will also be appreciated by those in the art that a transmembrane protein can be made soluble by removing transmembrane sequences, for example through recombinant methods. Furthermore, transmembrane proteins that have been made soluble can be made to be secreted through recombinant means by adding an appropriate signal sequence.

In a preferred embodiment, the CA proteins are secreted proteins; the secretion of which can be either constitutive or regulated. These proteins have a signal peptide or signal sequence that targets the molecule to the secretory pathway. Secreted proteins are involved in numerous physiological events; by virtue of their circulating nature, they serve to transmit signals to various other cell types. The secreted protein may function in an autocrine manner (acting on the cell that secreted the factor), a paracrine manner (acting on cells in close proximity to the cell that secreted the factor) or an endocrine manner (acting on cells at a distance). Thus secreted molecules find use in modulating or altering numerous aspects of physiology. CA proteins that are secreted proteins are particularly preferred in the present invention as they serve as good targets for diagnostic markers, for example for blood tests.

An CA sequence is initially identified by substantial nucleic acid and/or amino acid sequence homology to the CA sequences outlined herein. Such homology can be based upon the overall nucleic acid or amino acid sequence, and is generally determined as outlined below, using either homology programs or hybridization conditions.

As used herein, a nucleic acid is a "CA nucleic acid" if the overall homology of the nucleic acid sequence to one of the nucleic acids of Table 1 is preferably greater than about 75%, more preferably greater than about 80%, even more preferably greater than about 85% and most preferably greater than 90%. In some embodiments the homology will be as high as about 93 to 95 or 98%. In a preferred embodiment, the sequences which are used to determine sequence identity or similarity are selected from those of the nucleic acids of Table 1. In another embodiment, the sequences are naturally occurring allelic variants of the sequences of the nucleic acids of Table 1. In another embodiment, the sequences are sequence variants as further described herein.

Homology in this context means sequence similarity or identity, with identity being preferred. A preferred comparison for homology purposes is to compare the sequence containing sequencing errors to the correct sequence. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., Methods in Enzymology, 266: 460-480 (1996); http://blast.wustl]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the nucleic acids of Table 1. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleotides than those of the nucleic acids of Table 1, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the nucleic acid homology is determined through hybridization studies. Thus, for example, nucleic acids which hybridize under high stringency to the nucleic acids identified in the figures, or their complements, are considered CA sequences. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

In addition, the CA nucleic acid sequences of the invention are fragments of larger genes, i.e. they are nucleic acid segments. Alternatively, the CA nucleic acid sequences can serve as indicators of oncogene position, for example, the CA sequence may be an enhancer that activates a protooncogene. "Genes" in this context includes coding regions, non-coding regions, and mixtures of coding and non-coding regions. Accordingly, as will be appreciated by those in the art, using the sequences provided herein, additional sequences of the CA genes can be obtained, using techniques well known in the art for cloning either longer sequences or the full length sequences; see Maniatis et al., and Ausubel, et al., supra, hereby expressly incorporated by reference. In general, this is done using PCR, for example, kinetic PCR.

Once the CA nucleic acid is identified, it can be cloned and, if necessary, its constituent parts recombined to form the entire CA nucleic acid. Once isolated from its natural source, e.g., contained within a plasmid or other vector or excised therefrom as a linear nucleic acid segment, the recombinant CA nucleic acid can be further used as a probe to identify and isolate other CA nucleic acids, for example additional coding regions. It can also be used as a "precursor" nucleic acid to make modified or variant CA nucleic acids and proteins.

The CA nucleic acids of the present invention are used in several ways. In a first embodiment, nucleic acid probes to the CA nucleic acids are made and attached to biochips to be used in screening and diagnostic methods, as outlined below, or for administration, for example for gene therapy and/or antisense applications. Alternatively, the CA nucleic acids that include coding regions of CA proteins can be put into expression vectors for the expression of CA proteins, again either for screening purposes or for administration to a patient.

In a preferred embodiment, nucleic acid probes to CA nucleic acids (both the nucleic acid sequences outlined in the figures and/or the complements thereof) are made. The nucleic acid probes attached to the biochip are designed to be substantially complementary to the CA nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e. have some sequence in common), or separate.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, resins, silica or silica-based materials including silicon and modified silicon, carbon, metals, inorganic glasses, etc. In general, the substrates allow optical detection and do not appreciably fluoresce.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affymetrix GeneChip technology.

In addition to the solid-phase technology represented by biochip arrays, gene expression can also be quantified using liquid-phase arrays. One such system is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers form specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR® Greene I, is an example of an intercalating dye, that preferentially binds to dsDNA resulting in a concomitant increase in the fluorescent signal. Sequence specific probes, such as used with TaqMan® technology, consist of a fluorochrome and a quenching molecule covalently bound to opposite ends of an oligonucleotide. The probe is designed to selectively bind the target DNA sequence between the two primers. When the DNA strands are synthesized during the PCR reaction, the fluorochrome is cleaved from the probe by the exonuclease activity of the polymerase resulting in signal dequenching. The probe signaling method can be more specific than the intercalating dye method, but in each case, signal strength is proportional to the dsDNA product produced. Each type of quantification method can be used in multi-well liquid phase arrays with each well representing primers and/or probes specific to nucleic acid sequences of interest. When used with messenger RNA preparations of tissues or cell lines, and an array of probe/primer reactions can simultaneously quantify the expression of multiple gene products of interest. See Germer, S., et al., Genome Res. 10:258-266 (2000); Heid, C. A., et al., Genome Res. 6, 986-994 (1996).

In a preferred embodiment, CA nucleic acids encoding CA proteins are used to make a variety of expression vectors to express CA proteins which can then be used in screening assays, as described below. The expression vectors may be either self-replicating extrachromosomal vectors or vectors which integrate into a host genome. Generally, these expression vectors include transcriptional and translational regulatory nucleic acid operably linked to the nucleic acid encoding the CA protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the CA protein; for example, transcriptional and translational regulatory nucleic acid sequences from *Bacillus* are preferably used to express the CA protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The CA proteins of the present invention are produced by culturing a host cell transformed with an expression vector containing nucleic acid encoding an CA protein, under the appropriate conditions to induce or cause expression of the CA protein. The conditions appropriate for CA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect, plant and animal cells, including mammalian cells. Of particular interest are *Drosophila melanogaster* cells, *Saccharomyces cerevisiae* and other yeasts, *E. coli, Bacillus subtilis*, Sf9 cells, C129 cells, 293 cells, *Neurospora*, BHK, CHO, COS, HeLa cells, THP1 cell line (a macrophage cell line) and human cells and cell lines.

In a preferred embodiment, the CA proteins are expressed in mammalian cells. Mammalian expression systems are also known in the art, and include retroviral systems. A preferred expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, CA proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the CA protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, CA proteins are produced in insect cells. Expression vectors for the transformation of insect cells, and in particular, baculovirus-based expression vectors, are well known in the art.

In a preferred embodiment, CA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica.*

The CA protein may also be made as a fusion protein, using techniques well known in the art. Thus, for example, for the creation of monoclonal antibodies. If the desired epitope is small, the CA protein may be fused to a carrier protein to form an immunogen. Alternatively, the CA protein may be made as a fusion protein to increase expression, or for other reasons. For example, when the CA protein is an CA peptide, the nucleic acid encoding the peptide may be linked to other nucleic acid for expression purposes.

In one embodiment, the CA nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the CA nucleic acids, proteins and antibodies at any position. For example, the label should be capable of producing, either directly or indirectly, a detectable signal. The detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

Accordingly, the present invention also provides CA protein sequences. An CA protein of the present invention may be identified in several ways. "Protein" in this sense includes proteins, polypeptides, and peptides. As will be appreciated by those in the art, the nucleic acid sequences of the invention can be used to generate protein sequences. There are a variety of ways to do this, including cloning the entire gene and verifying its frame and amino acid sequence, or by comparing it to known sequences to search for homology to provide a frame, assuming the CA protein has homology to some protein in the database being used. Generally, the nucleic acid sequences are input into a program that will search all three frames for homology. This is done in a preferred embodiment using the following NCBI Advanced BLAST parameters. The program is blastx or blastn. The database is nr. The input data is as "Sequence in FASTA format". The organism list is "none". The "expect" is 10; the filter is default. The "descriptions" is 500, the "alignments" is 500, and the "alignment view" is pairwise. The "query Genetic Codes" is standard (1). The matrix is BLOSUM62; gap existence cost is 11, per residue gap cost is 1; and the lambda ratio is 0.85 default. This results in the generation of a putative protein sequence.

Also included within one embodiment of CA proteins are amino acid variants of the naturally occurring sequences, as determined herein. Preferably, the variants are preferably greater than about 75% homologous to the wild-type sequence, more preferably greater than about 80%, even more preferably greater than about 85% and most preferably greater than 90%. In some embodiments the homology will be as high as about 93 to 95 or 98%. As for nucleic acids, homology in this context means sequence similarity or identity, with identity being preferred. This homology will be determined using standard techniques known in the art as are outlined above for the nucleic acid homologies.

CA proteins of the present invention may be shorter or longer than the wild type amino acid sequences. Thus, in a preferred embodiment, included within the definition of CA proteins are portions or fragments of the wild type sequences herein. In addition, as outlined above, the CA nucleic acids of the invention may be used to obtain additional coding regions, and thus additional protein sequence, using techniques known in the art.

In a preferred embodiment, the CA proteins are derivative or variant CA proteins as compared to the wild-type sequence. That is, as outlined more fully below, the derivative CA peptide will contain at least one amino acid substitution, deletion or insertion, with amino acid substitutions being particularly preferred. The amino acid substitution, insertion or deletion may occur at any residue within the CA peptide.

Also included in an embodiment of CA proteins of the present invention are amino acid sequence variants. These variants fall into one or more of three classes: substitutional, insertional or deletional variants. These variants ordinarily are prepared by site specific mutagenesis of nucleotides in the DNA encoding the CA protein, using cassette or PCR mutagenesis or other techniques well known in the art, to produce DNA encoding the variant, and thereafter expressing the DNA in recombinant cell culture as outlined above. However, variant CA protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the CA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed CA variants screened for the optimal combination of desired activity. Techniques for making substitution mutations at predetermined sites in DNA having a known sequence are well known, for example, M13 primer mutagenesis and LAR mutagenesis. Screening of the mutants is done using assays of CA protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the CA protein are desired, substitutions are generally made in accordance with the following chart:

Chart I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the CA proteins as needed. Alternatively, the variant may be designed such that the biological activity of the CA protein is altered. For example, glycosylation sites may be altered or removed, dominant negative mutations created, etc.

Covalent modifications of CA polypeptides are included within the scope of this invention, for example for use in screening. One type of covalent modification includes reacting targeted amino acid residues of an CA polypeptide with an organic derivatizing agent that is capable of reacting with selected side chains or the N- or C-terminal residues of an CA polypeptide. Derivatization with bifunctional agents is useful, for instance, for crosslinking CA polypeptides to a water-insoluble support matrix or surface for use in the method for purifying anti-CA antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the a-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the CA polypeptide included within the scope of this invention comprises altering the native glycosylation pattern of the polypeptide. "Altering the native glycosylation pattern" is intended for purposes herein to mean deleting one or more carbohydrate moieties found in native sequence CA polypeptide, and/or adding one or more glycosylation sites that are not present in the native sequence CA polypeptide.

Addition of glycosylation sites to CA polypeptides may be accomplished by altering the amino acid sequence thereof. The alteration may be made, for example, by the addition of, or substitution by, one or more serine or threonine residues to the native sequence CA polypeptide (for O-linked glycosylation sites). The CA amino acid sequence may optionally be altered through changes at the DNA level, particularly by mutating the DNA encoding the CA polypeptide at preselected bases such that codons are generated that will translate into the desired amino acids.

Another means of increasing the number of carbohydrate moieties on the CA polypeptide is by chemical or enzymatic coupling of glycosides to the polypeptide. Such methods are described in the art, e.g., in WO 87/05330 published 11 Sep. 1987, and in Aplin and Wriston, LA Crit. Rev. Biochem., pp. 259-306 (1981).

Removal of carbohydrate moieties present on the CA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of CA comprises linking the CA polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

CA polypeptides of the present invention may also be modified in a way to form chimeric molecules comprising an CA polypeptide fused to another, heterologous polypeptide or amino acid sequence. In one embodiment, such a chimeric molecule comprises a fusion of an CA polypeptide with a tag polypeptide which provides an epitope to which an anti-tag antibody can selectively bind. The epitope tag is generally placed at the amino- or carboxyl-terminus of the CA polypeptide, although internal fusions may also be tolerated in some instances. The presence of such epitope-tagged forms of an CA polypeptide can be detected using an antibody against the tag polypeptide. Also, provision of the epitope tag enables the CA polypeptide to be readily purified by affinity purification using an anti-tag antibody or another type of affinity matrix that binds to the epitope tag. In an alternative embodiment, the chimeric molecule may comprise a fusion of an CA polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)].

Also included with the definition of CA protein in one embodiment are other CA proteins of the CA family, and CA proteins from other organisms, which are cloned and expressed as outlined below. Thus, probe or degenerate polymerase chain reaction (PCR) primer sequences may be used to find other related CA proteins from humans or other organisms. As will be appreciated by those in the art, particularly useful probe and/or PCR primer sequences include the unique areas of the CA nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, CA proteins can be made that are longer than those encoded by the nucleic acids of the figures, for example, by the elucidation of additional sequences, the addition of epitope or purification tags, the addition of other fusion sequences, etc.

CA proteins may also be identified as being encoded by CA nucleic acids. Thus, CA proteins are encoded by nucleic acids that will hybridize to the sequences of the sequence listings, or their complements, as outlined herein.

In a preferred embodiment, the invention provides CA antibodies. In a preferred embodiment, when the CA protein is to be used to generate antibodies, for example for immunotherapy, the CA protein should share at least one epitope or determinant with the full length protein. By "epitope" or "determinant" herein is meant a portion of a protein which will generate and/or bind an antibody or T-cell receptor in the context of MHC. Thus, in most instances, antibodies made to a smaller CA protein will be able to bind to the full length protein. In a preferred embodiment, the epitope is unique; that is, antibodies generated to a unique epitope show little or no cross-reactivity.

In one embodiment, the term "antibody" includes antibody fragments, as are known in the art, including Fab, $Fab_2$, single chain antibodies (Fv for example), chimeric antibodies, etc., either produced by the modification of whole antibodies or those synthesized de novo using recombinant DNA technologies.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of Table 1, or fragment thereof or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens. In the present case, one of the binding specificities is for a protein encoded by a nucleic acid of Table 1, or a fragment thereof, the other one is for any other antigen, and preferably for a cell-surface protein or receptor or receptor subunit, preferably one that is tumor specific.

In a preferred embodiment, the antibodies to CA are capable of reducing or eliminating the biological function of CA, as is described below. That is, the addition of anti-CA antibodies (either polyclonal or preferably monoclonal) to CA (or cells containing CA) may reduce or eliminate the CA activity. Generally, at least a 25% decrease in activity is preferred, with at least about 50% being particularly preferred and about a 95-100% decrease being especially preferred.

In a preferred embodiment the antibodies to the CA proteins are humanized antibodies. Humanized forms of non-human (e.g., murine) antibodies are chimeric molecules of immunoglobulins, immunoglobulin chains or fragments thereof (such as Fv, Fab, Fab', $F(ab')_2$ or other antigen binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework residues (FR) regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies [Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

By immunotherapy is meant treatment of a carcinoma with an antibody raised against an CA protein. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen.

In a preferred embodiment, oncogenes which encode secreted growth factors may be inhibited by raising antibodies against CA proteins that are secreted proteins as described above. Without being bound by theory, antibodies used for treatment, bind and prevent the secreted protein from binding to its receptor, thereby inactivating the secreted CA protein.

In another preferred embodiment, the CA protein to which antibodies are raised is a transmembrane protein. Without being bound by theory, antibodies used for treatment, bind the extracellular domain of the CA protein and prevent it from binding to other proteins, such as circulating ligands or cell-associated molecules. The antibody may cause down-regulation of the transmembrane CA protein. As will be appreciated by one of ordinary skill in the art, the antibody may be a competitive, non-competitive or uncompetitive inhibitor of protein binding to the extracellular domain of the CA protein. The antibody is also an antagonist of the CA protein. Further, the antibody prevents activation of the transmembrane CA protein. In one aspect, when the antibody prevents the binding of other molecules to the CA protein, the antibody prevents growth of the cell. The antibody may also sensitize the cell to cytotoxic agents, including, but not limited to TNF-$\alpha$, TNF-$\beta$, IL-1, INF-$\gamma$ and IL-2, or chemotherapeutic agents including 5FU, vinblastine, actinomycin D, cisplatin, methotrexate, and the like. In some instances the antibody belongs to a sub-type that activates serum complement when complexed with the transmembrane protein thereby mediating cytotoxicity. Thus, carcinomas may be treated by administering to a patient antibodies directed against the transmembrane CA protein.

In another preferred embodiment, the antibody is conjugated to a therapeutic moiety. In one aspect the therapeutic moiety is a small molecule that modulates the activity of the CA protein. In another aspect the therapeutic moiety modulates the activity of molecules associated with or in close proximity to the CA protein. The therapeutic moiety may inhibit enzymatic activity such as protease or protein kinase activity associated with carcinoma.

In a preferred embodiment, the therapeutic moiety may also be a cytotoxic agent. In this method, targeting the cytotoxic agent to tumor tissue or cells, results in a reduction in the number of afflicted cells, thereby reducing symptoms associated with carcinomas, including lymphoma or breast cancer.

Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against CA proteins, or binding of a radionuclide to a chelating agent that has been covalently attached to the antibody. Targeting the therapeutic moiety to transmembrane CA proteins not only serves to increase the local concentration of therapeutic moiety in the carcinoma of interest, i.e., lymphoma or breast cancer, but also serves to reduce deleterious side effects that may be associated with the therapeutic moiety.

In another preferred embodiment, the CA protein against which the antibodies are raised is an intracellular protein. In this case, the antibody may be conjugated to a protein which facilitates entry into the cell. In one case, the antibody enters the cell by endocytosis. In another embodiment, a nucleic acid encoding the antibody is administered to the individual or cell. Moreover, wherein the CA protein can be targeted within a cell, i.e., the nucleus, an antibody thereto contains a signal for that target localization, i.e., a nuclear localization signal.

The CA antibodies of the invention specifically bind to CA proteins. By "specifically bind" herein is meant that the antibodies bind to the protein with a binding constant in the range of at least $10^{-4}$-$10^{-6}$ $M^{-1}$, with a preferred range being $10^{-7}$-$10^{-9}$ $M^{-1}$.

In a preferred embodiment, the CA protein is purified or isolated after expression. CA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the CA protein may be purified using a standard anti-CA antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the CA protein. In some instances no purification will be necessary.

Once expressed and purified if necessary, the CA proteins and nucleic acids are useful in a number of applications.

In one aspect, the expression levels of genes are determined for different cellular states in the carcinoma phenotype; that is, the expression levels of genes in normal tissue and in carcinoma tissue (and in some cases, for varying severities of lymphoma or breast cancer that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or carcinoma tissue.

"Differential expression," or grammatical equivalents as used herein, refers to both qualitative as well as quantitative differences in the genes temporal and/or cellular expression patterns within and among the cells. Thus, a differentially expressed gene can qualitatively have its expression altered, including an activation or inactivation, in, for example, normal versus carcinoma tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip® expression arrays, Lockhart, Nature Biotechnology, 14:1675-1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the CA protein and standard immunoassays (ELISAs, etc.) or other techniques, including mass spectroscopy assays, 2D gel electrophoresis assays, etc. Thus, the proteins corresponding to CA genes, i.e. those identified as being important in a particular carcinoma phenotype, i.e., breast cancer or lymphoma, can be evaluated in a diagnostic test specific for that carcinoma.

In a preferred embodiment, gene expression monitoring is done and a number of genes, i.e. an expression profile, is monitored simultaneously, although multiple protein expression monitoring can be done as well. Similarly, these assays may be done on an individual basis as well.

In this embodiment, the CA nucleic acid probes may be attached to biochips as outlined herein for the detection and quantification of CA sequences in a particular cell. The assays are done as is known in the art. As will be appreciated by those in the art, any number of different CA sequences may be used as probes, with single sequence assays being used in some cases, and a plurality of the sequences described herein being used in other embodiments. In addition, while solid-phase assays are described, any number of solution based assays may be done as well.

In a preferred embodiment, both solid and solution based assays may be used to detect CA sequences that are upregulated or down-regulated in carcinomas as compared to normal tissue. In instances where the CA sequence has been altered but shows the same expression profile or an altered expression profile, the protein will be detected as outlined herein.

In a preferred embodiment nucleic acids encoding the CA protein are detected. Although DNA or RNA encoding the CA protein may be detected, of particular interest are methods wherein the mRNA encoding a CA protein is detected. The presence of mRNA in a sample is an indication that the CA gene, such as KCNJ9 has been transcribed to form the mRNA, and suggests that the protein is expressed. Probes to detect the mRNA can be any nucleotide/deoxynucleotide probe that is complementary to and base pairs with the mRNA and includes but is not limited to oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a CA protein is detected by binding the digoxygenin with an anti-digoxygenin secondary antibody and developed with nitro blue tetrazolium and 5-bromo-4-chloro-3-indoyl phosphate.

In a preferred embodiment, any of the three classes of proteins as described herein (secreted, transmembrane or intracellular proteins) are used in diagnostic assays. The CA proteins, antibodies, nucleic acids, modified proteins and cells containing CA sequences are used in diagnostic assays. This can be done on an individual gene or corresponding polypeptide level, or as sets of assays.

As described and defined herein, CA proteins find use as markers of carcinomas, including breast cancer or lymphomas such as, but not limited to, Hodgkin's and non-Hodgkin lymphoma. Detection of these proteins in putative carcinoma tissue or patients allows for a determination or diagnosis of the type of carcinoma. Numerous methods known to those of ordinary skill in the art find use in detecting carcinomas. In one embodiment, antibodies are used to detect CA proteins. A preferred method separates proteins from a sample or patient by electrophoresis on a gel (typically a denaturing and reducing protein gel, but may be any other type of gel including isoelectric focusing gels and the like). Following separation of proteins, the CA protein is detected by immunoblotting with antibodies raised against the CA protein. Methods of immunoblotting are well known to those of ordinary skill in the art.

In another preferred method, antibodies to the CA protein find use in in situ imaging techniques. In this method cells are contacted with from one to many antibodies to the CA protein(s). Following washing to remove non-specific antibody binding, the presence of the antibody or antibodies is detected. In one embodiment the antibody is detected by incubating with a secondary antibody that contains a detectable label. In another method the primary antibody to the CA protein(s) contains a detectable label. In another preferred embodiment each one of multiple primary antibodies contains a distinct and detectable label. This method finds particular use in simultaneous screening for a plurality of CA proteins. As will be appreciated by one of ordinary skill in the art, numerous other histological imaging techniques are useful in the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing carcinomas from blood samples. As previously described, certain CA proteins are secreted/circulating molecules. Blood samples, therefore, are useful as samples to be probed or tested for the presence of secreted CA proteins. Antibodies can be used to detect the CA proteins by any of the previously described immunoassay techniques including ELISA, immunoblotting (Western blotting), immunoprecipitation, BIACORE technology and the like, as will be appreciated by one of ordinary skill in the art.

In a preferred embodiment, in situ hybridization of labeled CA nucleic acid probes to tissue arrays is done. For example, arrays of tissue samples, including CA tissue and/or normal tissue, are made. In situ hybridization as is known in the art can then be done.

It is understood that when comparing the expression fingerprints between an individual and a standard, the skilled artisan can make a diagnosis as well as a prognosis. It is further understood that the genes which indicate the diagnosis may differ from those which indicate the prognosis.

In a preferred embodiment, the CA proteins, antibodies, nucleic acids, modified proteins and cells containing CA sequences are used in prognosis assays. As above, gene expression profiles can be generated that correlate to carcinoma, especially breast cancer or lymphoma, severity, in terms of long term prognosis. Again, this may be done on either a protein or gene level, with the use of genes being preferred. As above, the CA probes are attached to biochips for the detection and quantification of CA sequences in a tissue or patient. The assays proceed as outlined for diagnosis.

In a preferred embodiment, any of the CA sequences as described herein are used in drug screening assays. The CA proteins, antibodies, nucleic acids, modified proteins and cells containing CA sequences are used in drug screening assays or by evaluating the effect of drug candidates on a "gene expression profile" or expression profile of polypeptides. In one embodiment, the expression profiles are used, preferably in conjunction with high throughput screening techniques to allow monitoring for expression profile genes after treatment with a candidate agent, Zlokarnik, et al., Science 279, 84-8 (1998), Heid, et al., Genome Res., 6:986-994 (1996).

In a preferred embodiment, the CA proteins, antibodies, nucleic acids, modified proteins and cells containing the native or modified CA proteins are used in screening assays. That is, the present invention provides novel methods for screening for compositions which modulate the carcinoma phenotype. As above, this can be done by screening for modulators of gene expression or for modulators of protein activity. Similarly, this may be done on an individual gene or protein level or by evaluating the effect of drug candidates on a "gene expression profile". In a preferred embodiment, the expression profiles are used, preferably in conjunction with high throughput screening techniques to allow monitoring for expression profile genes after treatment with a candidate agent, see Zlokarnik, supra.

Having identified the CA genes herein, a variety of assays to evaluate the effects of agents on gene expression may be executed. In a preferred embodiment, assays may be run on an individual gene or protein level. That is, having identified a particular gene as aberrantly regulated in carcinoma, candidate bioactive agents may be screened to modulate the genes response. "Modulation" thus includes both an increase and a decrease in gene expression or activity. The preferred amount of modulation will depend on the original change of the gene expression in normal versus tumor tissue, with changes of at least 10%, preferably 50%, more preferably 100-300%, and in some embodiments 300-1000% or greater. Thus, if a gene exhibits a 4 fold increase in tumor compared to normal tissue, a decrease of about four fold is desired; a 10 fold decrease in tumor compared to normal tissue gives a 10 fold increase in expression for a candidate agent is desired, etc. Alternatively, where the CA sequence has been altered but shows the same expression profile or an altered expression profile, the protein will be detected as outlined herein.

As will be appreciated by those in the art, this may be done by evaluation at either the gene or the protein level; that is, the amount of gene expression may be monitored using nucleic acid probes and the quantification of gene expression levels, or, alternatively, the level of the gene product itself can be monitored, for example through the use of antibodies to the CA protein and standard immunoassays. Alternatively, binding and bioactivity assays with the protein may be done as outlined below.

In a preferred embodiment, gene expression monitoring is done and a number of genes, i.e. an expression profile, is monitored simultaneously, although multiple protein expression monitoring can be done as well.

In this embodiment, the CA nucleic acid probes are attached to biochips as outlined herein for the detection and quantification of CA sequences in a particular cell. The assays are further described below.

Generally, in a preferred embodiment, a candidate bioactive agent is added to the cells prior to analysis. Moreover, screens are provided to identify a candidate bioactive agent which modulates a particular type of carcinoma, modulates CA proteins, binds to a CA protein, or interferes between the binding of a CA protein and an antibody.

The term "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the carcinoma phenotype, binding to and/or modulating the bioactivity of an CA protein, or the expression of a CA sequence, including both nucleic acid sequences and protein sequences. In a particularly preferred embodiment, the candidate agent suppresses a CA phenotype, for example to a normal tissue fingerprint. Similarly, the candidate agent preferably suppresses a severe CA phenotype. Generally a plurality of assay mixtures are run in parallel with different agent concentrations to obtain a differential response to the various concentrations. Typically, one of these concentrations serves as a negative control, i.e., at zero concentration or below the level of detection.

In one aspect, a candidate agent will neutralize the effect of an CA protein. By "neutralize" is meant that activity of a protein is either inhibited or counter acted against so as to have substantially no effect on a cell.

Candidate agents encompass numerous chemical classes, though typically they are organic or inorganic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids, as defined above.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In assays for altering the expression profile of one or more CA genes, after the candidate agent has been added and the cells allowed to incubate for some period of time, the sample containing the target sequences to be analyzed is added to the biochip. If required, the target sequence is prepared using known techniques. For example, the sample may be treated to lyse the cells, using known lysis buffers, electroporation, etc., with purification and/or amplification such as PCR occurring as needed, as will be appreciated by those in the art. For example, an in vitro transcription with labels covalently attached to the nucleosides is done. Generally, the nucleic acids are labeled with a label as defined herein, with biotin-FITC or PE, cy3 and cy5 being particularly preferred.

In a preferred embodiment, the target sequence is labeled with, for example, a fluorescent, chemiluminescent, chemical, or radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data is analyzed to determine the expression levels, and changes in expression levels as between states, of individual genes, forming a gene expression profile.

In a preferred embodiment, as for the diagnosis and prognosis applications, having identified the differentially expressed gene(s) or mutated gene(s) important in any one state, screens can be run to alter the expression of the genes individually. That is, screening for modulation of regulation of expression of a single gene can be done. Thus, for example, particularly in the case of target genes whose presence or absence is unique between two states, screening is done for modulators of the target gene expression.

In addition, screens can be done for novel genes that are induced in response to a candidate agent. After identifying a candidate agent based upon its ability to suppress a CA expression pattern leading to a normal expression pattern, or modulate a single CA gene expression profile so as to mimic the expression of the gene from normal tissue, a screen as described above can be performed to identify genes that are specifically modulated in response to the agent. Comparing expression profiles between normal tissue and agent treated CA tissue reveals genes that are not expressed in normal tissue or CA tissue, but are expressed in agent treated tissue. These agent specific sequences can be identified and used by any of the methods described herein for CA genes or proteins. In particular these sequences and the proteins they encode find use in marking or identifying agent treated cells. In addition, antibodies can be raised against the agent induced proteins and used to target novel therapeutics to the treated CA tissue sample.

Thus, in one embodiment, a candidate agent is administered to a population of CA cells, that thus has an associated CA expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, CA tissue may be screened for agents that reduce or suppress the CA phenotype. A change in at least one gene of the expression profile indicates that the agent has an effect on CA activity. By defining such a signature for the CA phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins).

That is, having identified a particular differentially expressed gene as important in a particular state, screening of modulators of either the expression of the gene or the gene product itself can be done. The gene products of differentially expressed genes are sometimes referred to herein as "CA proteins" or an "CAP". The CAP may be a fragment, or alternatively, be the full length protein to the fragment encoded by the nucleic acids of Table 1. Preferably, the CAP is a fragment. In another embodiment, the sequences are sequence variants as further described herein.

Preferably, the CAP is a fragment of approximately 14 to 24 amino acids long. More preferably the fragment is a soluble fragment. Preferably, the fragment includes a non-transmembrane region. In a preferred embodiment, the fragment has an N-terminal Cys to aid in solubility. In one embodiment, the c-terminus of the fragment is kept as a free acid and the n-terminus is a free amine to aid in coupling, i.e., to cysteine.

In one embodiment the CA proteins are conjugated to an immunogenic agent as discussed herein. In one embodiment the CA protein is conjugated to BSA.

In a preferred embodiment, screening is done to alter the biological function of the expression product of the CA gene, such as KCNJ9. Again, having identified the importance of a gene in a particular state, screening for agents that bind and/or modulate the biological activity of the gene product can be run as is more fully outlined below.

In a preferred embodiment, screens are designed to first find candidate agents that can bind to CA proteins, and then these agents may be used in assays that evaluate the ability of the candidate agent to modulate the CAP activity and the carcinoma phenotype. Thus, as will be appreciated by those in the art, there are a number of different assays which may be run; binding assays and activity assays.

In a preferred embodiment, binding assays are done. In general, purified or isolated gene product is used; that is, the gene products of one or more CA nucleic acids are made. In general, this is done as is known in the art. For example, antibodies are generated to the protein gene products, and standard immunoassays are run to determine the amount of protein present. Alternatively, cells comprising the CA proteins can be used in the assays.

Thus, in a preferred embodiment, the methods comprise combining a CA protein and a candidate bioactive agent, and determining the binding of the candidate agent to the CA protein. Preferred embodiments utilize the human or mouse CA protein, although other mammalian proteins may also be used, for example for the development of animal models of human disease. In some embodiments, as outlined herein, variant or derivative CA proteins may be used.

Generally, in a preferred embodiment of the methods herein, the CA protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the CA protein is bound to the support, and a candidate bioactive agent is added to the assay. Alternatively, the candidate agent is bound to the support and the CA protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the CA protein may be done in a number of ways. In a preferred embodiment, the candidate bioactive agent is labeled, and binding determined directly. For example, this may be done by attaching all or a portion of the CA protein to a solid support, adding a labeled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, is for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. CA protein), such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the CA protein and thus is capable of binding to, and potentially modulating, the activity of the CA protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the CA protein with a higher affinity. Thus, if the candidate bioactive agent is labeled, the presence of the label on the support, coupled with a lack of competitor binding, may indicate that the candidate agent is capable of binding to the CA protein.

In a preferred embodiment, the methods comprise differential screening to identity bioactive agents that are capable of modulating the activity of the CA proteins. In this embodiment, the methods comprise combining a CA protein and a competitor in a first sample. A second sample comprises a candidate bioactive agent, a CA protein and a competitor. The binding of the competitor is determined for both samples, and a change, or difference in binding between the two samples indicates the presence of an agent capable of binding to the CA protein and potentially modulating its activity. That is, if the binding of the competitor is different in the second sample relative to the first sample, the agent is capable of binding to the CA protein.

Alternatively, a preferred embodiment utilizes differential screening to identify drug candidates that bind to the native CA protein, but cannot bind to modified CA proteins. The structure of the CA protein may be modeled, and used in rational drug design to synthesize agents that interact with that site. Drug candidates that affect CA bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of CA proteins may also be done. In a preferred embodiment, methods for screening for a bioactive agent capable of modulating the activity of CA proteins comprise the steps of adding a candidate bioactive agent to a sample of CA proteins, as above, and determining an alteration in the biological activity of CA proteins. "Modulating the activity of an CA protein" includes an increase in activity, a decrease in activity, or a change in the type or kind of activity present. Thus, in this embodiment, the candidate agent should both bind to CA proteins (although this may not be necessary), and alter its biological or biochemical activity as defined herein. The methods include both in vitro screening methods, as are generally outlined above, and in vivo screening of cells for alterations in the presence, distribution, activity or amount of CA proteins.

Thus, in this embodiment, the methods comprise combining a CA sample and a candidate bioactive agent, and evaluating the effect on CA activity. By "CA activity" or grammatical equivalents herein is meant one of the CA protein's biological activities, including, but not limited to, its role in tumorigenesis, including cell division, preferably in lymphatic tissue, cell proliferation, tumor growth and transformation of cells. In one embodiment, CA activity includes activation of or by a protein encoded by a nucleic acid of Table 1. An inhibitor of CA activity is the inhibition of any one or more CA activities.

In a preferred embodiment, the activity of the CA protein is increased; in another preferred embodiment, the activity of the CA protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of a CA protein. The methods comprise adding a candidate bioactive agent, as defined above, to a cell comprising CA proteins. Preferred cell types include almost any cell. The cells contain a recombinant nucleic acid that encodes a CA protein. In a preferred embodiment, a library of candidate agents are tested on a plurality of cells.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

In this way, bioactive agents are identified. Compounds with pharmacological activity are able to enhance or interfere with the activity of the CA protein.

In one embodiment, a method of inhibiting carcinoma cancer cell division, is provided. The method comprises administration of a carcinoma cancer inhibitor.

In a preferred embodiment, a method of inhibiting lymphoma carcinoma cell division is provided comprising administration of a lymphoma carcinoma inhibitor.

In a preferred embodiment, a method of inhibiting breast cancer carcinoma cell division is provided comprising administration of a breast cancer carcinoma inhibitor.

In another embodiment, a method of inhibiting tumor growth is provided. The method comprises administration of a carcinoma cancer inhibitor. In a particularly preferred embodiment, a method of inhibiting tumor growth in lymphatic tissue is provided comprising administration of a lymphoma inhibitor.

In another embodiment, a method of inhibiting tumor growth is provided. The method comprises administration of a carcinoma cancer inhibitor. In a particularly preferred embodiment, a method of inhibiting tumor growth in mammary tissue is provided comprising administration of a breast cancer inhibitor.

In a further embodiment, methods of treating cells or individuals with cancer are provided. The method comprises administration of a carcinoma cancer inhibitor. In one embodiment the carcinoma is a breast cancer carcinoma. In an alternative embodiment, the carcinoma is a lymphoma carcinoma.

In one embodiment, a carcinoma cancer inhibitor is an antibody as discussed above. In another embodiment, the carcinoma cancer inhibitor is an antisense molecule. Antisense molecules as used herein include antisense or sense oligonucleotides comprising a singe-stranded nucleic acid sequence (either RNA or DNA) capable of binding to target mRNA (sense) or DNA (antisense) sequences for carcinoma cancer molecules. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment.

The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1-100% wgt/vol. The agents may be administered alone or in combination with other treatments, i.e., radiation.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that the various CA sequences are important in carcinomas. Accordingly, disorders based on mutant or variant CA genes may be determined. In one embodiment, the invention provides methods for identifying cells containing variant CA genes comprising determining all or part of the sequence of at least one endogenous CA genes in a cell. As will be appreciated by those in the art, this may be done using any number of sequencing techniques. In a preferred embodiment, the invention provides methods of identifying the CA genotype of an individual comprising determining all or part of the sequence of at least one CA gene, such as KCNJ9 of the individual. This is generally done in at least one tissue of the individual, and may include the evaluation of a number of tissues or different samples of the same tissue. The method may include comparing the sequence of the sequenced CA gene to a known CA gene, such as KCNJ9, i.e., a wild-type gene. As will be appreciated by those in the art, alterations in the sequence of some oncogenes can be an indication of either the presence of the disease, or propensity to develop the disease, or prognosis evaluations.

The sequence of all or part of the CA gene, such as KCNJ9, can then be compared to the sequence of a known CA gene to determine if any differences exist. This can be done using any number of known homology programs, such as Bestfit, etc. In a preferred embodiment, the presence of a difference in the sequence between the CA gene, such as KCNJ9 of the patient and the known CA gene is indicative of a disease state or a propensity for a disease state, as outlined herein.

In a preferred embodiment, the CA genes are used as probes to determine the number of copies of the CA gene, such as KCNJ9 in the genome. For example, some cancers exhibit chromosomal deletions or insertions, resulting in an alteration in the copy number of a gene.

In another preferred embodiment CA genes are used as probes to determine the chromosomal location of the CA genes. Information such as chromosomal location finds use in providing a diagnosis or prognosis in particular when chromosomal abnormalities such as translocations, and the like are identified in CA gene, such as KCNJ9, loci.

Thus, in one embodiment, methods of modulating CA in cells or organisms are provided. In one embodiment, the methods comprise administering to a cell an anti-CA antibody that reduces or eliminates the biological activity of an endogenous CA protein. Alternatively, the methods comprise administering to a cell or organism a recombinant nucleic acid encoding a CA protein. As will be appreciated by those in the art, this may be accomplished in any number of ways. In a preferred embodiment, for example when the CA sequence is down-regulated in carcinoma, the activity of the CA gene is increased by increasing the amount of CA in the cell, for example by overexpressing the endogenous CA or by administering a gene encoding the CA sequence, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, for example when the CA sequence is up-regulated in carcinoma, the activity of the endogenous CA gene is decreased, for example by the administration of a CA antisense nucleic acid.

In one embodiment, the CA proteins of the present invention may be used to generate polyclonal and monoclonal antibodies to CA proteins, which are useful as described herein. Similarly, the CA proteins can be coupled, using standard technology, to affinity chromatography columns. These columns may then be used to purify CA antibodies. In a preferred embodiment, the antibodies are generated to epitopes unique to a CA protein; that is, the antibodies show little or no cross-reactivity to other proteins. These antibodies find use in a number of applications. For example, the CA antibodies may be coupled to standard affinity chromatography columns and used to purify CA proteins. The antibodies may also be used as blocking polypeptides, as outlined above, since they will specifically bind to the CA protein.

In one embodiment, a therapeutically effective dose of a CA or modulator thereof is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for CA degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the CA proteins and modulators of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the CA proteins and modulators may be directly applied as a solution or spray.

The pharmaceutical compositions of the present invention comprise a CA protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In a preferred embodiment, CA proteins and modulators are administered as therapeutic agents, and can be formulated as outlined above. Similarly, CA genes (including both the full-length sequence, partial sequences, or regulatory sequences of the CA coding regions) can be administered in gene therapy applications, as is known in the art. These CA genes can include antisense applications, either as gene therapy (i.e. for incorporation into the genome) or as antisense compositions, as will be appreciated by those in the art.

In a preferred embodiment, CA genes, such as KCNJ9, are administered as DNA vaccines, either single genes or combinations of CA genes. Naked DNA vaccines are generally known in the art. Brower, Nature Biotechnology, 16:1304-1305 (1998).

In one embodiment, CA genes of the present invention are used as DNA vaccines. Methods for the use of genes as DNA vaccines are well known to one of ordinary skill in the art, and include placing a CA gene or portion of a CA gene under the control of a promoter for expression in a patient with carcinoma. The CA gene used for DNA vaccines can encode full-length CA proteins, but more preferably encodes portions of the CA proteins including peptides derived from the CA protein. In a preferred embodiment a patient is immunized with a DNA vaccine comprising a plurality of nucleotide sequences derived from a CA gene. Similarly, it is possible to immunize a patient with a plurality of CA genes or portions thereof as defined herein. Without being bound by theory, expression of the polypeptide encoded by the DNA vaccine, cytotoxic T-cells, helper T-cells and antibodies are induced which recognize and destroy or eliminate cells expressing CA proteins.

In a preferred embodiment, the DNA vaccines include a gene encoding an adjuvant molecule with the DNA vaccine. Such adjuvant molecules include cytokines that increase the immunogenic response to the CA polypeptide encoded by the DNA vaccine. Additional or alternative adjuvants are known to those of ordinary skill in the art and find use in the invention.

In another preferred embodiment CA genes find use in generating animal models of carcinomas, particularly breast cancer or lymphoma carcinomas. As is appreciated by one of ordinary skill in the art, when the CA gene identified is repressed or diminished in CA tissue, gene therapy technology wherein antisense RNA directed to the CA gene will also diminish or repress expression of the gene. An animal generated as such serves as an animal model of CA that finds use in screening bioactive drug candidates. Similarly, gene knockout technology, for example as a result of homologous recombination with an appropriate gene targeting vector, will result in the absence of the CA protein. When desired, tissue-specific expression or knockout of the CA protein may be necessary.

It is also possible that the CA protein is overexpressed in carcinoma. As such, transgenic animals can be generated that overexpress the CA protein. Depending on the desired expression level, promoters of various strengths can be employed to express the transgene. Also, the number of copies of the integrated transgene can be determined and compared for a determination of the expression level of the transgene. Animals generated by such methods find use as animal models of CA and are additionally useful in screening for bioactive molecules to treat carcinoma.

The CA nucleic acid sequences of the invention are depicted in Table 1. The sequences in each Table include genomic sequence, mRNA and coding sequences for both mouse and human. N/A indicates a gene that has been identified, but for which there has not been a name ascribed. The different sequences are assigned the following SEQ ID Nos:

TABLE 1

| (mouse gene: mCG2257; human gene KCNJ9)<br>Mouse genomic sequence (SEQ ID NO: 1)<br>Mouse mRNA sequence (SEQ ID NO: 2)<br>Mouse coding sequence (SEQ ID NO: 3)<br>Human genomic sequence (SEQ ID NO: 4)<br>Human mRNA sequence (SEQ ID NO: 5)<br>Human coding sequence (SEQ ID NO: 6) |
|---|

MOUSE NOMENCLATURE
ICS GNM Kcnj9
Celera mCG4483
HUMAN NOMENCLATURE
HGNC KCNJ9
Celera hCG39735
MOUSE SEQUENCE - GENOMIC (SEQ ID NO: 1)

NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNCCTCATGAATGCTGAGACTAAAGGT
GTGCATCACCCCTGCCCAATTTCAAAATAGTGACCCAAGGGAAGACCAGATTACAAGGTGCTGCACTACAAAGTGAGAAAATGTTAACGGTTACCCT
TTAAAAACTTTGCTTAGAGGGAAAAAAAAAAACCCCACAATCATAACCAAAGCAATGGACCAGGAACTATTTTCCTGCCTGTTTTGTCTTTTCAAATT
TCTGTCATCTTCTGCTCCTAGAGAGGAACGGCTACAGTAAGATGGTCTGAAGACCTGGTAGTTTTTTTTTTTTTTTTTTTTTTTTTAAGATTTATTTATT
TATTATATGTAAGTACATGTAAGTAAGTACATTGTAGCTGTCCTCAGATACTCCAGAAGAGGGCATCAGATTTCGTTACGGATGGTTGTGAGCCACC
ATGTGGTTGCTGGGATTTGAACTCGGGACCTTTGGAAAAGCAGTCGGTGCTCTTAACCACTGAGCCATCTCGCCAGCCCAGACCTGGTAGTTTAAGC
CTGCAATCTCAGCTGTTTGGGGAGGGGAAGCAGGAGGGTTGCAAGCTCAAAGCCTGAGCTACAGAATGAGTTCAAAGCCAGTGTGAATAACTTAGCA
GGGCTCACAGTCTTGACATTCAGAGATGGGGAAGATTATGGGGCTGAGCTCAGACCACAATATAAAATGAAGAAGGAACACAGAGGAGAGAAGCCAA
GAACTGTCGGGGTTTATGAAATCATTACAAGACACAAGAATTTATTATTTTTCCAGAATTGTTACCCAAGCATTTGGCATCCATCGCCACCTACATG
TCAGTGTCCACCTGGACAGAAATCTCAAACTTAGTCCAGCGTAGAACATCTTACCCACAGGAGCGCTCCTCATGGGACTATGTCACCATCATCCAAC
TAGAAACACAGCAGTCATCTCAGCCTCCTTAGTCTTCCTTACAGCAGCAACTCCATCCTCTAACCAAAGCATCTCCCACTGAGCACGCCCTCCTGCC
CCCCTCTCTCTCTCTCCCTTTATCGCTGCTGCAGTCTACAGCAGATGCACCTCTCAGCAGGGATCCTGGAGCAGCCATCTAGTGCCTTATCCCCTCC
AGTCTTTCTACACTCCAATAATGCTTCAGGTCACTAACTCCTTTATGTAAAAACAATTAAGGCTCAGCAAGATGGCTCAGAGGGGTAAAGGCAACTT
GCTGCCAAACTTGATGACCTGGGGTCAATCTCCAGTACTGATGTGGTAGGAGAGACTCAACTACCAAGAGTTATCCTCTGACCTCTACATGTGTGTT
GTGGTACACCCACAAACACAGAGAGAGAGAGAGAGAGAGAGAGAGAGAGAGACAGACAGACAGACAGACAGACAGACAGACAGAGACACACACAGAG
AGAAATGTAACGTTTAGAGAAGAATCCATCCATATTCTTTAGCACAGAACAGAAGGCACATTAATTATAACCTGGGCATCCTGCCCTGTCTTCCTCA
CATCCAACTCTATAGCTGCTTCCTCCTCTAACACCCAGGGTTGTTAAGTCTTGTGTCCCCTTCTGTATCTTGCTCCTTGTTCTTTGGTCACACAGTG
ACCAAAGTCACTGAGTGTTGTGCAAACCTCTTCTTCTTGACTCCTGTATCTCTCTGGAGCTCTACTTAGGCTCCAGTACCTGCAAGGGATTAATGCC
CTCACATGACAGGCCCCAGACAGAACCCATCCTCTTTCCCTCTCACCAAGGTTGGGAATGCTCACAGCTCCCTGATTTCTGTGTAACTCCTGTCAAG
CAGACTGAAACACCGACATTACATCTTGCTCTTTATGCTTGCCTATGTCCCATTCTGTGTCATGACAATTCAGCCACCAAGTTCTGTTAACTCTCCC
TTGGTTATATTTCTCTAGGATACACATTTTCATTTCTATGGCCAGAATCATAAAATTACCACTAGCCCAGGACCTGACCCATCCCTCACCCCTCTTT
CCAGTATCAAAGGGAGACAAACTGTTTTTATTAAAGATGTACTGTATTTAAAAAAACCTAGAATCAAAACTTTGAACAAAGTGGGGTGTGATGGTAT
ACACCTTTAATCCCAGCACTTGGGAGGCAGAGGCAGGTGGATTTCTGAGTTCAAGGCCAGCCTGGTGTACAAAGTGAGTTCCAGGACAGCCAGGTCT
ACACAGAGAAATCCTGTCTCGAAAAAACCAACCAACCAAATAAATAAATAAATAAATAAATAAATAAATAAATAAATACAAGGTCTCTGGATAAACT
CCTTCCAAATAGAAATGAGAAGCCATCTCGTGAAGCTCAGTGTGAGGGTGAGGTGGCACGAGATGGAACTGGGCAATTGGAAAGAGTTAGGTATTGT
AGAGCCACAGGAGAGCAGGACTGTGGTGACTTCTGTGGCCCTGTGATGTTCTCACTCAAGAGTGACTTACATCAGGATTCCATTCTTAAATAAGCAC
ACTTTATTAGCAACTATAACTCTGTATACATTGTGTTTGCTTTTAATATTTAACTTTTTGTTTTCCAAAAAGAGTTCCTGAAACATACAACAAGCAG
AAATTGTCATTGCTGAAGGATGCTTAGCATGCTCATGTTTCTGAGTGTTTACTAGGCGTGATAAATTTGACTTTTCTTGTTTTCTTTCAGTTCACTC
TGTCTGATGCTCCTGCCCCGGTCTCCTAAATGCAGGGATTATAGGTGTGCACCGCCACACCTAACTGTGTACAGTAGATCGTAAGATGGGAAATCCC

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

AGAGTCAGGGACCTTAGGTGGCTGACCTATACACAGTGACATGCCCAGGAAGTGTTAAATCTGGCATTTGAATCCACCTGTTTGACCCCAGAGTTTG
TCAAAGGGTAATAGTACAGCGCTCTTGCATGACTTAAAGAGATGCTCATTTTCCCAAGAGAACCAAGAGGTTCTAGTGGCCAAATGTCAGTATGAAT
AAATCTGCTGAGATGCGCTGTGCAGCGTCCGTCGACCTTACAGGAGGACAGAGCAATCCTTTTCCTTTTTGATTCATCGCTCCTTTCAGACTTGATC
CTCTCACCACAGATCTCTTTCCTTCCACTTCCTCATTCAAAATGGGGTCAGTTCCCCCTCAGAACAAAAGAGGAACATGAGGCGAAGACCCTTTGCA
GAGGGAAAATCCACAGCTGGGCGTAGGCCGAGGGAGCTTTCGCTGGGAGAAGCAGGTGAGTTCGGATGAAGGGAAGCAACTGAGAGAGGCAAGGCAG
ATCCTCAGACGGGGCGGGTTGGGGGGGGGCGACTCGGAGAGGGAGTTTTCGGGGAGTCATCAGAGCTGGCCAGGAAGAACTAGGCATGAACATGAG
TCCCAGGGACTCCGAGGGACACATTTCTGCTTAGGTCCCACAGTATTAACACGGTCCACTAAAAGCAGATACGCTCAGCAGGATGAGCGGCCACAGA
GGAGAGCCTATCAGTACTCGGTTTAGTCATTACCTTTTAATACACATGATTTATATAAGCCTGTATGTGTATAAGACTTAAGTTATAAATGGCTAAT
TACATTACAGAAGGACTACAGAAGGCAGAGAGAGGGAGGGAGGGGAGGGCAAGGGTGGGGAGGGGAGGGAAAGGAAGATGCTCTTTACCTATAAGGT
TTATCTAGTATCTTTCTAATTGGTCCTTTTAGTGGCAATTCTGTTAACATTCAAATACACCATGGAGAGGGAAGAACAGAAAACCCCCAGATGCCTG
GAACTGGGGAAGCTGTCTTAACCCTGACCTCTCTTGGGATGCTCTTCTCATCTATAAACTAATGATTACTTTAGATCACTTCTGAATGACCATGGTT
AAGTCCTGGTCTAACTCTATCCAGCCCCGTAGACCTGGTAGACAAGATGGACCTGTGCGTAACTCTTCTAGGGCTGATTCCACATGGAATTTACCTA
CTTTTATTTAGAGATGAGGTCTCACTGTGTCCCTCTGGATGAGCTGGAACTCACCACACACACCAGGGTGGCCTCAGACTCAGAGATTTACTTGCCA
GTGCTTCTCAAATGTTGGGGTAAAAAGCGTAAGCCACCACCCACAGACCCCATGAATTCATATCAATTGTTATTTGAACTAACTTGACCTTCCTACT
CCCCTCAGCTCACATCCTCAACCGTCCCTGCCTTCCCCTCCAGACTTCCTCCCCCATTTCCACGCTTTTGCTCAAGAAGTCTCATGATCTCGTTCAA
GGAAGCTCTCCCAGGTTGGCTGACCTCATAGCTGGCAACAAAGGCAACTACTGCTAGGGGTGAACACAAGGCTACAGTGCACTCATCCTGCACCCAA
ACTCAGAATTGCACCAAAGTGTGTGTGTGTGTGTGTGTGTGTGTGTGTGTGTGTGTGTGTGTGTGTGTGTGTGTGTCTGTGTCTGTGTCTGTGTCTG
TGTCTGTGTGTCTGTGTGTCTCTGTGTGTGTCTGTGTCTGTGTTTGCTTTCACTGTGTATGCATATGTGGAGACCAGAGACGAATGAGGAGATCATA
GACATACACTGTCACACCCAGCCTTTCTGTGGATGCTGGGGATCCAAACTCAGGTCCCCAGATCCATGCAGCAAGTCCTTTGCCCACTAGGCTGTCT
CCCGAGCTCTGCACCTAGGCTCTTTATAGGACCAGCAGTGTGGCCTCACTGTCCTCTATTTCCAATCTGTGTTTATTACAACTCCGCTGACATATTG
GGGTTGATTTCTTGGAGGGATGCTTTTATTCTCTTGGTGAAATATTTTTCTGTGCACTGATGGCTTGTGAAATTTTCTTCTCTGTTGCCTCAGTTCA
AGCCAGACGAACAAGGAGCTGAGATTAAGCTTAGTAAGTAAAGCCCAGGACCTGGAGGATCTGGAAACTGGGTGAAAGAGTTGTCCTCTGTTGGCTA
GGTTAGGTTCAGGGCAGCCAGGATGGAGTCAGAGGGGTGGCTGACAACACCCAGGGGCCACTGTCAGCTCTGTGACTTTCCCTCCAGAAAAAGGGGC
CAGTTCTGTGCAAACATGTTCTTGTCCAGGAGTTTGGTTTCTTCTCTCTGAGCACCTGGCACAGTGGCACCAATGTGAGCAGTCACTTGGCAGGGCA
GAGAAAAGCAAGCTAGCAGTCCCCAGGCTCAGGTGACAGAGCCAGGCCCAGGAGACAGGGATATTGACTGGGGCTTTAACAGCACTATTGATGCCAA
TCTCGGGCAAAAACCTGATATTTCCACTTGGAATAACAAGAAACAGCCAAGAGGATTGGAGAGAGGTCAGTGGACAAGGAGAGCCCTCTGCAGGTCG
TGCTGGGTGATTCCAGAACAGAAGAGGGCAGCCCCTGCTGGACAGGGTCTCCTGAGATGATGGTGATGGTGACGGTGATGGTAATAGTGATGGTGAC
AGGGACAATGACAGTAGTAGTGGCTAGGAGAAGGAAAAAGAAGAAAGAGAAAAACACAATGTCAGGCTTTAAATAAATAATCCTCATGAAGTAGATA
CTATTTATTGTGGTTTTGATATGAAACACCCCTCCCCCAAGGGCTCGGGTATTGGAGATTTGAGCCCCAGCGTGTGGTGCTATTGAGAGGTGACTTT
GTTGATGGCGACTTTGTTTGATGAGGAGATAAGAGGTGGACTGTAAGGAGGTGAAAGCTGTCTGAGGAAGTAGGTCACCAGTGGTGTGCTCTCAAAG
GTGGGTCTCAACCTTCCCAATGCTGTGACGCTTCATTTAACACAGTTCCTTATGTTGTGGTGGCCCCCCCAATCATAAAATTAGTTTTGTTGCTGCT
TCATAACTGTAATTTTACTACTGTTATAAATCATAATGTAAATATTTTTGGAGCTTAGAGGCTTGCCAAAGGGGTCACGACCCACAGGTTGAGAACC
ACTGCTCTAGAAGGAAGTCACCTCCTCTTCTCTCCTTGTCATTCTCTTTTCTTCCTCTCCCTTACACTCCCCTTCTTCTCTTCTCTCTCCCTACTCC
TCACCTCTCCACTCTCCATGAAATCTGATTTCCCCTGCTATCTACCACAATGCCGGATCTCATATTCCCAAGAAGAATGGAGACAAACAACCCTGGA
CTGGATTCCTCCTCTTTTAAGTGTGACTTGGGTGTTCTGTTACAGCAATGAAAAGCTAGCAATATAAGATGGCTAGTCTCATCTCTTAGATTTAAAA
AACTAACATTTTCCAAACATAGTGGCTCATGTCTGTAGACACAGAGCCAGGGAAGCAGAGGCAGAAGGATCCACTGCAGGTCCAAGGCTGGCCTGGA
CTATGTAACAAGAGAGAGAGAGAGAGAGAGAGAGAGAGAGTAGAGAGAGAGAGAGGAGAGATTGAAGGAAAGAAAGATTGAAGAAAAGAAAGATGAAAG
AAAGAAAGAAAGAAAGAAAGATTGAAGGAAAGAAAGAGAGATTTAAAGAAAGAAAAAAGAAAGATGAAAGAAAGAAAAGGGAAGAAAGATTGAAGGA
AAGAAAAGAACGGAAGGAAGGAAAGAAGGAAGGAAGGAAGGAGTGCAGGGGGAGGAGGGAAGAAAAGAGTGGAGGGGGAGGAGGGAGAAAAGAAAGA
AAAGGAGACTATATGAAGCTATTTGCTCAAAGCCATGCATCTTCTATCAGAGAGTAGAATTTGAACTCAAGTCATTGCCTCTGAAGCTTGTATTACC
CCACACACCTGTCATAGCTCGTGAGCACATTTCAGAAACTTCTAGTCTTCTATTGTGCTGTTTCTTCCTGTTCTTTCTAGTTATGTATTCTTGCAGT

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

GTTAAGGCTTAGGGGATTGGATATAAAATATCTTGTGCATAACAATATTGGCAATAGTAATAACACCAGCTTAAATTTATTTTTTATAGCTTTAGTA
ATTTAATTTATGTATATGAGTTCATGGTAGCTGTCTTCAGACACACCAGAAGAGGGCATCAGATCCTATTACAGATGGTTGTGAGCCACCATGTGGT
TGCTGGGAATTGAACTCAGGACTACTGGAAGAACAGCCAGTGCTCTTAACTGCTGCAAAATGGTACAGTTACTCTGGAAGACAGTTTGGCAGTCACC
TGAAAAACTAAACATACTCTTTCCATATGATATTGCAACCATACTCCTTGGTATTTACCGCACCCCCAAAAGCTGAAAACTTGTCTAAATAAAAACC
CTGCACACAGATGTTTGTAGCAACTTTATTTGGAATCGGCAAAAACTGGAAATGAAATGACTTTCAGTGGCTCAATGGACAAATGAATTGTGGTACT
TTCCTGGCCGTGGACCATCATTCAGTACCAAAATGAGATGAGCTGTGGAGCTAAAAAAGACATGAAGCAACCTTAAATGCACAAGTGGAAGAAGCCA
ATCCAAGGAGCTGCATACTGTATAATTCCAACCCCATGGCATCCTGGAAAAGGCAGAACCATGGAAACAGGTTTTTAAAAAATCAGAGATTGCCAAA
GGCTAAGGGGAGAGTGGATGGCTGGGGGCAGCAGAGAGGAAAGCACCCCACAACCATCATGGCGGATACACATCCTCGTGGCCGTTCTGGGTTTACA
GCAAGAGAAACCACACCAAGAGAAAGTCCTAATGTGAACTAGAAACCAGTGATCATGCTGTGCCAAGTTAGATTTGTAAGTCGTAAACAAGCTACTA
TTCTCACTGGAGATGTCTAGAGTAGAGGAGACTGTGTATGCCAGGCAGAAGGCATGTGGAAACTCTTAGTGCCTTCTCTCAGTTTATATGTGTTTGT
GTGTATGTATACATCTTTGTGTGTATGTGTGTGCATGTACACGTGCGTACACACAGAAGTCTGAAGTCGATGTTTTCCTATATCACTCTCCACCTTA
GTTTTTCAGACAGGGTCCCTCATGAAACCTGGAATTCACCAGTTTGTTGGGGCTAACTGGCCAGTGAGCTCTGGGCATCCTCATGTCTCTGCCTTCT
CAGCTGGGATTCCACGTGTTTGCCACCACATCCTGCATTTACACGGGTGCTGAGAACCCAAGCTCAGGTCCTCATCAGTAGGGCAAGCACTTAACTG
ACTGGGCCATCTTCCCAGGCTCTTCTCTTGCTGTACAATTAAAAGTATTCTTTGAAAAAGTCTAATATGCATGCCTATATTTCCAGCACCGAGTAAG
TGGAGCTAACCTGGGCTAGACACTAAGACCCGGTCTTGGGGGTGGGGAACACCTAACAAAAAAATAAAAACAAAACAAAACAAAACAAAAACCAAAA
ACATTAAATGAAGAGCCAGGGCAGTGACAAGACACGTGACTCCTCAATCTCTGTCCAACTCTGGAATTCAATAGGCTACTTTTTCTGTTTTCCTCAT
CCATAAATAGAAAAAGGGATAACTGTCTCACAGGATTGTCACAGAAATTAAATGAGATGCTGCTGGATGGATTAGCAGTAGGAGCATGTAGCAGCAG
ACCTGTGCAACTCTGTGTCTTTCCACTGATGGCATCATAGGCTACTGCTGGGCAAGGACCTATTCATTTCATAATCGCCTCTACCTAGCCCAGTATG
TGGTGTTTGAGCCCCCTGAGTCTGCTGGGTTGATGGTAAGAACTAGCCTAGACTTCTCTCTCTCTCTGTTGGACATTTGAGGGTTTTCTCAACTTTT
TGCTATGAGCAAAGTACATCTCAAAACCCTTTTATTTACATCACCTAATTTGATCTGCATCCCAGGTGAAGCCAGCAGAAGAGGGCTGTTTGCCCAC
GCCCACACTCTGAGACAGACAGAATCACTATGGCTCAGAGAAGTGAAGGGACCTCTTCGGGTCACAGGTATATCAGTGATGGTGATGACGATGGCGG
AGCCTCTGGCCCTGCTTCTCTAGCCCCTACCTCTGCAGACCTTTTTCTCTCTGCCTGCTGCCTTCTGCATCAGAGGTCTCTTAAAAAATTGCAGCCT
TGTCACGCTGGGCCTGGTCCTTCTGTCCGCTGTCTGGAGGGCAGCACCTTTGCCCAGTGGTCCCTGCTGGGGATTGTGAACTGCAAACTCCCAGATG
GCCTCTGAAATCAAATATTTTATTTCCAATGCCTCTATTTTCCCAGAATGAGGAGCACACCAGTTCCCCCACACACACACTTGCTTTCGTCCCTATA
AAGAGGTGAGGAGATGACTCTCCGTGTCCAGGAGGAAGGACTTTGGCTAAAAATAGCTGTGGCGTGTGGATTAGCCAGAGTGGTACCCAGGACTGGG
AAAGGGAGGGGGACGCTGTGGAGCTGTAGCCAGACTGGTTGCCATAGAAACGAGAGAGGAGCAGGGGAACCTGGGAAGTGGGGATGACACAGATACC
AAGTCCTAGTCTGAGCTGCCGTTACATTCAGGAGAAACAGCAGTGTCGGCGGCTCCCAATCTCAGAGGGAACCTAGGGTACTGGGGGAGATGGTGTC
AGGGACATGGACGCCAACCCCCAAGGGTCTCTGCTGCTGGCTACTCTTCTCTCCAGGCTCTGTGAGTTGAGTTGTGGGACTTGGGGTTTGGGCCCCT
ATTTCTGAGCCAAGAGGGGTTTGGGTGGAGCTGCTCCCAGAGGGACTTCTCCCCGACAGACCCCTTTCCAAAAGATAAGCCCCCTGTACTGGCCAGC
GCTCTCTAGAGGGAGGTGGAGTACTCCAAGATAATGTGGTGCTCGGATCTTACTGAAAGGGGTCACAGCATGCCCAAGAACTGTGGTCGGAAGAACT
GGAGTTATTTGGAGGGAAGAGGAAGAAATGAAGACGTTGCTCTTCAGGTGGTGGACACTGCACACCTTTCCTGTCCCATGAAGAAGAGAGCTTTTCT
CGAGATGGCAATGGCTAGGATGTCATCAGTAGGCTCCCTGGGCAGTCGTGTTCTGGGAATGATCAGACACTGGGAATCCTTCCCCATTCCTGGCCGT
AGATGGAGGTCAGATCACCTTAGACCCTACGAAGACTGTCTAGAAGCCCACCTGAAGTTAATACTAGGATGAAAGAGACCTGGGGTCTCGAGGCACT
GAAAACTTACAGATGAGGTGCAGAGGACATCCTGGGCTGCAGAGAGGGAAAAAACAAGCCTGCTTGCTGTTGGGGGAGGGGAAGATCTTAATCTGCC
ATTGCCGAAGTGTTCCCAGGTCATGTCTCCTGACTTCCATGGAAAATAAGTGTGTGGGGTTACAAACCATCTTTTTGGGGTTTTTTCCTTGTGCCTT
TCTTTAACATACACACACCCTCCAAAGGTCTGCTGGCTACAGAACACTTGGCTCCAAAGTTTAAAAATGGAATGTCGGGTTTGTGGGTATATATTCA
TGCAGTTTCTCCCTAGGATCTGGTCAAACATCCAAACCATCTGAGATCCTTATGTCACATTTCTGCCCCCACAGGGCCACCTGCTCTCCCCACTTCC
CCAGCCTTCCTGCCCCACCCCTCACCCTGAATGGGAGGAGATGGCAAATCCCAGGAAAGAGAAAGGAAGGTTGATGAGTCTTAATCCTTATTCTACA
GACTTCTGTTCATACGGTCCATATCTCCTAGGGGACCCTGAAAGCCTAGGAACCGACTCTGGCCATCCATCTCTCCGGGAAGATTATAACCCAGAGT
GCTTCTCAGGGGGGAAGAATTTGAAGCAAAACCAGGTGGGTTTTGCTTGGAATCTGGGCTTTGTGTGGAATGTGGGCTTTGGGACATATGGCAGGAG
TGGGTGGGGTTGCTGGTAGGGTAGTAAATGCAAATCAGGAAATTGGTAGGGGGGGTCGATGTGGGTGTTTGGTGTTTCGATTGGTCTGATTTCTTAT

TABLE 1-continued

```
(mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

CTCTTAGAAGAATACGAATCTGAGAGATACTAGACTAGCGTAACTCTGGATGGCCTGGCGCCTCCTTCATCCTTGCCGTGGGCAGTTGAGCTCACGC
GTGGCCCCCAATCTCCTATTGCCCACCCTTTTCAGCGTGTCTCCTGTGGGAAAGAGCCCTGGCGGGAAATGGGCTGGTATCAGAGCATCAGTGACCA
CGGTGAAGCAGTTAGAATTGCCAGTGGGAAGTTCCCAATGCTGAGGACATCCAACCTTTGCACACTGGAGGTTTTTGTGCACAGTCTGCATTGCTTT
CTCCTTGGGAAGTCTGGGGTGGAGGGGAAATGTAGCAGGAGAAAGAGTGAGGCCAGGGAGAACACCGAGGGAACAGTCTTCAGGTGGGGCTTCTGGC
AGGATGCTGAAGAGTGCTGGGGGAAGGGATAATTGCCAGGGAAAGGGCTGTGGAAGTCCTCATCGCAGGGAGGGCTTTGCATGGAGAAGGAACTGCC
AAGAAGTCTACCTCTTCAGTACCCTAAATGTCTGATCCGGGGTGCCTGTGAGTTGCTACATACACCAGCTTGAGGTAGTGACGCTGAGATCTGTGAC
ATCGAGATGGCTAATGCCTCTTTTCTTACTGAACTTCGACACCCAGTCTGTGCTCTTTATCCTGTGTAATCTGTACAACTCTCTCTCTCTCTCTCTC
TCTCTCTCTCTCTCTCATAATTCTTTATTCTTTTTTAAAAAGATTTATTTACTTAATGTATATGATTACACTGCCGCTGCCTTCAGACACATCAG
AAGAGGGCATAAGATCCCATTACAGATTGTTGTAAGCCACCATGTGGTTCCTGGGAATTGAACTCAGAACCTCTCTGGAAGTGCAGGCAGCGCTCTT
AACCCCGCTGAGTCACCTCTCCAGCCATACAACTTTTTCTTAACCATTGTTTTATTTTATGTAATAGTTTGCCCTCATGTACGTCTGTGCATTACCC
TCGGAGGCCAGCAGAGTGCGAGTTACAGCCGGTTGTGAGCCGACTTGTGGGTGCTGGGAATCGAAATCAGATCCGCTGGAAGAGCAACCAGTGAATC
ATTTGAGCCATCTCCCCAGCACTTGTGCCCCAACTTTCTGAGATTTATGGGATGTTAGGGATTATCGTTCCCAATCCACCAGTGGGGAAAAACTAAG
GCTAAAGAGACAGGAAGGGAGATTGTCTCACAGCATTGGCCCTGAGTTCGGGGCAGATCCATCAACTCGGCACACCTTTATTAAGACCCCGCAGGAT
CCCCGCTGCGGCCGCCATGGCGCAGGAGAACGCCGCTTTCTCTCCCGGGTCGGAGGAGCCGCCACGCCGCCGCGGTCGCCAGCGCTACGTGGAGAAG
GACGGTCGCTGTAACGTGCAGCAGGGCAACGTCCGCGAGACCTACCGCTACCTGACCGACCTGTTCACCACGCTGGTCGACCTGCAGTGGCGCCTCA
GCCTGCTCTTCTTCGTGCTCGCCTACGCGCTCACTTGGCTCTTCTTCGGCGCCATCTGGTGGCTCATCGCCTACGGCCGCGGCGACCTGGAGCACCT
GGAGGACACCGCGTGGACCCCGTGCGTCAACAACCTCAACGGCTTCGTGGCCGCCTTCCTCTTCTCCATCGAGACGGAGACCACCATCGGCTATGGG
CACCGCGTCATCACCGACCAGTGTCCCGAGGGCATCGTGCTGCTGCTGCTGCAGGCTATCCTGGGCTCCATGGTGAACGCTTTCATGGTGGGCTGCA
TGTTCGTCAAGATCTCGCAGCCCAACAAGCGCGCCGCCACTCTCGTCTTCTCCTCGCACGCCGTGGTGTCTCTGCGCGACGGGCGCCTCTGTCTCAT
GTTTCGCGTGGGCGACCTGCGATCCTCACACATCGTCGAGGCCTCCATCCGAGCCAAGCTCATCCGCTCCCGTCAGACGCTCGAGGGCGAGTTCATC
CCTTTGCACCAGACCGACCTCAGCGTGGGCTTTGACACGGGGGACGACCGCCTCTTTCTCGTCTCACCTCTCGTCATCAGCCACGAAATCGATGCCG
CCAGCCCCTTCTGGGAGGCATCGCGCCGCGCCCTCGAGAGGGACGACTTCGAGATCGTAGTCATTCTCGAGGGCATGGTGGAGGCCACGGGTGCGGG
CAGGCTGGAGGATGGGAGCAGGGATGCAGGACAAGGGCAAGAAAAGCAGCCAGGGGAGGCGCAGAAAGATGGACAGAGAATGGAGTGTAGGGTGACA
GGCCTGAGGGGTAGCGGGGGCCGGGGAGAGGACGGGAGATGACAGGGATGGACAGGGTGACTTTGCAGAGTCAAGAAAAGCTTGGAAGAGGTCTATG
AAATGGCACTAGCTTGAGGCCCTCACCTGACAGCTATGTCACTTTGAACTACATTTTACATCTCTGAATTCATTTAAGCCCAGCAAAGCTCCCCTGG
AGGTTACTTTTGACTGTGCTCGGTTTTCAGAGAATGAGTAGCCCCAAAGAAAGGTCCCATAAATAGCCCGCTGTCACAAGCCAATAAATAGCACAGC
CTGGGTTGAACATAGGACATCTATCTTCAGTGTTTCCTGGTACAGTGTTGGGATGAAGGTTAAGTGCAGGGTTCTTGAAGCCCAGAGGTCCATAGCT
CTGGAATTTAACTGACCTAAGTAAAAGGGAGGTAGGTAGGAAAAAGACTAGTACTGGAGCAAAAACAGGTCCTTGAAGAGGTCCTAGCCGTCAGGGA
GCATAAGGAAGACGCAGGTGAACCAAGAGGCCACTAGGAGGAGCTGCGGAGCTGCTACGGACAGGCTAGCTCCCTGCTGCTAGCCTTGAAACCTGGC
TCCTGGGCCTAGACAAAAACATCATCTTCTCCATGGCCACCTCAGGTCTTCCCACTCCCCTCTCCTCCTTCACTCCAACTAGGCTGGTTCTAGCCCA
TGCCCATTCCACACTGCTCCCTCTGTCTCTGCGCTGTCCCTCTCTCTGACACAATCTCGGACAGGTTTCTATCAGGGACTTTTTCATCTGCCTTCTC
TTCCCCCTCTGCCACTGCCTCCACTTTGCACCTAACCCTACTCCCCCAAGCCCTACCTCTGCTTCTCAGGCCTTCTCCCTGCAGAGGCCCCGGTGGC
CTCTCTTTCCCTACGATCCCTGATACATCTTATTCCAGCTTTGCCAAACAATACCAATGACCCCAAGATGTCTCAGGGCCAGACTTCCGATGTCAGA
GCCGGTCTCTGATTAGTGAATGCTTACTCCTCTGTTTTTGAGATGGATTCCGGTTTGGGAAGATTCTGAGGTAGGAACAAAATGATCTGCCCCGAGG
GGAGGGTGCACAAACCCAACAGAGAAGACAGGACACAGGCTCAGGGCAAGAACTGGGAAGGGGCAGTGTAAAGGACATGGGGATGGGAGCTTGCTTG
ACTTTTCTAGAGATAAGGCTGGGAAGGATGGTAGTATTTTGGGATTCAAACTGCTTTTGAAAAGCAAGAATAATGAGCCAAAACCCAACATGATGAC
ATTTAAGGGGAATAAATATAAAATTCTACATTTAGGCTTTAAAAAAATCACTTATGTAAGCACAGCATGGAAAGGCTCCGGTGGAGAAAGAACTGGG
GGTTTTAGTTGGCCACTGGCTTTGCTGCAGCAACGTGATGCAGCTTCCAAAGGCGTTTATGTAATGTAATCATGGGCCCGCTTCACCAAAGCATCTG
GGCGAGAAGCAAGAGATAGTAAGCCTTCTTTTATGCACAGATAAGGCCACAGTTGAAAAAGCACTTCAGATGAGCCCTTACCTGGGCCTGGTGGCCA
TTCTGATTTGCAATGAAGATTGTAAGCTTTGGGGGAGTCAGATGAAGTAAGAAATGGCCATGAGTGTTCAATCTGAGGAAGAGAAGATGTAAGGGAA
CCCCATATTTACACTCAAGGGGGTGTCAGGTGGTAAGGGAATGGAACCAGGGGCCACGGGTCCTAGGAGACAGATTTTAGTTTATGTAAGAGAAAAC
```

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

CCAGAGCCAAAGAGATGTCTCAGCTTGCAACCACGCCTGACTACTGACCTGAGTTGAATTACCAGGTCTCACATTGGGGAGTCAACTGTCTCCCCAA
GTTGTCCTCTGACCTCCACATACATACATATGCACGCATATAGACACATAAATGTAAAACACATTTGTAAAGACGATTGGCACGTTGCACAAAGGAC
TGGACTTTTAATGAGATGGTGAGCTTTCAATCCTGGGGTGTAATCAGTTCAGCCCATTGTCTGGGAATGCTTGGGGGTGGGTGGAGGCGGCTCTGTG
GGAAACAGGAAGGTTAGGCTTAAGGTTAAGCTTCTCAATGGAGAGTAGGGGAAAACATAGGCTGGCAGATAGAGAAGAGGGCTAACTAAAAAGAGAG
GTGGGACTCTCAGAGAGAGAAGAGGGTTGTGGGATGACAGACAGGAGAAGGAATCCTCTGTCAGGGGCCCCTTTGACTGATGCCGCTTCTCCTCCCC
CCACCCCCCAGGAATGACGTGCCAAGCTCGAAGCTCGTACCTGGTGGATGAAGTGTTGTGGGGCCACCGGTTCACATCCGTGCTCACCCTGGAGGAT
GGTTTCTATGAGGTGGACTACGCCAGCTTCCACGAAACCTTTGAGGTGCCCACACCCTCGTGCAGTGCTCGGGAACTGGCAGAAGCCGCGGCCCGCC
TTGATGCCCATCTCTACTCGTCCATCCCCAGCAGGCTGGATGAGAAGGTGGAGGAAGAAGGGGCTGGGGAGGGGGCAGGTGCGGGAGATGGAGCTGA
CAAGGAGCACAATGGCTGCCTGCCACCCCCAGAGAGTGAGTCCAAGGTGTGACTGGTTTCCTCCCACCCCCTGTGGCAGACCAGGGGGCCGGACTCA
GGTACACAGAAGCTGCGAGTGGAGGTGGAAGAAGAGGAGGCAGGCAGTGTCCCGAGGAACAGCTAAAGTTGGGAGAGGCCCGCTGAGTCCAGGATCG
AGTAGGGAAGGCTGAGGTCCTGGTTTGAAGAGAGAGGGTTGCAGGGCGGGGTGAGAGAACATGTCAGTCTGTCTGTGTTTGACCTTCACATCGGTTC
ATGGGTGGATGGATGGACAGAAGGATGGGCTCATGGGGGTTGATCGGGAAGGTGGAGCAGATAGAGACAGCCAATGGATAATCGCTCAGGTGGTAAG
TGGCTTGGCAGTCGATGATCGTCACCTGCAGCACACCTTTGTGAGAAATCCATGGGCATCCTTTTCTTCCAGATATAGGTAGCCTCAAACCAGGGAG
CGTGGCTTAGGGAGCAGGCTGTCAGGTGGACTACCACCCCCACTCACCTCCCCTCAACTGGCCTCCCTATGTGTGACACGCCTGCCTAACTAGAGAA
GAGAGCACTGGGTAGAGGTGGGCACAGGTGTGGGTGCCCTCCCCAGCATCACTGTCCCATGGCGAGAGGTCAGAAAGGCAAACAAGCAATGGGGGTA
GATGCTGAGCAGGGAGGGGCCCTGAAGCAGGACCTGGGGACAGCCAAGGACAACTATTTTGTGAGAGAGGAATGAAACCTTGCAGGTCCTGCCACAG
AAGCAAGAAGCAGAGGAAAGGCCATGGAGAGACTTAATAAAGGGTTTTACAAGGGTACCTGGATCCCAGGGGGAAGTAGTTTATCCTTGGGGCACAG
TGGCAGGGCTCATTCAGAACGGTGAGTAAGTGTCAGGTGTGATATTCAAAGACCTGGTTCTTAACACGAGAGCACAGCGAAGGTGGACGTCAGAAAT
AACTCCCAGCCACTGAAGGAAGTATGGCTTCAGTCTGGAGAGCTCAGAAAAGACTCGACCCTAGGAGCCCACACAAGCGGTTATAGCCACAAGTGAG
AGGGCATTAGGGACAGGAAGCTAAGGATTGAGTAAGGCAGTGGGGAATGGTGGGAGCCAGCAGTTACAAAGCTTTACTCACCTGGATGGGCTTGTTA
AAACACAGATTACCAGCCCCACTCCCTGCATTCTGACTCAGTAGGTCCGGGACGGAAACCAAAAAAAAAAAAAAAAAAATCTGCACGTCTAACTAGTT
CCCAGACCTAACAGGTTCCCAGATCGCGGTGACACTGTCTGTCTGGGGACTGCACTTGGGTGAAGCATCTAAGCGGAAGAGAAGCTGGAGGAACTGA
AAAGCACCCCAGGTTCCTCAAGGAACAGAGAAACAAGAAGGGAAATGTTGGGGAGAGGGGACCCAGGTCCAGACTCGAAGGGCTTAACTCTGGGTCC
AAGAAACGTCATTGGTAACTGGCCAGTGGCACCCGAGAGGGCAACAGAGATAGGAGAAGGCCATTTAGGGACCCCCAAGGAGGCAGTGGGGGGTCTG
TAGCTGAATTGGCCTTACCACAAAAGACCAACTCTCTTAAGAGACTCACAAGGCAAGACTGACTAGGGGAGAAAATGGAGCCTGTACCTACAGGTGT
CTGCTGTCTGCCACCTGTCCTCCCAGGACAGGGCACCCTGGAGACACATTCCACCTCCACTGCATCCTTGTCTTGCCCCAGTCATCTTGGGATGGTT
GAGGGGACAGCAACAGCATGGCAATGGACCTGAGGCTGGCCCCCCTGGAGCTAAGTGTAGCCCAAGTGAGCACGTAACCTGATAGGACTGGCTCAGA
CTCTGGCCCTGGCTATACCCATCCCTGCCCTCGAATAAAAGTCTGCTGCTCTGTCCCAGGCTAAGAAGCCAGCATCCAATGGGGCATCGAGGCCTCC
CTCCCAGTGCCCAGCTCAGAGTGGGTCCACGCAGAGAGGACTCAAGCTGCCTGTTGCCTCTCCCCTTCCATCTAGCAATGGCCACAGGTTTCGGGAC
CAGCTGGGTCACTCTCAAAGATGAGGTCCACGCACATGAACCTGCTGGGATCCCACGAACACATATTGGACCTGAGCACAGGGACTGAGCAGGGTTT
GAATTCAGAGAAAATCGAGGAGTCTAGACAAGAGGGGTGGGGTGCTTGGTATCCGCACACGAAGCAATGGAATGGAGACATTGAAGCTGTTCCTGGA
GGTCACTCAGGGCACCGCTGTCCACGGCACAGCCAGGAGACCTGTGTTCTAGCACCAATGCTGATTGTCACTAATTACCTCTATGACTCTCAGCAAG
ACCTATTACTTCTCTGGGCCTCAGCTTCCTTATCTGTTAAAAAAAAATGATATGTTCGCAAACTCAATAATGCTCAATAAACTTTCAACTACTGAAT
GAAAAAAGGTAGACTGGATGCCGCTCAAAGTATTAGGACAGCTGAGGCTCTTAGGACCGGAGAACCCTTTAGGCGGGGAGTTGCGGCTAGCCAGCAG
GCAAGTCCTGGCATCAGATGTAAGCAGATGAGGCGGCTCTTGTGTACACAGAGGACACAGGCTCTCCCAACTGCTGCTGTCCTTAAGTAGGCAGCCG
TGTTCTGAAGCTCCTATTCGGCTGCTGTCAGAGAATAATTAAGGGCAGGAGGAAAAAGACTGAGGCCCCAGGGCCTGTGGGAGGAGTCTGGTCCAAG
ACTAGTTCAACCAGGAGAAATGGACCAGAGGAGGGTGTGCCCCAGTCTGGAGAGCTCAGAAAAGACTCGTCCCTTGGAGCTCTGTGAAAGGGGCAAA
GCTCAGCTGGAACTCACCCCTCCTCTTCCTAGGTCCCCCTTCCCAAATAGAAGCCCCATTAGGACTTGGCTCAGCACAGACATTTTGGACAACAGAT
GGGACCCCGGCATCCCCTCATGCAGTTGGTGGGTAACAAGGCCCACGAAGGGACAGATGGTGTTTATGGTGGGAAGAGAGGCCCGGGTTGTCCAGCA
ACCACCCTACTACCACCCCACCCCCACCCCCGATGCTGCCTTTTATAGCTTCACCGCAAGAGAAGACACAACAGGCCTCGATTTTACAAAACCAGTT
TATTCACATTTTAGAAAAACTAGTTTGAGGACAGGAACTGGCCTTCCTACAACATGAGTGTGGGACTAAGAACGGCAGCCAGGAAACTTCAGGGAAG

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

GTGGGGACAGGGGAGCCATGTCTCCCACTCTAGGTGATGGCTGGTCAAATAAATTAAAGGTGGGCTGGACAGAGGGAGAGGGTATCCAGGCAACCAG
AGGAGGGGTGGCACTGGCTGGAAGACAGTCAACACCTGCAAGAACTGGAAAGAGCATGTGGAGTCGGCTGAGGAAGAGGCTCCCTTTGACCCTTACC
CTGCTATACGATCCTGCAGGACTGTGAAGCTGGCTGCTTCTCCCCCTGATGGTGCCCAGGTACAGCTCAGCACAGGAAGCCTGAGGAAAGGCAGTTC
CTTTCCCTCACCTTGGGGTGCTACAGATCACCGCTTCCGCATCCTCTTCATAAAGCAGCAGGTGATGGTAGCCAGGACGCTGGCGCCGGTAACTAGG
GCGACTCCTGTACCCACCAACAGGGGCACAAATAGGGTATCCACAGCTGGCAGAAAAGAAGACAGGCTCTGCTCAGAGAGTACCACGGTATCTGACA
CTCTCCCCTGCAGATTTTCTAGACTCAGCCCTCCCCAAGGGAGAGCTGAGCGCCAGTCCTGCCTACCTACACTTCACACACAAACACAACCATCCCC
CATCCCCCATCCCCACCCCCTCCCCTCGGTCTCAGCACTCACGCCGGCTTGGGGCCCTTCATGCAAAGGGATGTGGAAAAAGGATTGCAAGGGAAGA
CAGGAAGATGGAAAGGGGCAAACAGAGCAGGAACAGGTGGGTAGATGGTGGCTGTCACTCACCATGCGTGTAGGGGTAGACTGTAACAGGCCCGGAG
CGCGCACTGCCTGCCTGGTACCAGCTGTAGTCCGCATGCTGCACCCAGGCACTTGGGGCACAGTGGTATATGCCTTCATCCTCAGGCCCCAAGCCAT
GCAGTCTTAGCCGATGACTTCTGGGTCCCACCAGCTCCACACTGACAGGACCCCCTCCAGGCCGGACTCCCAGCTCTGCCACACCGTCCTGACCCAC
TCCACCCACAAGCTGAGCAGGGCCAGAGCTCAGCTCGCCCTCCTCTGGCCTCTCCACCCACCAGCTGGCTGCTAGTCGCAGCCCTGGGGGGCCGCCC
CGCACAGAGATGTTGCATAGCACGGAGGCCGTCTCTCCCCGGTACACAGTGCCCCCTGCTAGCCACGCCACGGCCTCTAGCACCACGCCTGCAGAGC
AAAGAACACGGGGGTTACCAGGTGAAGGCCCAGGGGCTAAGAGGTTAGGAAATAAATTCTATAAGTTCTGAACCCCGTCAAGGGCTCAACATCCTCT
TACCTTCTTCTCTCACATGCACAGGGAGAGGCCGGGAACGAGCACTGGCCGCTTCACGAAGTCGGGTCCCAGACCCTCGAACATAGGCTTTGGCGAG
GCAGCGGTAGGTACCTGCATCAGCGGGCCTGGCAGCCTCCAGCCGCAGTCGGTAGGTTCTGGATGCTACTTTCTCCATGGCAATGTGCCGGTCCTCA
TAGCCAGGGCCCAGGCTGCCTATACCTTCCGTGTCTAGCTGGGCCACCAGGCGGCCGGGTCCAGGAGCCCCTGCAGGGGCCATCTCCCAGCCCACAG
AGTACGCAGCATGACGGCCTGGTGGGGGCAGTGCACCGGACACATTGCACAGCAGTTCTAAGGGTTCGCCTGGGCCAATCCGACGTTCACCAGGTCC
CACGGTCACCGCCAGCTGGCTGGCTGAAACACACCAGGAGATGGGAGGAGTCACTGAGATGCCTGGGCCCCCCACCTGTAATTCTTCTTTGCAGAAA
TTTAGAGGCCTCTTATATCTCCCTCACCCCAGGACCCGAATTTCACCCTTCCCCCCATAGCCTTTGTATCTCCATGCTTGTGCGGCACTCCCGATGC
CCAACTGAGAGACACCCCCCCCCCCCAGTGGGCTATGCTGCACTCACATAGAGTCTGCACATCAACATGAGCCAGGACTGCCCTCTTCTCTGCGAC
CTGGACCCAGGAGCCGTCAGGATCCTGAATCCACTCAGCGGCCGTACAGTGGTAGGTGCCCGAGTCTCCAGCCTGGGCACCCCCAACCACCATTCGG
TACCGATCAGTCCCTTCCTTGCTCAGCCGAAGCTCCCCAGAAGCTAGCCTCTCAGCGTAGGGCGCTCCAGCCTCCACCGCCATGTCGGAGCGCAGTC
CCACTACTTCCTGTAGAGTGGCTCGCCCCACTGGCGCCTCCGGAATGGCTCTCCCAAAGGACACCGACAGGTGTGTGTGTTTCTTTGTTTTGGTCTG
AGCCAGGCAGCCCAGCGCAAGCTCCTGCCCCTCGTGCACTGTGAGGCGTGAGGGGGAGGTGGCAGCCTGGCGCCCTCGGGGCCCTGGAGGGGCAGCA
GATACCTGCAGCTCATCTGGAAGAACTGGAGAGAAAGGCTTTAGTGAGAGAGGGCTTGGAGCAGCATCCCTCCTGTTTCCTGTGCGTATCCTGTTTC
ACTACACACTCTCTAGGCTTCTAGAATGTAAGAACTGTGCTCTGTAGCTTTTCTTCTATACCGCAGAGATGCCAAGCTTGGTCTGGGCACATCAAGA
TATTCAATAACTACTTGCTGAACGTCACAGAGCAAGCCTACTGACCCCTACTCTGATGTCTAAGACTGATCCATTTTAAATACTCAAAAAAAGTAAT
CCTGTCTTCCTTCTCTAAAGATAAAGAGGCTGGACCTGATGGTGCCGGCCTATAATCGCAACTACCCAGGAAGCTAAGGCAGAAGAGTCAAGTTCAA
GGGCCGTCTGGGCTACAGAACAAGTTCAGTGCTGGTCTGGTCAACTTGGAAAGTTTCTGATTCAGCCCATCCCCCCCCCAAAAAAAAAAAAAAAAA
ACTGCTGGAAAGACTGGCTTGATGGCACTGGAGCTGACACAATACTGCCTGAGCTACACAGTGAATTGTGGGAGTTTTGTCACCAGTTTCAGGCCAA
CCTAGGCTAGTTGTAAGCTAGCCTGGGCTACAAGAGTGAGCCCTCAAAAAACAACACAGGGAATATAGCTTAGTAGAGTGCTCCCTTGGTATGTTCC
ATGCTGTAGGTTCAATTTCCAGTACTGAGAAGATGGGGGTGGGGGGAGAAGAGGAGAAGGAAGAAGATGACAGAGAAGGAGGAAGACGAAGCAAAAA
TAGATCTGAGCGTGCTGGCTTATACCTATAACCCCAGTGCTTGTGAGGCTCTCTCACCACCTAGCTCAGAGCCCAGTACCTCTCAGCTCCACCTTGG
CACTGTAGTTGCCCAGGTACTGCGTATCCGTGGAGGGGGTGTAGCACTCATAAAAGCCAGAGTCCTGGGCCTGCAGGCGAGCAATCTTGAGCACCAC
CGAATCTCCCTTCAGGCGCTGCACCTGCAGGTCACCAGATGCCACACGAGGCCCAAAGACAGCATAGGAGAACTGGCTATCCTTGGTGCTGACAATG
CCCAGGGACGTAGCTGGGGCCTCTGGTCTGTACATGAACCACTCGAAGTCTTGCTGGGCAGGGCCCTCATAGTCACTCACGTTGCAGGAGATAGAGA
CAGCGGTGCCAGCCACCCGGTAAAGAGGTCCCCTGGGGACATGCACCTGCCGGGCGTAGCACCTGGTTCCTGTGGGGTAAAAGCAGAAAGAACTGGA
ATCTTTTTAGAGAGAACGAGTCCCCACTTGATGGCCAGTATCATCAGCACCATTCTTGACTGCTGCCTGTGAAGGAAAGGGAAACCTAGGGATGGTT
AGAACATAGCTGGGCAAAGACACAGATGGGAACACAAGATGGGACACGAGACACCAGCATCCCAGCACATCACGTAGGTTCAGATCCACCTGAACAG
AGGAATACTCTAGCTAACTAGAGGCAGAGCACCTACATGAACAGAGGAGTCCATCCGGAGTCTGGGGTATAGACAGCCCGGTAAGTAAAATGCTTTC
CATGCAAGCATCAGGACCTGAGTTCAATTCCCGGCAACTATGGAAAAAGCTTGGCACGGTGGCTGGTGAGTAGCCACATAAGCCTGACAACCTGGGT

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

TTGAGCCCCACAAGGGAAGGAAGGAACTGAATCCTGAAAGTTGTCTCCTCTCTCTCTCTCTCTCTCTCTCTCTCTCTCTCTCTCTCACA
CACACACACGCACACGCACACGCACACGAATAAATGCAGTGGACGGTTCCTGAGCCATGACCCCTGAGGTTGACCTCTGACCTTTACACAGACACCT
GCACCCATGCATACATGTGGACCCTCATACGCATGCAATTGGAAATAACAAATAAAAGAAGCATGCCTGATTCCCAACTCTCCAGCTCGTGGCTGGA
TCTTTATCGCTCCTACCCTGCCATGTGTGGCGTCTCTCCGGGCTCAGAAAGAACTTCTAGCTAAGGGATTCTGAGCCTTTTGCTGGAGGGGACCTCA
CAACATCTTACAGAAAGGCTGCTTGGCTTAGCTCTGTCACCTGGGCTAGACAATGGAGCCAGTGGCCCAGGCTGGCTGGGGTACTGCACTGGATGGG
GCACCATGCTGGACAGGGCACGGACCTAGTCAGTCCTCACTACACAATACCCTCCCCACTACAGCTGTGCCATGAGCTCACTGCTTCTCCCAGCCCA
CAAGGCTACACAGGCAGCTGTGGCTTCTGGGGCAAGAACCAGGCTCTGCCCAGGCCTGGGGCAGAAGATCCCTTCCCCGCCCCCAGAATCTGTCAAC
CTTCTCGCTAACCCAGATGATGCACTATGCACAGCCCCCCAAACAAAAGCTTTCATTTACATATGATTTGCCTATCTGCGCAGCATTTGCATAGACC
TCCTTTTAATAAGGAGACCCCAAACACCTGCTGCCCCTTCCCCCTTCTCTCTCTCTCCCTCCCTCCACCCATTTTACCCCACCACTGTTCCAACAGA
CAGCCGGTTCCAAAACCTTGGACTGTTCAGCTTCTTTCTCCTCTCCACTACTTCTAGGTAAGACCGCAGAACCCTAGAATGCAAGACGGGCTGTCAA
TCATTCCTCAGATGAGAGAAATGAAGAAACTCCCAGAGAGCACCTCTAGGGAGCATTGCCACTAGGTTCTAACCACAGATGTGAGTCTAGAGCTCTC
TCCCAGCCAACACGGAAGGCCTGGCCGTGAGAACCATCTCTCTTCTAGATGAGAAAAGTAAAGTGAAATGTGACATTGTCGCCAAGTCCCTGCCCTC
TCTGGAGGGCCTCTACACACCCCTGAAGAGGGACAAAACCAAGAAGGCGGAGATGCTTCCAAGGAGAGCCCTGGTTTACAAAACTGTAATTTCCCGG
ATTTCCAGGGGTAAGTCCACAGCTTGCTACTGGCCCTGGAGGAAACCACCCAAGAGCCTGAGAGCCTGCTCTACAGTTCTCGCTCCTTTCCTTCTTC
TGGCTACGTCACGCAGAGAACACATGACCACCGCCTGAAGCAGAGGCTAGAGTCAGAAAGCCAACATGAGACCAACCCTTTCCTCTCCTGGATCTCA
GTTTCTATCTCTCAGAACTAAGAGCTCCCAGTTCTGATGTTGAACCCGTGAGTATATGTGTGTGACTCAGGCACATATCGCTCCAGGCACATTTCAT
AATCAGGAGGATGGTTAAGGCAGCCAAGCTGACACCATCCTGGCTGCCCATGGGTAAACTCTGCTGAGAAGGTCCCCTCCCACCTTCCTGGCTCCAC
ACAAGCTGATGCTTGGAGATCCCCATGGGAAAGTTGTCCCCACAGCCTCAGGACATAGGCTGCTACAAGGTTCTCAATGGCTGGGCTGCCTCCTTTC
TAACAGCCAAAGGTCTGCTTTGAAGTCAGTTCTGAGTTCAAATCCACCCCCACCCTCACTGGATACACAGTGGTATTTCACGACATCTGTGAAGTGA
ATGCCAGTGCTGGCTGCAGTGGGCTAAAATGACATTCAGCTCCTCTCCCGCCCCTGAATAACACTCACTCCTCCCAACCACCCCTGGGCTCATCCCT
GCTCGGGTTAAGCCCAAAGGAAAAGAAGCAATCGCTAGGCAACCAAGCCCCACAGCTCCTTCAACTCCCTACATCACTCTGCCTCCCGCCTTCTTCC
CAAAGGAGTTTTCATCCTGGCCCCAGAAGCCCAAGGAACCATTCTGTACAACACTGCACAGTTCTGGTATAAACCAGAGAAGGAGGTTGGGGTGCCC
CACTATAGTATCTTCTCCATATGCATATCACACACACACACACACACACACACACACACACACACACACGTTCCTTTCAAGGGCTTCAGTCTCCT
GGCAACTGCTCCATGCCATATCTTTCCCAGACCACCTCCTACAGGGAGCCCTCCAAGTCAGACCCCAAACATGGTAATGTTAGCAACCTCCACAGGC
CTCAACACACACACACTCACACTCACACACACACACCAGACATGACGCAAGGTTGGCCCAGAAAACACACCATCATAAACACCCACCAGGACAGACA
CTGGGTGCTTAGAGATCCCACGTTCAGTTTCCATGGAGCCTAGTTTCTCCTGAGGCACGGATGTTGGGACCAACTGAGTCTGACAACCAGGCAAATA
TCTGGGAGCGTGGAAGGGCAAAGAGGGAACTGGCCCAGGGTGGAGACACGTGAGGGAAGAAGCCTCAGATGGTGACATGTTATATTGGGAGGTGGGG
GTGTTGGGGAGACTTTTTTCAGAGATCGTGGTCAGAATCAGCCCCTGGGCCTCCAGCCAACTCTGGGCAATTATGAAGACCGCCAGGCACTGCCCAC
GCAGAGCAAACACCCAAAACCAGGCCTTGAGCCGAGAGTGGGGCAGAAGGTTGTCACGGTATTTGGTAGCAACGACCCCAGACGCTGGGTGTAACCG
ATGAGAAGTGGTGCCTGCCTCCGGAGGCCCGATGGTGTCTCAGGGGATACCTCAGTAGGTCGCCCATATGCCCCAGCTAGGAACCTAGAGCGAGGAC
ACCACCACCCTCCCCATAACTGATTGGGCAGACAGGCGCAAAAGGAAGCGAGACGCCGAGCCCAGAGACAGTGGAGGCACGTCTGTTGGAGAAGTAG
GGATGCAACCAGCTCTGAAATGCTACGAAGGTGGGCTGGTGGGCTCCACTATGTTAGGCACCTACCCGGCCGGGACAGGGACGCGGCGACCACCACC
TGGCTTACCAAGTATTAGCAGCAGCAGCAGGAGCGAACTCAGCGGCGTGGGGCTAGGGACGCCCATTCTGCGTAGGCGGCTCTGOGGAGACTCCTGG
GGGCGGCGTAGGCTCTGGGGGGCCAGGGCCGCGGGGGGCGCATGCCCAGGTGGGGGGCAGAAAGCGGAGCAGTGAAGCGTGGGTGCGCAGAGCCCAG
CCGAGCGGGAGCCGCCAACTCCCCGCCCTCCACCCTTCTTCCCCTCCTCCCTCCGCTCTTCCCGCCCTCCGCAGCTCGGGAGACCAGTCCCAGCCGC
GCCCCGCTGCCCGGCCCCGCCCCCGCCTCGCCCCGCCCCAGGCCGTCGCCTCGGCCAGACTTCGACCCTGATGGTGGCTCCGCCTCTGGCCTCAGGC
TGGGCGAACTGGCOOCACCTGGGCTCCTCTATCCCCATTTCCTCGCTCAGACOGCACCCCGCCCTGCACCTGCCAGCCTTCCAGGOAGAATGGGGTG
CTTTCAGGGCCTCTGGGGATGCATGATGGGGTGACTGTGGTTACGCACTCAGAATCCAATTGGG

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

MOUSE SEQUENCE - mRNA (SEQ ID NO: 2)

CTGAGCTGCCGTTACATTCAGGAGAAACAGCAGTGTCGGCGGCTCCCAATCTCAGAGGGAACCTAGGGTACTGGGGGAGATGGTGTCAGGGACATGG
ACGCCAACCCCCAAGGGTTTCTGCTGCTGGCTACTCTTCTCTCCAGGCTCTACTTCTGTTCATACGGTCCATATCTCCTAGGGGACCCTGAAAGCCT
AGGAACCGACTCTGGCCATCCATCTCTCCGGGAAGATTATAACCCAGAGTGCTTCTCAGGGGGGAAGAATTTGAAGCAAAACCAGACCCCGCAGGAT
CCCCGCTGCGGCCGCCATGGCGCAGGAGAACGCCGCTTTCTCTCCCGGGTCGGAGGAGCCGCCACGCCGCCGCGGTCGCCAGCGCTACGTGGAGAAG
GACGGTCGCTGTAACGTGCAGCAGGGCAACGTCCGCGAGACCTACCGCTACCTGACCGACCTGTTCACCACGCTGGTGGACCTGCAGTGGCGCCTCA
GACTGCTCTTCTTCGTGCTCGCCTACGCGCTCACTTGGCTCTTCTTCGGTGTCATCTGGTGGCTCATCGCCTACGGTCGCGGCGACCTGGAGCACCT
GGAGGACACCGCGTGGACCCCGTGCGTCAACAACCTCAACGGCTTCGTGGCCGCCTTCCTCTTCTCCATCGAGACGGACACCACCATCGGCTATGGG
CACCGCGTCATCACCGACCAGTGTCCCGAGGGCATCGTGCTGCTGCTGCTGCAGGCTATCCTGGGCTCCATGGTGAACGCTTTCATGGTGGGCTGCA
TGTTCGTCAAGATCTCGCAGCCCAACAAGCGCGCCGCCACTCTCGTCTTCTCCTCGCACGCCGTGGTGTCTCTGCGCGACCGGCGCCTCTGTCTCAT
GTTTCGCGTGGGCGACCTGCGATCCTCACACATCGTCGAGGCCTCCATCCGAGCCAAGCTCATCCGCTCCCGTCAGACGCTCGAGGGCGAGTTCATC
CCTTTGCACCAGACCGACCTCAGCGTGGGCTTTGACACGGGGGACGACCGCCTCTTTCTCGTCTCACCTCTCGTCATCAGCCACGAAATCGATGCCG
CCAGCCCCTTCTGGGAGGCATCGCGCCGCGCCCTCGAGAGGGACGACTTCGAGATCGTAGTCATTCTCGAGGGCATGGTGGAGGCCACGGGAATGAC
GTGCCAAGCTCGAAGCTCGTACCTGGTGGATGAAGTGTTGTGGGGACACCGGTTCACATCCGTGCTCACCCTGGAGGATGGTTTCTATGAGGTGGAC
TACGCCAGCTTCCACGAAACCTTTGAGGTGCCCACACCCTCGTGCAGTGCTCGGGAACTGGCAGAAGCCGCGGCCCGCCTTGATGCCCATCTCTACT
GGTCCATCCCCAGCAGGCTGGATGACAAGGTGGAGGAAGAAGGGGCTGGGGAGGGGGGCAGGTGCGGGAGATGGAGCTGACAAGGAGCACAATGGCT
GCCACCCCCAGAGAGTGAGTCCAAGGTGTGACTGGTTTCCTCCCACCCCCTGTGGCAGACCAGGGGGCCGGACTCAGGTACACAGAAGCTGCGAGTG
GAGGTGGAAGAAGAGGAGGCAGGCAGTGTCCCGAGGAACAGCTAAAGTTGGGAGAGGCCCGCTGAGTCCAGGATCGAGTAGGGAAGGCTGAGGTCCT
GGTTTGAAGAGAGAGGGTTGCAGGGCGGGGTGAGAGAACATGTCAGTCTGTCTGTGTTTGACCTTCACATCGGTTCATGGGTGGATGGATGGACAGA
AGGATGGGCTCATGGGGGTTGATCGGGAAGGTGGAGCAGATAGAGACAGCCAATGGATAATCGCTCAGGTGGTAAGTGGCTTGGCAGTCGATGATCG
TCACCTGCAGCACACCTTTGTGAGAAATCCATGGGCATCCTTTTCTTCCAGATATAGGTAGCCTCAAACCAGGGAGCGTGGCTTAGGGAGCAGGCTG
TCAGGTGGACTACCACCCCCACTCACCTCCCCTCAACTGGCCTCCCTGATGTGTGACACGCCTGCCTAACTAGAGAAGAGAGCACTGGGTAGAGGTG
GACACAGGTGTGGCTGCCCTCCCCAGTATCACTGTCCCATGGCGAGAGGTCAGAAAGGCAAACAAACAATGGGGGTAGATGCTGAGCAGGGAGGGGC
CCTGAAGCAGGACCTGGGGACAGCCAAGGACAACTATTTTGTGAGAGAGGAATGAAACCTTGCAGGTCCTGCCACAGAAGCAAGAAGCAGAGGAAAG
GCCATGGAGAGACTTAATAAAGGGTTTTACAAGGGA

MOUSE SEQUENCE - CODING (SEQ ID NO: 3)

ATGGCGCAGGAGAACGCCGCTTTCTCTCCCGGGTCGGAGGAGCCGCCACGCCGCCGCGGTCGCCAGCGCTACGTGGAGAAGGACGGTCGCTGTAACG
TGCAGCAGGGCAACGTCCGCGAGACCTACCGCTACCTGACCGACCTGTTCACCACGCTGGTGGACCTGCAGTGGCGCCTCACACTGCTCTTCTTCGT
GCTCGCCTACGCGCTCACTTGGCTCTTCTTCGGTGTCATCTGGTGGCTCATCGCCTACGGTCGCGGCGACCTGGAGCACCTGGAGGACACCGCGTGG
ACCCCGTGCGTCAACAACCTCAACGGCTTCGTGGCCGCCTTCCTCTTCTCCATCGAGACGGAGACCACCATCGGCTATGGGCACCGCGTCATCACCG
ACCAGTGTCCCGAGGGCATCGTGCTGCTGCTGCTGCAGGCTATCCTGGGCTCCATGGTGAACGCTTTCATGGTGGGCTGCATGTTCGTCAAGATCTC
GCAGCCCAACAAGCGCGCCGCCACTCTCGTCTTCTCCTCGCACGCCGTGGTGTCTCTGCGCGACGGGCGCCTCTGTCTCATGTTTCGCGTGGGCGAC
CTGCGATCCTCACACATCGTCGAGGCCTCCATCCGAGCCAAGCTCATCCGCTCCCGTCAGACGCTCGAGGGCGAGTTCATCCCTTTGCACCAGACCG
ACCTCAGCGTGGGCTTTGACACGGGGGACGACCGCCTCTTTCTCGTCTCACCTCTCGTCATCAGCCACGAAATCGATGCCGCCAGCCCCTTCTGGGA
GGCATCGCGCCGCGCCCTCGAGAGGGACGACTTCGAGATCGTAGTCATTCTCGAGGGCATGGTGGAGGCCACGGGAATGACGTGCCAAGCTCGAAGC
TCGTACCTGGTGGATGAAGTGTTGTGGGGACACCGGTTCACATCCGTGCTCACCCTGGAGGATGGTTTCTATGAGGTGGACTACGCCAGCTTCCACG
AAACCTTTGAGGTGCCCACACCCTCGTGCAGTGCTCGGGAACTGGCAGAAGCCGCGGCCCGCCTTGATGCCCATCTCTACTGGTCCATCCCCAGCAG
GCTGGATGAGAAGGTGGAGGAAGAAGGGGCTGGGGAGGGGGGCAGGTGCGGGAGATGGAGCTGA

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

HUMAN SEQUENCE - GENOMIC (SEQ ID NO: 4)

GGAGTAGGAGAAAGCTATGGCATTTTAGGAAAATTAATCGGGAGGTGACAAAATAGTTTGAACCAAGTGGATATAGTAGGCAAGTAGACGATAGAAA
ATAATTGCAATAATATAAGCATGAAGAGATGACAGCCCAAATCAGCGTGGCAATGGTGAAAAGTGGAACACAGAAAATGAATTGGAGTACAGAAAAA
TCAAAAGAAAATGAAAAAAGTTTGAAGCCAACTTGACATGTTGAGCAAAAGAGGGAAGCTTCAGAGATCATACTAGAGTCTCAAGTCAGGTGATCAG
AACTGCGAGGTCATTCACGGGCATAGGGGAGCCTGGGGGGGATCACACCTGGTGAGGAGACTGAGGTGGGGGAAGAGGAAGTGATGAGTTCAGAGCT
GGAAGCTGTGGAGAGGGGTCAGAACCAGAGAGAGAAAGGAGGTCATTGCTGCCAGGGCAGTGTGAGTTGAAGCTATGAGAACAGGGTAGATCCCAAC
AAACACTGCACAGAGAAATGAGAGCCTGGCACAGAGAGTGAGGAACACCTATGTTTAGGGGATGGGAAGAAGAAGGACCCCCAAAGAGTGAAAGAGA
ATCCACCAGACAGGCAGGAAGGAGACAAAGAAAGTGAGATGTCATGGAGCTAAGGAAGGAGAGACTGTTAAGGAGGAGGTTCTAACAGTGCCAACAA
GTACAGAGAGAAGAGGCATTGGGTTTGGCAGTGACAAAGTCTCTAGTGACATTTGAGAGCAATTTCAGAAGAGTGAGCAAGGTGGGAACCAGATTAC
AAGTTACCACTAGAAAGTGAGAAACTGTCAGCAAGTATAGGTTACACTTTTGAGAACTCTACTCATAGAGAGGAGAGAAATAGAAACCAGACAATGT
ACTAGAAACAGGCCAGGCCAGGTGGCTCATGCCTGTAATCCCAGCACTTTGGGAGGCCAAGGTGGGTGGATCACCTGAGGTCAGGAGTTTGAGACCA
GCCTGGCCAACATGGCAAAACCCATCTCTACTAAAAATACAAAAATTAGCCGGGCCTGGTGGCACGCGCCTGTAATCCCAGCTACTTGGGAGACTG
AGGCATGTGAATCGCTTGAACCTGGGAGGCAGAGGTTGCAGTGAGCCGAGATCACGCCACTGCACTCCAGCCTGGGGGACAGAGCTAGACTCTGTCT
CCAAAAACAAAACAAAACAAAACACAAAATAAAAAGAAAAAGAAACAGTCTTCCAGTTTTTCTTCTTCACACTCCGAATGCCCTCTCTTCCTAAGTC
AATATGGATGAGGGGCTGTGGTGAGGTGGTCTGAGGGCCAGCCTGCAAGACTGGTATAAGACCTTTAAGTTTCAAAAAATAGGACATCCAAAAGATC
CTTAAGGGGGCCACAGTCTTGACATTCACAGACAGAGAGGACTTAGGCAGGGGTGTCCAATTTTTTGGTTTCCCTGGGCCACATTGGAAGAAGAAGA
ATTGTCTTGGGCCACACATAAAATACACTAACACTAACAGTAGCTGATGAGCTTTAAAAAAAAAAAAATCACAAAAAAAAACCCTCATGATGTTTTAAG
AAAGTTTACAAATTTGTGTTGGGCCTCATTCAAAGCTGTCCTGGGCTGCATGCAGCCCACAGGCGGTGGGTTGGACAAGCTTAGCTTGGAGGCTCTG
GTGGAACTCCAAAATAAACATGAAGAACACCACAGAAGAGAAAGCAAAGGGACTGTAATGATTTATGGATCATTAACAGACATTTATTGTGCACTTA
TTATTTTTCCAAAAATGTTATCCATCCATTTAGCTTCAACTACCACCCATGTGTCAATATGTCCAGCCCACCCGGATATCCATTTCAAACTCAACAT
ATTTAAAGTCGAACATGTCACCTTGCTCACAAGAGTGCTCCTCTCCATTTATTCTCTACCATGGTAGATACACTATCATCACCCAACCAGAAACATG
GCAGCCATCCTAGATTCTTCAATCTTCCTCACCTCATCTCCCTTATTGAATCAATGCATCTGTATTCTAAATAGCCTCAATATTGTCCCCTTCCTCT
CTATTCCACTATCATTGCTGTAGTCTAGGACACCATTACCTCTCACCAGGTAATAATAGTTTGGATCTTTGATCCTGCTCAAATTTCATGCTGGATT
TTAATGCCAATGCTGGACATGGGCCTGGTGGGAGGTGTTTTGATCATGGGGGCAGGTCCCTCAGCGGCTTGGTGCTATCTTCATGATAGTGAGTTCT
TGTGAGATCTGGGTGTTTAAAAGTATATGGCAACATCCCCCATCATCAACTCTCTCTTGCTCCTGCTTTTGCCATGTGATGTGCCTGCTCCTGCTTT
GCCTTCCACCACGAGTAAAAGCTTCCTGAGGTCTCCTGAGAAGCTGAGCAGATGTCAGCACCATGCTTCCTGTAAATCCTGCAGAACTGTGTGCCAA
TTAAACCTTTTTTCTTTATAAATTACCCACTCTCTGGGTTTTTTTTTTTTTAATTTTTAATCTTTTTTTTTTTTTTGAGACAGGGTTTCACTCTGTC
CCCTAAGCTGGAGTGCAGTGGTGTGATCACAGCTCACTTGTACCCCTGAACTCCTGTGCTGAAGTAGTCTTCCTGCCTCAACCTCAAACGTAGCTGG
AACTACAGGTGTTCACCATTACACCCAGCTATTTTTTTTTTTTTTTTAACTTTCAGTAGAGACGAAGAATCGCTATGTAGATCAGGATGGTCTTGAAC
TTGTGAGCTCAAGCAGTCCTCCCACCTCAGCCTCCCAAAATGCTGGATTACAGGCTTGAGCCACCATGGCCTATCTCAGGTATTTCATTATAGCAAT
GCAAGAATGGCCTAATACACCAGGGCTACTGCAGCAGCCTTCTAACTACTCTCCCTGCCTCCAGTCTTCCTCCACTCTAATAATTCTTTGGATTATG
AATTTCTTTATTTGAAAGTAATTAAGCACCAGTAAAGTACATCTCTCTGAAACACACATCTGACCGTACCACTTCCAAGTTTTAAAACCTTCAGTAA
CTGCCAACTATCTATAAGTAAAGTCCGAGTTCCTTTCCCTGGAAGAGAAGGCCTATTATAACCTGGACCTGGTGCCATTCCAGCCTTATCTTCTTCC
ACTGCCCCTATACACCCAAAGCTACAGCTACTTCTTTTAACACTCAAGGTTCAGCCTTATGTTCTCTTTCTGTGTCTTGCCCCTTGAGCCTTTGTCA
TTTACATAGCTCCAACGATTGTCCCTGAGTGATGCCCAAATCTCTATCTTCAATCCTACACTCTCTTTGGACCTCCATATTTCTAGTTGCTTGCAGG
GGATTTCCATCTTGACTTGACAGGCCCCAAACTGAACTCAGTACCTTCCTCCCCAAAGGTCGAAGTGCTCGTGACTTCCTTAGTTCTGTGTTACTCC
TGGTCAATTAGAATAAAAAACTACAAGTGACCTTTACTCTTCACCGTTGCCTTGGGCCCATTCCTGGACATGTCAAATAAGCCAACAAATGCTGTCA
AGTCTCCCTTTCTTTCATCTGTTTGCAATGTGCTTTTTCATTCCTATGACCACTATCAGAATCAGAAAGATCAGGACCTGACCCATCCTTCACCTTT
CTCTCCAGTCTCAAAGGAAGAGGCAACCTGTTTTCATCATGTCGGTCCCTGTGCCCTTGTTTTAACCCCAAACACAGTTGCCTCGTGCTTACAGGTC
ACAGTGAAGGAGGTCTTCACCACAGAAGACCTAGAAAAAAAAAAAAAGAAGATAAAAAACGTGACAGGCCCTCAGACTGAACTCGGCATCTTTCTCTC

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

TGAGGCTGGAAGTGCTCATGACTTCCTTAATTCTATGTTACTTCTGGTCAATCAGACTAAAAAACTACAAGTGATCTACAGAAGTGTCCTCTACTAA
CAATCAGAGTGAGGATAGAGTCGGGTGGGACTGGGCAGTTAGAAAGACTTTATAAGTCCTTGAACAGCAGGGGTGGGAGCTTGTGGAAAAGTACACA
GGTAGCTTCAACAGCACTGTAATGTTCTGAATTTAAAAGAGTGACTTAAATTGAGTTTTTGTTCTTAAATTATGCTTTATAACATATAGACATATGT
CCACCATCTATATTCTTTTGTACATATCAAATGTCAGGTTTTCATTTTTAAATTTGTTTGCAAAAGAGAAGTCCTAGGACAGTCTCTAGGAGCCCAG
TAGGGAATCAGTAATAAGGGGCATAGGACACTAATATTTGTGAGTGTTTACTACATCAGATAGATCAGAAGATGGGGAAACTGAAGTTCTGAGGAGT
TAAGTGGTTTGCCTATGGTAACATAGCTGGAAAGTGTTTTGAGATTTGAATCCACATATATTTGACCCCAAAGCTTGTCTCAGAATAATGCCAGAGG
GAATTTGCACGTTTTAAACACAATCTTGCCAACCAGAGGCTATGACCCCTGAGTACATGTTGGTATGAAAAATTCCCCAGAATTACAACATCCAATG
TCCACCATGAAACATGACAGAGGAAACTTCTCTTTTTGAAGACCCCTCTCTCTTCTTTCAGTTTCCCAACTTGCGTCTTCCTTATTCTCCTCCATTT
CTCCTTTCAGACTCACTGCTTCCAGCTTTGGCCTCATCTCTACTTTTACTTCATTTGTAATGGGGCAGAGGCTACCTCAGAGCAGAGGAGGAGGAGA
GTTGGGGCGTGTCACCTGTTTTAGAAAGAATCCACAAGTGGGCAGCAGTCTGAGGGGCTTGCGCTGGGCAAAGCAGATGTGGACAGAGGGAATCAGG
AAAGCTTTGGGTTGGGAGGCATGATAGAGACTCAGAATAGTCAGTATTTAACAAGTCACGGGAAGTGGCTAGAAAGAACAGAGACACTGGCATGGCT
CACCACAGGATTCAGGATTCCAAGTGGCGTTTTGGTGCTCACATCCCACAGTGCGGAACAAATTCCATTAGTAGTGGAGCATCTCATAGCTGAATGA
CTCAGGCCGCAGAGGAGAAATCCAAGAGAAGGACTGAGCTACATTCCCCTAGTCACTAACGAATCATTATGTAAGTAGATCACCCCCTTTAAATAAA
TGCAATATACACAAACCCACATTTATAAGACATAATTTAGGGAATACTTAGTTACCTACTAAAGAATTCTTTCCTTTAAAAAAGAAAAACATGGCCA
GGCACGGTGGCTCATGCCTGTAATCCCAGCACTTTGGGAAGCCAAGGTGGGTGGATCACCTAAGGTCAGGAGTTCAAGACCAGCCTGGCCAACATGG
TGAAACCCCATCTCTACTGAAAATACAAAAAAAAAAAAAAAATTAGCCAGGCATAGTGGTGTGTGCCTGTAATCTCAGCTACTCAGGAGGGCGAGGC
AAGAGAATCACTTGAATCCGGGCGGTGGGGGTTGCAGTGAGCGGAGATCGCGCCACTGCACTCCAGCCTGGGCAACAGAGCGGAACTCTGTCTCAAA
AAGGAATAAAAAAAAAGGAAAAAAGAAAAAAACAAATTTCTCTAACTAGGGACTTCTAGTACCTTTCCAGTTGGGTCCAATTGATAGAAATTCCATT
AACATCCAATGCACTGTGATAGGAGGGAGGCAACTGGGAATAAAGAAACACGAGGAATCTCGAGTCGGGTGGCCTGAGTCTTAGTCCTGACTATGTT
CTTGGGACCTATTCCTACCTGTAAAGTAAGGGCTAATCCTGTACCACCTCTAACCGTCATATAACTTTTAAATCTTAGCCTATCTCTACCCAGTCCT
ATAAAGCAAGATAGAACTCTGTGTGAAGGCTTCTGATCCTCCTGCTCTGCTGAAAGTAGCCAGAAAGGCAGCAAGCTCCTCAGCCTCAGGAACCCAG
CCTGAGGCGAGGGGCTGGCTGAAATTGCCTCCGTCTGGCCTGGAGCTGTGCTCTGCTTCTCCCCATTTCACTCTAATCTTCAGCTTCAGTCATTTGC
CACATCTACTCCTTCAACCATATCTTTCCTCTGCTCTGAGTTTTCTAGAGCCCCATCCCCCTTGAATTTATACAAATTTTTGCAATCAACCAGATTG
GCCTCCCTGCTCCACTAAACTCATATCCTCAACTGTCTGCTGTCTTCCCCATCATGCTTCCTCTTCCACTTGCCAGATTTTGCACAAGATGTCTCAT
GATCTTGTCCAGGGAAGCCTCCCCAGTTTGGCTGATCTCAGGGCTGCCACAAAGGCACCTGCTGATGGGGCAAGTTGAGGACTGAACTGCATTCAGC
TTGCCAATTCCTGCACCCAGCTCAGAGCTGTGTCTGCTGGAGGAAGGGAACCTTTTATTTTCTCCCAAAAGTATCACCTGTTCCCTGTTCTCCAAGT
GACAGGCCACAGTAGGCTCTTTTTAAGCTCTTTTCCTATTTTGCACCACGGTTCCCTTTTTTTTTTTTTTTTTTTTTTTTTTTTTTTTTTTATGAGACAA
GGTCTCACTCTGTTGTCCAGGCTGGAGTGCAGTGGCGCAATCACGGCTCACTGCAGCCTTGAGCTCCCAGGCTCAGGTGATCCTCCCACCTCAACCT
CCAAGGTGGCTGGGACCACATGCACATACCACTACACCCATCTAATTTTGTATTTTTTGTAGAGACAGGGTTTCGCCATGTTGCCCAGGCTGGTCTC
CATCTCCTCGGTTCAAGCGATCCGTGCACCTCAGCCTCCCAAAGTGCTGGGATTATACGTTCGAGCCACCGTGCCAAGCCAAAAGCTAGAATCTTGT
CTATGCTTTTGTGTCCTCGTGCCTGGGAAAACTTTTTTTCTCCTGCCTCAGTTCAGCTCAGTGATAAATAAGGAACTGAGGTTAGATAACAGGTAAA
GTCTAGGACCTGCAGGATGAGTGAATCAGGTGAGGGAGTGGTAGTCTTCTTCCTTGTCAGCCAGGCTAGGTTCAGGGGCACCTGGACTGAGGCGAGG
GGCTGGCTGAAATTGCCTTGTGGAGGGCCCTGCCAGTGATGCCCCCTCCAGCAAATAGGGCCAGCTCTATGCAAATGTGTTCTTGCCCAGGAGTTTG
GTTTCTTCTCTCTGAGCTCCTGGCACAGTGGAACCAATGTGAGCAGCTGCTTGGCAGGACAGAGAAGGGCAGGCTAGCAGTCCCAAAGCTCGGGTGA
CAGGACCAGGCCCAGGAGACGGGGATGTTGACTGGGGCTTTAACAGCACTCTTGATGCCAATCTCGGGCTGAAAACTCGATATTTCCACTTCGAACA
ACAAGAATCACCAGCAAGAGAGCTGAGGAGAGGGCAGTATACCGGGGGCGCCCCCTGCAGGCCTCACAGGGTGGTGCCAGAACAGAGGAAGGTGGCA
CAGGCAGGGTGGGGCTTTCAGGACATCCCTGAGATGATGGTGATGACGGTGACAATGATGATGACCATGAAGAAGACAATGAGGAGGAGGAAGAGGA
AGACAGTAGCTAGCATTTACTGAGTACTAACAATGTGTCAGGCATTGCCTTATGTAGTCTTCATGACAACCCTCTAAGAGATGAATAATATGGTTTT
CTTTTTTTTAGATGAAGAATCTGAGGTTTAACGGGTTAAATAATTGCTCAGGTTCACCCAGCTAGTAGTGGACAGAGGTGGGATTTGAACCCAAGTC
ATTGCCTCCTGAGCTTATATTATCCAGTACCGAATTTCCCACCTTGCCAGGTCATTCCACGAGCTTCTAGCCCTCCGTGTCCATCTCTATGTCTTCC
TGCTCCTCTAGCTCATATTTTCTTGATCCAAATTTAAAGGATCTGGATAAGAATAGATCCATATCTGGGATATAATAATACTGATAACAACAGCAAC

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

AACACTTTGCGTTTGTAAACCACTTTCTTCTCTTCATTATTTCCCTGGGGAAAAATAAACAATAAGATATTTCTGTTTCTCCAAATTTTGTTCTGAT
TTTTATCAGTGTTCCTGAAGCTATTTCAATATAGTCATGATCAATTTCTAAGAATATTTTTAGGTTCTGCTTTTTTATGTAACAGTGTGTTATATAC
ACATTCACATATTTAAACACAGCAATTATTATGGCTTTACAGTAACCCATGATATTAATATTCCACAGATATTACATTACTGAGGCACACTAGGCTA
AGGCTGACAACACCAAATGCTGGCAGGAATGTGGAGCAACAGGAACAGGAATTCGTGGCTGATGGGAATGCAAAATGGTACAGCTACTTTGGAAGAA
AGTGTGGCAGTTTCCTAAAAAACTAAACATACTCTTACCATACGATCCAGGAATCATGCTCCTTGGTATCTACCCAAAGGAGATGAAAACTTACGTC
CACATGAAAATCTGCCGATGGATGTTTATAGCAGCTGTATTCATCATGGCCAAATCTTGAAAGCAACCGAGATGTCCTTCAGTAGGTAAATAGATAA
ATAAACCATGGCCATCCTGAAATGGAATATTATTCAGTGCCAAAAAGAAATGAACTACAAAGCCATGAAAAGACATGGAGGAACCTTAAATTTACAT
TACTAAGTGAAAGAAGCCAATTTGAAATGGCTACATATTGTACAATTCCAACGACATCACATTCTGGAAAAGGAAAATTATGGAAACAGGAAAAAGA
GCAGTTGTTGCCAGGGGTTAGGGAAGGGGGATTGACTAGGCAGAGCATAGAGGACTTTTACAGCAATGAGACTATAATGGTGGATACACATCATTAT
ATATTTGTCCAAACCCACAGAGTGTACAACACCAAAAGTGAACCCTAATGTCAGCTATGGACTTTGGGCGATTATGATGTCAATGTAGCTTCATCAC
TTGTAACAAATGTGCCATTCTGGTGGATGTGTGGGGACAGGGGGCATACGGAAAATCTCTATAACTTTCCTCTCAGTTTTGCTCTGAATCTAAAACT
ACCCTTTAAGAAGTCTTCTTTTAAAACAATTTACAAAGCATGAGGTGATACAGATGTGGGAGTTTGGCTCCTGTCTCTGCCCAACTCTGTGACATTC
GATAAATTACTTAACATGTCTCTGTTTCAGTTTCCTCATCTATAACTGGGAAAAATAACACCTGTCTTATAGAGTTGCCATGGGGATGACATGAGGC
ATGTGTCTCGTTCATATCCCATGCTCAGTGAATTAGTAGCAGCAGCCACTGTCTGTTTGTGTGTCTTTATCCCTCCTGGGTTAATGAGCTCCTTGTG
GGCAGGGACTCACCCATTCTGTAACCACCCCATCTAACACACTGCCTGGCACTTGCGCTCCGCAGAAGTTTGCCGAGTGAATACTTAGTAAGCCCTA
ACCTAGGCTTTTCTCTCTGGTGGACATTTGGGTTGTTTCTAGGGTTTTTGCTATGAATAAAACACATTTCAAAGCCCTTTGTGGTTTTTTTGGTTTT
TGTTTGTTTGTTTTTTCTTCGTTTGATCTGCTGACTCTGTGAAGCAGGCAGAAACGGGATATTTGCTCTTGTCCACACCCTGGTACAGATGCAATAA
CTGTGGCTCAGGGAAGTGAAGTCACTCCTATGGGACACAGTGCAAATCAGTGGCAATAATTAGAACCCCTGACCCTGCCTCCCTTCCTTTAGTAGAT
CTATTTTCCTTCTAGCTACCGCCTTCTGGATCCATGGCCTCTCCAAAACTAGACCATGATGGTCAGCCTGACCTGAGAGCAGCACCTGCACGCAGAG
ACCCATGTTGAAGGTGGTGAGCTGCCAGCTACCAGATGGCCCTCTGAAACCCCAGGGAACCTAGCACCTTATTCTCAAATACATGAGGGCTTGTATT
TTCCCCCAGGAAGGAGCTTCTTAGGAAAGAGCCAGCGTGCCAGCTTTGTTTTTCTTTCTTCTTCTTTTTTTTTTTTCCTATGAGGGGGTGAGGAGC
CAAGCTCTGAGTTGTCCAGGAGGAGGGACTTTGGCTAAAAATAGCTATGGCGTGTGGTTTGGATCAACCCCTAGTGGTACCCAGGACTGGGGAGGGG
AGGGGGATCCTCTCGAGCTGTCGCCAGACTGGTTGCCGTGGAAACAAGAGAGGAGCACGGGAGCCTGGGAAGTACGGATGACACAGATAGCAAGTCC
TAGTCAGAGCTGCCGCTACATTTAGGAGAAACAGCGGTGTCTGCGGCTCCCACCCTTCGGGGGGCCCGTGGGGGGGGCGGTGTCAGGGGCATCGACG
CCACCCCCCAGGGGTCTCTGCTGCCGGCTACTCTCCTCTCCACGTGCTGTGAGTTGAGTTGCGGGGGACTTGGGGTTTGGGCCCCTATTTCCAAGGC
AAGTGGGGGTTTGGGAGGAGCTGGTTCTTGGGGGAGTTTTCACCAGGTCTCTCCTTCCAAAAAATGAGCCCCCTTACTCCCCAGCTCTCTAGAGGGA
GGAAGAGGGGCCCAGGAAAAGTGGTATTGCAATCTTCTGCAAAGGGGTCATAGCATGCACAAGAAATGAGGAGTAGGTTGGAGGAACTGAAATTCTT
GGAGGGAAGATGGAGAAATCAAGTCCTTGATCTTGAGATAGAGGTAACAATTTCACACTTTTCCTTCCCCTGAGAAAAGTGCAGTCCCCCACTCAGG
AAGACAGGATGTGGGACACATTCAAAATAAGGTTTACCTAGATCCCTGGGGCAATGGAGAGTCAGAGAGTTCTGGGGGTGATCCGACATCGGGGTTC
CTTCCCCATCCCTGGGCAGACAGATCTGTCTAGGCAAGCCGACTGGGCGTCAGATTACCTAAGACCCTGAGAGAACATCTGGAAGCCCACCTGGGAC
TAAAGCTAGGATAATGGGAGCAGGGTCGTTTTCTGCATGACCTGGGGTCTCTGAGCCAGTCAATGCTTACTCTTCCTGAGGACATCTGAGCTTCAGG
AAAGGAAAAGGAAGCCCATTGTTGGGGGCAGGGGAAACCCTAATCTTCCATTGCCATGGGGCTCTTGCACCCTGTGTCCCCTGACTCCATGGACAAT
AAATGCAGGGGGTGCCCCTAAGCTCAAAGCCATTTCATTTTGATTTCTCTTCCTACCTTCTCTACCCCAAGACACACAAACACACACACACACACCC
TCTCCAGAGTGCTGACTGCAGAGGACCTCACCCCAGAACATAAGATGCTGGAGTGCTAGGTTTAGAGTCACATACCCAGGCAGTTTCTCCCCAGGAC
CTGGTCAACCATCCACGCCATCTGTCGTTCCTATGGCACACTCCTCCATCCCCCACCCACTAGCCAGCCCACGTTTCCGTCGAGTGGGAGGAGAGGA
TCATTCCCAGGAAAGAGAAGGGAAGGTGGAAGAGTCCCAAATCCTATTCTAAACCTTTCCCTGTATGGTCCATATCTCCTAGAGGACCCTGGGTGCT
TTGGGGAAGGGCTCTGGACCTCTCTCAGAGCAGATTGCAGCTCAGAGAGCTCCTCAGAGGCAAGCATGTGAAGAAAAATCAGGTGGGCTTCGCTTGG
AATGTGGGCTTTGGGGCATATGGCAGGTGGGGGCGGGGCTGGTGTTAGGATAGTCCATGGGAAGTAAGAGGCTGGGGGAAAATATAACTAGAGGGAG
TGGGGAAATAAATGTGGGTGCTTAGTGCTTCACCTGATCTGATTCCATGTCTCTCATGAACAATAGGATCCCAGAGGGATACGAGCCTAACTCTTTA
TAACTCTGGGCTTCCTTTCCCAGGCTTCTGTGTTGGGATCTTCCAGTTCCCCTCCCCATTTGCAGGCTGTCTCCACTAGGAGAAAAAACCCAAGGGA
AATGAGGCTGGCCCAAGAGCAGCAGTGATCGTGGGTAGGTCTCAGGGAGGATTTCTAGTGGGAATTTCCTAATGTTCCACCCTTGTGCACTGGAGGG

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

TTTCCACTGACTTTCCACAGCTTTCATTTCTTTCTCGTTTGTAAGCATGTTGAGGGGAGGGAATGGAGCGGAGTGAGTGAGGTCCAAGGAGGGAAGA
ATGAGAAAGACTGTGTATCAGTCTTGGGGTGAACTTCAAAACAGCCTGCGAGGAGAGCCATTGGTGGCTGCACTGGCTACAGCTGGGGAAGGGATGG
TGGAAGTCCTTAGGGCAGGGAGGGCTCCATTACCCGCCTGCCCCCTCCCCAAAAAGCCCCCAGTCTATTGATTTCAGGAAATCACTAGGGGGATCT
GGGCCTGGGTCTTTGGCCCCGGGGCTGCCCCTGAGGTGCTGCACACCCCAGCTGGAGGTGATGGCACCAAAATATCTGGTACCTCCTTCCCCTGAAA
ATCATCGTCGAACTTGCACAGTTCTATCCAGTTCAGGTACATCATTCCATTTGACCCTCACAACTTTCTGAGCCTGGGCGGCAGTTAGGGCTGAATG
TGTTATTCCCAGAAATAGAGGCCAGGCAACACGAAGGGACTCGCCCAGGGCCCCCCAGGGCTCGGTGCTGGCCCTGATGCCCCGTGCCTCCCCATCT
CCCGAGGGGCCACTCATTCGGCAAACCTTTATTAAGCCCCTCCAGGACCCCCGACGCCGCCTAGGCGCCCAGCGACGCGCGGCAGGTGGCAGCAGCT
CGGGCCCCCGCCGCACTCCAGGCGCCCGCAGCGCTCGCCCTGACGCGGCCGCCATGGCGCAGGAGAACGCGGCCTTCTCGCCCGGGCAGGAGGAGCC
GCCGCGGCGCCGCGGCCGCCAGCGCTACGTGGAGAAGGATGGCCGGTGCAACGTGCAGCAGGGCAACGTGCGCGACACATACCGCTACCTGACGGAC
CTGTTCACCACCCTGGTGGACCTGCAGTGGCGCCTCAGCCTGTTGTTCTTCGTCCTGGCCTACGCGCTCACCTGGCTCTTCTTCCGCGCCATCTGGT
GGCTGATCGCCTACGGCCGCGGCGACCTGGAGCACCTGGAGGACACCGCGTGGACGCCGTGCGTCAACAACCTCAACGGCTTCGTCGCCGCCTTCCT
CTTCTCCATCGAGACCGAGACCACCATCGGCTACGGGCACCGCGTCATCACCGACCAGTGCCCCGAGGGCATCGTGCTGCTGCTGCTGCAGGCCATC
CTCGGCTCCATGGTGAACGCCTTCATGGTGGGCTGCATGTTCGTCAAGATCTCGCAGCCCAACAAGCGCGCAGCCACGCTCGTCTTCTCCTCGCACG
CCGTCGTGTCGCTGCGCGACGGGCGCCTCTGCCTCATGTTCCGCGTGGGCGACTTGCGCTCCTCACACATAGTGGAGGCCTCCATCCGCGCCAAGCT
CATCCGCTCGCGCCAGACGCTGGAGGGCGAGTTCATCCCGCTGCACCAGACCGACCTCAGCGTGGGCTTCGACACGGGAGACGACCGCCTCTTCCTC
GTCTCGCCGCTGGTTATCAGCCACGAGATCGACGCCGCCAGCCCCTTCTGGGAGGCGTCGCGCCGTGCCCTCGAGAGGGACGACTTCGAGATCGTCG
TTATCCTCGAGGGCATGGTGGAAGCCACGGGTGCGACCACGCCTGGGGAGGGGAGCGGGGTTGGCAGAGGGTCGGCGGGACCGAGGAAGGCACGGGC
GAGACTAGGGGCCAGGGGAGCTGGGGAGGATGGATGGAGGGGCTCGTGGAGGATGAGACAGTGAGGTGAGACAGGGGTCGGAGGCGGGAGTCGAACC
GAGCAACGCCGCAGAAGGCCAAGAGAAAGCTTGGAGGAATTCTCCGAAATGGCACTGGCGTGGGGCCCTGGGCCCAGAGGAATGTGTCACTTGGAAT
AGGGACAGTAATAATAGCTAGTGCTCGCCCAGTATTCACCCTGTGTCATGCGCAGTTCCAAAGCACTTTCTACCTCTGAGTCGATTTAATCCTAACA
AGAACCCTCTGAAGGTAACTTCTTGTTATTGTGCTCACTTTTTAGAGATGAGATTGCTCCAATGAGAAATTAAGGAAGTTGTCCACTTTCCTAAGCC
AATAAGTGGCCATGCCTGGATTGGACACAGGCAATGTGGCTTCAATGTTTAGTGGTCCCGAGTTGGAAGGAGGGGTTAGGTTCAGGGGTTTTCTCAC
TGCAGTCAGGTTCAGGCCCCTGGAATTTGACGGTGAAGGTTTTCCATTGCCTGAGTTATTTCTAGGCCGGATCTTGAGGGGAGTTTAATACCTAGTC
TCACTTGTACCTCCGTTTCCCAATTCATCCATTTCCACTGACAACGGATATAGATGATGTTACCTTTTCTAGCTCTTTTCCAAAAGGAACTGGCAAC
TCATCTGTGATGTCAATAAGTCCAACCCAGACCTACACAGTGAAGGCTTTGGGAGCAGGTGAAAAAAGACCAGTGTTACAGGAGTCGCAAAGGAGGT
CACTTAGGACTTGAGATCTAGAGGATAGATGAGGATGAGGAAACTGCGGGTGGAGGACCAAAGGCCCACTAGGGGGCGCCGCAGTCCCTCCTCTGAC
GCCAGAGCTGCTGATGCTCCCTGCCGGCTTCGCTGACAAGCTGGTGCCTTCAGATCCTTTCCCTGGCCCCTTTAGGCTGAGACTCCGCTTCACACCC
CAACCCCAGCTCCGCATCACTGTTCCCATTCCTGCTTCACCCCGACTCTTTCCTCTTCCCCCACTCACCCCGTTCCCTTTCCTCTCTCTCCAGCTGT
CACTCCTTTTCTGCCAGTATCTCAGGCAGGCCCCTCACCCTCCAGGGAAGTTGCTGCCCGGCCCTCTTTTCTCTTTGTACCCCCAGCCCTGCCCTCT
CCTCCTCGAAGCCCTTCTCTCCCCAGTGTCCCTTATGCCTCTTTCTCTTCTCTCCCACTGGATACTTTCTATTCCAACTTCACCGAGGAATACCAAT
GTCTCAGCGCCAGGCTTTCCGAGTTGACAGCCACTCTCCGGTTAGCTAATGTTCACTCTTCTGTTTCCCCTTGTTCCGAGATGGATATGGGTTGGGG
GCAAGACCCTGTGGCAGAAAGGAGAATGACCTGCCCTGAGGGGTGCACCAGCCCAACAGGAAGATAGGACACAAGCCCCGGGCAGGGAGGACCAGGA
CAGAGGAGATGAGGATAGGAATCTGTCTGTTTTTCTAGAGAGATAAAGCTGGAAAGGATGGTAATATTTTGGGTGAGACAGTCAGGATTCAAAACGC
TTTTGAAAAGCAAGAATAATGAGCCAAAACCCAGCAAGATGACATTTAAAATGAATAAATATAAAATTCTACATTTAGGCTTTAAAAAAATCACTTA
TGTAAGCACAGCATCGAAGAGCACTGGTGAAAAAAGAACTCGGAGTTTTAGTTGGCTACAGTCTTGATGTCGTAGCAATGTGATGCAGCCTCCAAAA
TGATTATGTAATGTTATCCTGGGCCCTATTAGTGAAAGCATCATGGCCAGAAGAGACAGATGGTGCGCGCTCTCTTATGCACGGAGCAGGCCACAGT
TGGAAAATTTACTATACTCAAAATGCTTAAAGGGCCCTCCTTGGCCATTCTGGCTTGTAATCAAAAAAGTAGAGTTCTGGAAAACCAGGTCAAATGA
GGAATCGTGGAGGAAGCCAGGGATGTTAAGTCAAGAGAGAAAACATGAGGGAATCTGAGACTCCTGTTTTCAGATACTCAGAGGACTGTGAAGTGGG
AGGGGAATGAAGCCAAGAGTTCGAAATCCCACGGTACAGGTTTTAGCTCTGTATAAAGAACAACCCAACTATTAGAGCTATCATACAAAGGAGTGGG
CCCTTTATGAAGTGGTGAGCTATCAATCCTGGGAGGTAATCAAGTATAAGCTAGATGCCCATTGTTAGAAATGCTCCTTTGGGGAGCCCTGTATGGA
GTGAGAAGTTGGACTAGAGGATCCCTAAGGTTAGTTTCAAGGTTAAGCTTTTTTTGGTTGGCATCACCAAATGACAGGAGGGGAAAAAAGAGCTGGA

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

```
CATTAAGAGGAGTTGGGGCAAATGGAGAAGACACGAGGGAGCTGGGTAAGAACAGGAGCTAGGGAGGGGGGAAATGGACTGGACCAAAGGGAGGTG
GGAGCCCTTAGGAAGGAATAGAAGGGAGGGTGCTGGGAGTAGGGTTGTGGAATGAGAAGAGGAGAGGGAAGCCTGGAGCTGAGATTCCCCCTGACCG
GTGCCCCTCCTCCCAGGAATGACATGCCAAGCTCGGAGCTCCTACCTGGTAGACGAGGTGCTGTGCGGCCACCGCTTCACGTCAGTGCTGACTCTGG
AGGACGGCTTCTACGAAGTGGACTATGCCAGCTTTCACGAGACTTTTGAGGTGCCCACACCTTCGTCCAGTGCTCGAGAGCTGGCAGAGGCTGCCGC
CCGCCTTGATGCCCATCTCTACTGGTCCATCCCCAGCCGGCTGGATGAGAAGGTGGACGAGGAGGGGGCGGGGGAGGGGGCGGGTGGGGAAGCTGGG
GCTGACAAGGAGCAGAATGGCTGCCTGCCACCCCCAGAGAGTGAGTCCAAGGTGTGACCAGCTTCCTCCAGACCCCTGTGGCAGACCGGGGGCCAGA
CACAGATACATGGGGAACTGCATATCGGAGGTGGTGGAGGAGGAGGAGGAGGAGGAAGGCAAAGCCCCTGGAAATGTGCTAAAGTTGGAAAGTCCCC
GTCCCCCAGAACCTCAAGTCTAGAAACCAGTATGGAAGGGAGGGGTCCTGATTTCAGGGAAATGGAGGGTGGGGCCGGGTGAAAATGCCAGTCTGTG
TTTGACCTTCACATTTGTTCATGAGTGGATGGATGGACAGAATCATCGACTTTTGGGGGTTGGATGGGAAGATGGTACCAGATAAAGACAGCTGACA
GATACATAGATGGACCAGTAGACAACTGGTCCACTCAGGGCTGCCACTAACCTGTAGAACACCCCTGTGCAAATTTTAAAAAGGAACCCTTTTCCTC
CAGACAGATACAGCCCCAAACCAGGGTGCATGGCTTGGGGAGCAGAGTATAGGATGGATTGCAGTCCCCAGTCACCTCTTCTGCCAGCCTCCCCACA
TATGGCACAACTGTCTAATGACACGGTAGGCCAAGCTGAAGTGAAGGAGAAAGGAGCCGGACCAAGATGGGCACATGAGGAGGGTGCCCTCCTAGCT
CCACCCTCACCAGGATGAAGGCGTGCAAGGGGCTCAGCAAGGTGTGAATGACCTTAGTCCGCAAGTTCAGGGAAGCAGGCAGAGCGGGGAGGTGCCT
GAGCTGGGGCCTGGAGAGGGGCCTGGGAAAGGAAAACCAGGGATAGCTATTTTCTTACAGTGGAGTGAGATCTTACAGGTATCAGGCACAGGCAGGA
AGAGAGAGAGAGAGGTTCTGGGGAGGAAGGGCCAGGAGAGAGATCTAGAAAGTGGGTTCACTAGAGCTGGGAAACAGGGAGCCCCTAGGAAAGCAGT
GTGTCCTTGGGGCACAGTCATTCACATCACTGATTGGGTGCCATGTGGAGTGGACATTCAAAAACCTGGTTCCTGTCCTCAAAATAAGGGGCACCTG
GGAAAACAGAGGAATCTACCTGTGGTGACTGAACGAGGGATAATTCAAACTGACAACCTGTGCAGTCCCGTGGAGGGTAGGGGAGTGTGGGTGATCA
GAAGGCTGGGGCCAGTGTAAGGCATAGGGAATATGTAAGTCAGGAGTTAGAAATCTCCAGTGTGCGTTGGAATCACCTGGAGGGCTTGGTAAAACAC
AGATTTTTGGGCTCCACTCCAAGGGTTTCTGACCCAAGAGGTGGGGACCAAAACCATGCATTCCTAAGAAGTCCCCAGGTCATGCTGCTGTTGCTGG
ACTGAGGACCACACTTTGAGAACCTGTGCTCTAAGTGAATACTTGGAAGTCGTTTCAGGACATGGGGCATAGAAACTGAGGAGTAGCTGAGAGGAAG
ATGAAGAGAAGCTGAGAAGAAGCTGAGGATCCTCACAGGAGCAGACAGAGAAATGTGAAGGGTGGGGTTTATGTGTGGGAAAGGGACCCGAAGCCC
AGGCTGAAGAGTTTAACTTTGGGCCCAGAAACTCAACCATCAATGGAAACAGGGCAGTGACAAGTGGAGGGGGTGTCTGGAAGCTGAGCAGGCCCGA
CAGAGAGATGAAGCCATCAGAAGGACTTGAGGGGGCTCCTGGGGAGGTCGGGGGGAGGTGGAGCAGGAAGAGTTTTAGGGGCAAAGGACAGAACCCC
TTGTAGGACTGGAGGCAAGATTGAATGTGGGAGAAAATCGGAGAGAAGCGATAGGAGTTAGAACATCTGGATGTGTCTGCAGCCTGCTGTCAGCCCA
ATTGGGCCAGGGGGTCCCAAAGACGCATATTCTCACCCCACCTCCACCTGCTTCCTGATCACATCCCAGTCACCAGCGGCAGCTTCCTGGATAGTGA
GGGAGAACAACTGCAAGTTGAGAGAGGCAGAGGGGTGGAAGGGACCTGAAGCTGGCCTGGAGAAAAGCATAGGCCCAGGAGAGCCTGCCCTGGGACA
GCGCCTGTCTCCCACACAGCAGCACTGGCCCAGCAAGGACCTCCTCCCTTGGCCCTGGCCACATCCCACTCCTGCCCTTTCATAAGCCCCCTGGGGA
AAGCACTCCAGTCTTCTCTGTTCCACGCTCGGCAGATACGGTCCTATGGGGCACAGCCAGGGTCCTATGGGCATAGCCAGGGCCCTATCGGTCCTCT
GGAAGCAAGAAAGGGGGCCATGGAAGCAGCCCAGACAGCTGGGGTTCACTCAGAGAGGACCCAAGTCCCAGTCCCTTCCTTTCAGTCAAAACACGGA
TATCTTTGCCTCAGGTCACAGGGCCACTCGGGCCCTGTCATCAAAGATGAGATTCCTGAAGCCTGGCATTGACTGGTCCCCTAACAACAGATGTTGG
GATGGAGAATGGGGATTCATTTGGGTTTCAGTAAAACAGGGGGGTCTGGACAAGAGCGGGTGGGCTACTTGGTATCCACACACACGCACTCACACAG
GAGCCAACCCATTGCAGCTGAACAAGCAGAGAAACTCAGTCTGGAAAGGCCCCTCCTGCCTGCTGAAGTCACTGAGACCCTGCCACACCTCTCCTCG
CCACTGTCACCACTCAGGGCACCACTGTACAGTGCAACAAGTCAGGAGACCTAGGTCCTACTCCTGACACTTGCTAATTAGCTCTATGACTCTGGGC
AAATCGCATATCTGGGCCTCAGTTTCCTCATCTGTAAAAATGACAGCAAACTCGTAATGCTCAATAAATGTTTAAATAACAACTGAAGGAGGCCTGC
CAGATGCCTCTTAAGGTGCCGTGCAGGTAAGAATTTTAGGATCAGAGAATCCTTAGGCAAGAAAATTCATGAAACTCCTGGGGCACTGGAGGAGGGG
TGAAGCTGAAGGGTGGGAGGGAGGAGACCCCAGGGTAGGTACAGGCAGGTGAAGCGGGTATATGCAGGTGTAGTGGGTATATGCGGGTAGAGGGTAT
ATGCAGGTACAGCGAGTACATGTGGGTGCAATGGCTCTGTGGACACACAGGCCCTCCCCTGACTGCCTGTTGTCCCAGCCTGAGTATCAGTTGTGTT
CTGAGGCTTCTATTCTGCTGCTATGGGTCAGAAGGAACAACAATTTCAGCCCCAGGGCCTAGTCGGAGGAGTCAGGTCCAAGACTAGCCTGACCAGG
AGAATGAGACGTGGGAAGAGTTGGGGAAAGTCTGGGAAGCTCAGAAAAGGCACTGCCCCTGGAGGCCCATGCCCTTTAACATGGGAGAAGCTGGTGC
GGGGGTGACCACAGGCAGCTGGAACCTACCCTCCTTTTCTATGCTTCCCTCCCCAAGTAGGAGTCCAATCAGGAGTTGTCTCAGCCCCGACAGTTCA
GGCTGCAGATGGAACCCAGGTGTCCCCTCCTGGGGTGGGTGGCATGGCCCATGGAGGCCAGATGGTGTTTGTGGTGGGAAGAGAGGCCTGGGTCATC
CAGAATAGGTTGTCAATCCCCAACCACCTCCCTACTATGCACCCTGAGCGTTTTACAGTCTCATGGTAGGGAAGACACAGCCAAGCCTGCTTTTTAT
AAAACAAGTTTATTCACATTTTAGAAAAACTAATTCCAGGACAGGAAATGGCCTCCCTATAGGATCCCTAAGAGATCAAGAACAGAAGGCCAGAGGG
AGGGGCTTGGGAGGGAAGGAGTGGGGAAGGGGAGGCACGTCTCCCATTCTGGGTAGTGGGAGGTCAAATAAATTAAAGGAAGAGTGGACAGAGGGAG
```

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

AGGGTGTCCAGGCAACCAGAGGAGGGCTTGGAGCTGGGCCGGAAGACAGTCGACACCTGCAAGACCTGAAAAGGGTGCCCGGTGTGGGCTAAGGACA
GAGAGCCCTGAGTGGGGCTCCCTCGCGGCCTCCACCCCTTAACAGGGCCCTGTGGATCTGAGCTGCCTACTCCTCCTCCAGGTGGGGCCTGGGAGGG
AGCAGCTTGGTTCAGGACTTGGGGGTGGGAAGCCCAATGAAAACAAGGTTGGGGGGTTCTTTTCCCTCACCTGGGGAGTAACGGATCACCGTTTTCG
AAGCCTCTTCATGAAGCAGCAAGTGATGGTACCAAGGACAGTGGCACCAGTGACTAGGGCCACCCCTGTACCCACCAGCAGAGGCACAAATAGGGTG
TCCACGGCTGGGGGAGAGAGGATGACTGTTCAGAGAGGATGCCATCATCCTCCACCCATACACTTGCCTCTGCGCTTTCCCCATCAAGTTCTCTGAA
CCCACCTTCTCCATTCACAGACACCCCCATCCCTGCCCACAGCCTGCCCCCTCAGCATGCAAGTCAGCATCAACCACAGAGGACCCCGTGCAGGTGG
GCACTGCAGGGCTGGAAGTTGGATTTTTTGAGACTTCATGTGACATAATGTCGAGGAGAGAGATAGTAGCAGGAGGGTCAGAAGATGGAAGGGAAG
GCCAGTGGCAGAGGCCAGGAGGAAGGCAGAGTGAGGAGGGTGGAGGGGGTGTCACTCACCATGCATGTAGGGGTAGACTGTAACAGGCCCTGAGCGG
GCACTGCCCGCCTGGTACCAGCTGTAGTCGGCATGCTGCACCCAGGCGCTGGGGGCACAGTGGTACACGCCTTCATCCTCGGGCCCCAAGCTGTGTA
GTCTCAGCCGATGGCTTCGGGGCCCCACCAGCTCTACGCTGACAGGGCCTCCTCCAGGCCGGACTCCCAGCTCTGCCACACCATCCTGGCCTACGCC
ACCCACCAGCTGGGCAGGGACAGAGCTGAGCTCTCCGTCCTCTGGTCGCTCCACCCACCAGCTGGCGGCCAGCCGCAGTCCTGGGGGGCCACCCCGC
ACAGAGATGTTGCACAGCAGGGAGGCAGTCTCCCCGCGGTACACTGTGCCTCCTGCTAGCCATGCCACAGCCTCCAGCACCACACCTGCAGAACAAA
GGACATGGGGTCAGAGGGTGCAGGGCCAGGGAGCATGGGGTTAGGGCTGCCGCCAAGCACCGCCCCAGGAAACTCAGGGTATTCCCACAATCTTGGT
AGAAGAGGAGCGTGAGGCTGTGGCCTGCAAACAGCTGACCGAGAGGGAGGGGTCATGGAAACAGAAGGAAAAGGGGTTGACAATCCTCGAACCCCGT
CCAGGGCCCAGCCCCCTCTCACCTTCCTCCCGCACATGTACAGGGAGAGGCCGGGAACGGGCACTGGCTGCTTCACGAAGCCGGGTCCCAGACCCTC
GAACATAGGCTTTGGCGAGGCAGCGGTAGGTGCCCGCATCACCAGGCCTGGCAGCCTCTAGCCGTAGCCGGTATGTTCTGGATGCCACCTTCTCCAT
GGCAATGTGTCGGCCCTCATAGCCAGGGCCCAGGCTGCCCACACCCTCTGTGTCCAGCTGGGCTACCAGGCGGCCGGGCCCCAGGTGCCCCCGCAGG
TGCCATCTCCCAACCTACAGAGTATGCAGCATGACGGCCTGCTGGGGGAAGTGCCCCTGACACATTGCACAGCAGTTCCAAGGGCTCCCCTGGGCCG
ATCCGACGTTCACCAGGCCCCACTGTCACTGCCAGCTGGCTGGCTGAAACACAGGTAGGGGAAGACGTGTCATAGACGCAGGAGGGGACACACAGGC
ACCCGATTCCCCAACTTCCTGTTTCCTACTTGACAGCAGCAACTTCAAAACCTCCTGTCTCCCCCTCACTAGGTATGACCATCTTTCTATTTAGGGG
CTTGAATCTCACCCCTCAGCATGGGCCTCCTATCTCTATACCCAATTTCTGAGCAGAGAAAACCCATCAAGGGCCGGGGGAGAGAAATGCTAGCAAG
GCTGCTCACTCTGTGGAAGATGAGTTCCTTGGAGTCAGATGATGGCTATCTGGTACCCCCTGTGGCCACAGTGCCCACCAGGATACTGTCCCTCCCA
GCTCCCACAGTGGGATGTATAAGTGGCACTTACACAGCGTCTGCACATCCACGTGGGCCAGGACGGCCCTTTTCTCTGCAATCTGGGCCCAGCTGCC
ATCAGGATCCTGAATCCACTCAGCGGCAGTGCAGTGGTAGGTGCCTGCGTCCCCTGCCTGTGCACCCCCTACTACCATGCGGTACCGATCGGTCCCT
TCCTTGCCCAGACGAAGCTCCCCTGCAGCCAATCGCTCAGCATAGGGAGCTCCAGCCTCCACGGCCAAGTCTGACCGGATTCCCACCACTTCCTGCA
GAGTTGACCGCCCAACTGGTGCCTCGGGCACAGATCGCCCAAAGGACACTGCCAGGTGTGTGTGCTTCTGTGTGCTTGTCCTCGCCAGGCAGCCCAG
TGCCAGCTCCTGCCCCTCATGCACCGTCATGCGTGGGGGTGAGGTTGGGGCCTGGCGGCCTCGGGGCCCTGGGGGGGCAGCAGACACCTGGAGGACA
TCTGGAAGAACTGGAGAGAACAGCTGGAGTGAGGGAGGGCTGGGAGCTGGCAGCCCTTGTTACTGTTTCCTGTGTATAGCCTATCTCCCTAAATAAA
CTGTGAGCTCCCAGAGGGCAAAGATCGCATGTTGTATTATTTCTTCTGTAACTCAGTGGTGCCAAGGGCAGTACTGGGCACAGCACAGGCGCTCAAT
AAATACTTGTAGAATTTCATAGAACCAGCCCATCGCCTACTCACCCTTATGTTTGAGACTGACCTCTGTTTGAAATACTGAGAAAAGCGGCTCTTTC
TTCTCAGAAGACAAAGAAACTTAAGAGAGTGAGAATGTCACATGGTCTAACTCCTTCCCTAACTCTACTCTCTTTCCCAGATCTGGGTCCTGTACTG
TCCAGGAGTAGAGGCTATTCAACCCAACAGTCTTCTTCGTTCTTGGGAATGGAAAGTGGACTGGACAACTTAAGGACATTTCTTCTCCCAGGAGGGG
TCTTAATATGATAAGATGAGCACTGGCCTGGGTGAGGAACTCTGGGTTTGAGTCCCACATCAGCCACTGAGTTATTGGGTGACTTTGTGCAAATCAC
TTAACCTCTTTGGGCCTCAAGTTCCTTGGCTACAAAACCTAAGGGGCAACTAGATAGGTCACTTGTGGCCTTGACTTTCTGCCTTGAGAGGGTGTGT
GGCTCCACCCCGTCCCAGGGCCCAGTACCTCTCAGCTCCACCTTGCCGCTGTAGCTGCCCAGGTAGCGGGTATCAGTGGAGGGGGTGTGGCACTCAT
AAATGCCGGCATCCTGGGCCTGCAGGCGGGCAATCTTGAGCACCACGGCATCACCTTGTAGGCGCTGCACCTGCACCTCACCCGCCACCACTCGGGA
CTTGAAGACAGCATAGGAGAACTGGGTATCCTTGGTACTGACAATGCCCAGTGCAGTATCTGGGGCCTCGGGCCTATACAGGAACCACTCGAAGTTC
TGCTGGGCAGGGCCCTCATAGCCGCTCACATTGCACGACATGGAGACAGCTGTGCCAGCCACGCGGTACAAGGGCCCCTCGGGGACCAGCACCTCCC
GGGCCCAGCATCCCATTCCTGTAGGGAAAGGCAGAAGGAGTTGGAGATGCCTGGTTCCTCATTCCATGCCCTCTGCCGCCACAAGCACCATTCTTGA
TCTCTGCCTACAAAAGGAAAGGAGACCTGGGAAAGCTTGTCCACAGCTTGGACCCTGTTCTGAGAATAGGAAAGGGATGCTGTGATATAAGACACCT
GGATCTCAAGGAGGTGGCATCGGCCCAGGATTGCCTTGGCATCCAGATGCATCCCATTTCTGGCGGACTAGAAGCACACCACCTGAAGGCAGAAAGG
AGTACATCTGATTCCTGACCTAACCAGGCCTTGGTTCCAACTGAACCTTGATCTGTCCCTGCCACTCACCCACCTCCATGTCTGCCATTCCTTCCTC
AGCACCTGGCAAGGGGAGCCTTCTGGCTAGGGGACTCTGAGACTACATGTCCCTCTCCTTTGCTTGAGGGGAGCTGGCAGTCTTGCTCAGAAGTGCT
AGTTGGCTCAGCTGTGTCACCTGGGCGAGACAATGGAGCCAGTGACCCTAGCTGGAAAGGGCACAGGCCCAGTCAGTTCTCACCAGGCTCTGCCCTC

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

```
CCCTCTCCAGCTGCGCCATGAGCTCACTGCTTCTCTCACCCCACAGGGCTGCCCAGGCAGCTGGGGCTTCTGGGGCAAGATCCAGGCTCTGCCCTGG
CCATTGGGGGCAGAAGATCCCCTCCTCCAGTGCCTGCCAACCTTCCGGGCTAGCCCAGCAGATACAGAAGGTGCCTGCCCCAGTTCCTTAACAAAAG
CCTTCATTTGCACATGGTATGCATTCATTTACATATATGGCTCTCTTTCTGTAGGGAGGCACTAAATCCCCAGCTGCCCCTTCTCATCTCTCTCCCT
TCAGAAAGGCCAAACCTCTCTTCTTCACCCTACTCCACCCCTATGCCCAACCCTACCCCAGCAGATACTCCTGGCAGACTTAGAGGGCTTAGCTCCT
CCCTTCTTTCCTTCCATAGCTCCCACTAGATAAGATCACAGAACCTCAATGTAAAGAGGGCTAGGCCACCCCTCCCCACCTCTCCCAATTTTACAGA
TGAGAAAGGTAAGGCAGGAAAAGTATAATATGTTAGCCAAGATCATGCTGTCCCTAGATGGCTTCCACACACTCCTCCAGAGGGGCAAAACCAGAGA
GGAAGATGGGGAACTCCAAGGCCAGGCCTGAAGGGACTGACCTCACCAACCAAGAGTGTCACTTTTAGGCCTCCCAGGGGGATACCATGGACTTTCT
GCAGGAGCTAGAGGAAAATGCCCAGGAGTCTGTGGTCAAACTCTACCCTCCAGCTTCTCTAGAACGGCTCCTCTGAACTTCCCCACCCCTGCTTCTG
GGCTCCTAGCCCCTTCCTTCATCCTCTGGCTGGGTCACAGGGAGAACTCATGGTCTGTTGTTAAGGGCACAGCTGCCAGTCAGGAAGTGGGATTCCA
GCACCATCCCCATGCCCAGCTGTGTGGCCTGGGATCCAGTCTCTTTCTGTCCTAGGCCTCAGTTTCCACACTGGAGGAGAACTAAGAGCTCCAGCTC
TGACCATGTGTGAGTGCGTATGTGACTCAGGAGAGCCCTGCCCCAGGCCAGGCAAGTTTCATAATCAGAGTGACGGTGGAGACAGCCAAGCTGACAC
CTTCCCTGACTGCCTCAGGGCAGACTGCTCAGAAGGCCCCCTCCCATTTTCCTGGCTCCACAACTGCTGATGCTTGGAGATGCCCATGGGAAAGTCA
CCTCCACAGCCTTAGGAAATCAGTTGCCACACAGCTCTCTCTCCCCTCCTCTGTATCAGTCGCAGCAAGGAAAGGGACAGCAAAGAGGCCTGCTTTG
GAATCAGATCTGTGTTCAAATCCTAGCCCCAACACTCACTAAATGTGCTCTCTGGGGCAAGTTACTTCATTTTCCTCATTTGTGAAATGAATGTAAG
TGCCCACAGGCAGTGGGTGCTCAGACCTCTGCGTGCTCCTTTTTCAAACACAGGCCAGCACTTCCCCACCTCCCTGGGCTCCTCCCTGCTCCATGCT
GCCCACTGGGGAAAACACACCAAGTGCTAGGCAACCCAGGCCCCACAGCGCCTTCCTCTCTGTACATCCTCCTGCCACCTGCCCAGGGACCAGGGAG
AGGACTCATCCTAACCCTGCAGGGCCCAGGGACCTGCAGCAGGGGAAGGCTTTGCTTGGTGCCACTGTGGAGCTCTGGTCTAGAAACAGGCAGCTGG
GGCTACCTTCAGCCTCTGCCTTGACGACAGCAGCTCTGAAGTCACCATCCCCACCCCCACGCTTCACTCTCATTTCAAGGGCTTCAGCCTCATCAAC
ATCTGTACTGGCAGTTTCACTGTCTCCATGCCATACTCTTCCCCAGACCACCTCCTACAGGGAGCCCTCCAGTTCAGGCCAAAAACAATTCCACTGT
CATTATCCCCATGCATCCATCCAAGATTGGCCCAGAACACCCCACCATGAACACCCACCACAGCAGGCACAAGGTGCTTGGAGATCCCAGGATCAGT
CTCCATGGAACCTGGTTTCTCCTGAGGCAAGGAAGCTGGAACTAAGCGGTGTGAAAACTGATGGGTGGCTGCAGAGCCAAGTGCCATTTGGGAGACA
GGAAGAAGGGCAAAGAGGGACCCAACCCAGGGTGGAGATGGGGGTGAGAGAGGGAACTGCCCCCAGTTGATGAAGTGCGTGGAGCGCAACTGGGAGA
GACTTACTTCAAAGATCGTGGGCAGAACTGGCCTCTGGGCCTCCAGCCAACTCTGGGGCAATTATGAAGCTGGGCAGGCACTGCCCTCGTAGGGCGG
GCACCCAAGGCCACGCCTGGAGCTCAGTGTGGGGCAGAAACGAGTCGCAGCATTTGGTGCAGCGACCCCAGTACGTGGGTATCCTAGCTGAGATGTG
TGGCCTGCCCCGGGAGGCCGAGCAGTGCCTGGGGCAGCACCTTAGTGGGTCCTCTCTACGCCCCAGTCCCTGGCTTAGAGCTGGGGAGCCTGCACTC
TTCCCAAGACTGGCTCGGCGGACAGCCACAAAGCGCAGCTGGACGCCGACCCCGGGGAGGCTGGAGGTACCCCTGACGGAGGAGGATGTGAGGAGCC
CCGAAATGCTAGGGGGGTGCTGGATGGCAGGCACCTGCCCGGCAGGGCCGGGAACCGGAACGGGGGCCTGGCTTACCTAGCATTAGCAGCAGCAGCA
GCGGCAGCGAAGGCGGCAGCAGCGTGGGCCTGAGGGCGCCCATCCTGCGCGGCCAGCTCTGGGGAGGCTCCGGGGGATGGCGCGGGTTCTGGGGGGC
CGGAAGGGTGGGGGGCGCATGCCCAGGTTGAGGGCAGGAAGCGGGGCAGCGAGGCGTGGGTGCGCCGAGCGAGCTGAACTGGAGCTGCCGAATCCCC
TCCCTCCGCCCCTCCCGCTGCTTTCCCTCCAGCCCTCGGCAGTTCTGAAACCATTCTCGCCCCGGCCCGCCCCGGCACCGCCCCTTCCACCGCCCCG
TCTAGGCCCGCCAGGACTACAGTCGGACTCCAATCCTGGCTCCTCCCCGGGCCCCGGCCCCGCCCCAGTCCCAAGCCGCACCCCTTCCCCGTCCCCG
CAGGGCTAACGTCAGCCTCCAATCCTGGCTCCGCCCTGGACCCCGGCCTCGCCCCGCCCCTGGCCCTGGCTCCGCCCGAGGCCCCCGCAGGAGTGAG
CTAACTGCACCTCTGCGCATCGAAATTCCCACCCACCCTCGCACAGAGCGCATTCCACCCCGCACCTGCCAGCCTTTCCTGGAGAGTTGGGTGCAGG
GTCCCTGGGATTGGCGAGGTGACTGTGACCACGCATTTAGAATTCAGTTATTTGCTCTGAGCCATAGTCCTCGCTGCAAACCCTGCTGAAGTAGGGG
TTGGCGGAAGCCAGGAGTTCCTGAATGCGAAGGGTTTGAGCTGAAGGGCGCTTCCAGGATCCAGAAGGTCACTGGAGACCTGTTTTTCACCCCCTCA
GAGGGCAAAACCAAAAGAAAAATGGATTAGGAGAGGGGG
```

HUMAN SEQUENCE - mRNA (SEQ ID NO: 5)

```
ACATTTAGGAGAAACAGCGGTGTCTGCGGCTCCCACCCTTCGGGGGGCCCGTGGGGGGGGCGGTGTCAGGGGCATGGACGCCACCCCCCAGGGGTCT
CTGCTGCCGGCTACTCTCCTCTCCACGTGCTCCCCTCCAGGACCCCCGACGCCGCCTAGGCGCCCACCGACGCGCGGCAGGTGGCAGCAGCTCGGGC
CCCCGCCGCACTCCAGGCGCCCGCAGCGCTCGCCCTGACGCGGCCGCCATGGCGCAGGAGAACGCGGCCTTCTCGCCCGGGCAGGAGGAGCCGCCGC
GGCGCCGCGGCCGCCAGCGCTACGTGGAGAAGGATGGCCGGTGCAACGTGCAGCAGGGCAACGTGCGCGAGACATACCGCTACCTGACGGACCTGTT
CACCACGCTGGTGGACCTGCAGTGGCGCCTCAGCCTGTTGTTCTTCGTCCTGGCCTACGCGCTCACCTGGCTCTTCTTCGGCGCCATCTGGTGGCTG
```

TABLE 1-continued (mouse gene: mCG2257; human gene KCNJ9)
Mouse genomic sequence (SEQ ID NO: 1)
Mouse mRNA sequence (SEQ ID NO: 2)
Mouse coding sequence (SEQ ID NO: 3)
Human genomic sequence (SEQ ID NO: 4)
Human mRNA sequence (SEQ ID NO: 5)
Human coding sequence (SEQ ID NO: 6)

ATCGCCTACGGCCGCGGCGACCTGGAGCACCTGGAGGACACCGCGTGGACGCCGTGCGTCAACAACCTCAACGGCTTCGTGGCCGCCTTCCTCTTCT
CCATCGAGACCGAGACCACCATCGGCTACGGGCACCGCGTCATCACCGACCAGTGCCCCGAGGGCATCGTGCTGCTGCTGCAGGCCATCCTGGG
GTGTCGCTGCGCGACGGGCGCCTCTGCCTCATGTTCCGCGTGGGCGACTTGCGCTCCTCACACATAGTGGAGGCCTCCATCCGCGCCAAGCTCATCC
GCTCGCGCCAGACGCTGGAGGGCGAGTTCATCCCGCTGCACCAGACCGACCTCAGCGTGGGCTTCGACACGGGAGACGACCGCCTCTTCCTCGTCTC
GCCGCTGGTTATCAGCCACGAGATCGACGCCGCCAGCCCCTTCTGGGAGGCGTCGCGCCGTGCCCTCGAGAGGGACGACTTCGAGATCGTCGTTATC
CTCGAGGGCATGGTGGAAGCCACGGGAATGACATGCCAAGCTCGGAGCTCCTACCTGGTAGACGAGGTGCTGTGGGGCCACCGCTTCACGTCAGTGC
TGACTCTGGAGGACGGCTTCTACGAAGTGGACTATGCCAGCTTTCACGAGACTTTTGAGGTGCCCACACCTTCGTGCAGTGCTCGAGAGCTGGCAGA
GGCTGCCGCCCGCCTTGATGCCCATCTCTACTGGTCCATCCCCAGCCGGCTGGATGAGAAGGTGGAGGAGGAGGGGGCGGGGGAGGGGGCGGGTGGG
GAAGCTGGGGCTGACAAGGAGCAGAATGGCTGCCTGCCACCCCCAGAGAGTGAGTCCAAGGTGTGACCAGCTTCCTCCAGACCCCTGTGGCAGACCG
GGGGCCAGACACAGATACATGGGGAACTGCATATCGGAGGTGGTGGAGGAGGAGGAGGAGGAGGAAGGCAAAGCCCCTGGAAATGTGCTAAAGTTGG
AAAGTCCCCGTCCCCCAGAACCTCAAGTCTAGAAACCAGTATGGAAGGGAGGGGTCCTGATTTCAGGGAAATGGAGGGTGGGGCCGGGTGAAAATGC
CAGTCTGTGTTTGACCTTCACATTTGTTCATGAGTGGATGGATGGACAGAATGATGGACTTTTGGGGGTTGGATGGGAAGATGGTAGCAGATAAAGA
CAGCTGACAGATACATAGATGGACCAGTAGACAACTGGTCCACTCAGGGCTGCCACTAACCTGTAGAACACCCCTGTGCAAATTTTAAAAAGGAACC
CTTTTCCTCCAGACAGATACAGCCCCAAACCAGGGTGCATGGCTTGGGGAGCAGAGTATAGGATGGATTGCAGTCCCCAGTCACCTCTTCTGCCAGC
CTCCCCACATATGGCACAACTGTCTAATGACACGGTAGGCCAAGCTGAAGTGAAGGAGAAAGGAGCCGGACCAAGATGGGCACATGAGGAGGGTGCC
CTCCTAGCTCCACCCTCACCAGGATGAAGGCGTGCAAGGGGCTCAGCAAGGTGTGAATGACCTTAGTCCGCAAGTTCAGGGAAGCAGGCAGAGCGGG
GAGGTGCCTGAGCTGGGGCCTGGAGAGGGGCCTGGGAAAGGAAAACCAGGGATAGCTATTTTCTTACAGTGGAGTGAGATCTTACAGGTATCAGGCA
CAGGCAGGAAGAGAGAGAGAGAGGTTCTGGGGAGGAAGGGCCAGGAGAGAGATCTAGAAAGTGGGTTCACTAGAGCTGGGAAACAGGGAGCCCCTAG
GAAAGCAGTGTGTCCTTGGGGCACAGTCATTCACATCACTGATTGGGTGCCATGTGGAGTGGACATTCAAAAACCTGGTTCCTGTCCTCAAAATAAG
GGGCACCTGGGAAAACAGAGGAATCTACCTGTGGTGACTGAACGAGGGATAATTCAAACTGACAACCTGTGCAGTCCCGTGGAGGGTAGGGGAGTGT
GGGTGATCAGAAGGCTGGGGCCAGTGTAAGGCATAGGGAATATGTAAGTCAGGAGTTAGAAATCTCCAGTGTGCGTTGGAATCACCTGGAGGGCTTG
GTAAAACACAGATTTTTGGGCTCCACTCCAAGGGTTTCTGACCCAAGAGGTGGGGACCAAAACCATGCATTCCTAAGAAGTCCCCAGGTCATGCTGC
TGTTGCTGGACTGAGGACCACACTTTGAGAACCTGTGCTCTAAGTGAATACTTGGAAGTCGTTTCAGGACATGGGGCATAGAAACTGAGGAGTAGCT
GAGAGGAAGATGAAGAGAAGCTGAGAAGAAGCTGAGGATCCTCACAGGAGCAGACAGAGAAATGTGAAGGGTGGGGTTTTATGTGTGGGAAAGGGAC
CCGAAGCCCAGGCTGAAGAGTTTAACTTGGGCCCAGAAACTCAACCAATCAATGGAAACAGGGCAGTGACAAGTGGAGGGGGTGTCTGGAAGCTGAG
CAGGCCCGACAGAGAGATGAAG

HUMAN SEQUENCE - CODING (SEQ ID NO: 6)

ATGGCGCAGGAGAACGCGGCCTTCTCGCCCGGGCAGGAGGAGCCGCCGCGGCGCCGCGGCCGCCAGCGCTACGTGGAGAAGGATGGCCGGTGCAACG
TGCAGCAGGGCAACGTGCGCGAGACATACCGCTACCTGACGGACCTGTTCACCACGCTGGTGGACCTGCAGTGGCGCCTCAGCCTGTTGTTCTTCGT
CCTGGCCTACGCGCTCACCTGGCTCTTCTTCGGCGCCATCTGGTGGCTGATCGCCTACGGCCGCGGCGACCTGGAGCACCTGGAGGACACCGCGTGG
ACGCCGTGCGTCAACAACCTCAACGGCTTCGTGGCCGCCTTCCTCTTCTCCATCGAGACCGAGACCACCATCGGCTACGGGCACCGCGTCATCACCG
ACCAGTGCCCCGAGGGCATCGTGCTGCTGCTGCTGCAGGCCATCCTGGGCTCCATGGTGAACGCCTTCATGGTGGGCTGCATGTTCGTCAAGATCTC
GCAGCCCAACAAGCGCGCAGCCACGCTCGTCTTCTCCTCGCACGCCGTGGTGTCGCTGCGCGACGGGCGCCTCTGCCTCATGTTCCGCGTGGGCGAC
TTGCGCTCCTCACACATAGTGGAGGCCTCCATCCGCGCCAAGCTCATCCGCTCGCGCCAGACGCTGGAGGGCGAGTTCATCCCGCTGCACCAGACCG
ACCTCAGCGTGGGCTTCGACACGGGAGACGACCGCCTCTTCCTCGTCTCGCCGCTGGTTATCAGCCACGAGATCGACGCCGCCAGCCCCTTCTGGGA
GGCGTCGCGCCGTGCCCTCGAGAGGGACGACTTCGAGATCGTCGTTATCCTCGAGGGCATGGTGGAAGCCACGGGAATGACATGCCAAGCTCGGAGC
TCCTACCTGGTAGACGAGGTGCTGTGGGGCCACCGCTTCACGTCAGTGCTGACTCTGGAGGACGGCTTCTACGAAGTGGACTATGCCAGCTTTCACG
AGACTTTTGAGGTGCCCACACCTTCGTGCAGTGCTCGAGAGCTGGCAGAGGCTGCCGCCCGCCTTGATGCCCATCTCTACTGGTCCATCCCCAGCCG
GCTGGATGAGAAGGTGGAGGAGGAGGGGGCGGGGGAGGGGGCGGGTGGGGAAGCTGGGGCTGACAAGGAGCAGAATGGCTGCCTGCCACCCCCAGAG
AGTGAGTCCAAGGTGTGA

EXAMPLES

Example 1 mRNA Expression Analysis of KCNJ9 in Breast Cancer Samples mRNA was prepared from breast cancer samples as by standard procedures as are known in the art. Gene expression was measures by quantitative PCR on the ABI 7900HT Sequence Detection System using the 5' nuclease (TaqMan) chemistry. This chemistry differs from standard PCR by the addition of a dual-labeled (reporter and quencher) fluorescent probe which anneals between the two PCR primers. The fluorescence of the reporter dye is quenched by the quencher being in close proximity. During thermal cycling, the 5' nuclease activity of Taq DNA polymerase cleaves the annealed probe and liberates the reporter and quencher dyes. An increase in fluorescence is seen, and the cycle number in which the fluorescence increases above background is related to the starting template concentration in a log-linear fashion.

For data analysis, expression level of the target gene was normalized with the expression level of a house keeping gene. The mean level of expression of the housekeeping gene was subtracted from the mean expression level of the target gene. Standard deviation was then determined. In addition, the expression level of the target gene in cancer tissue is compared with the expression level of the target gene in normal tissue.

As shown in FIG. 1, KCNJ9 was up-regulated in approximately 12% of breast cancer samples examined.

We claim:

1. A method of diagnosing breast cancer comprising:

a) determining the level of a nucleic acid comprising the nucleotide sequence of SEQ ID NO:5 or SEQ ID NO:6 in a sample comprising breast tissue of a first individual; and b) comparing said level of the nucleic acid in (a) to a level of the nucleic acid in a second sample, said second sample comprising non-cancerous breast tissue;

wherein a higher level of the nucleic acid in (a) relative to the level of the nucleic acid in the second sample indicates that the first individual has breast cancer.

2. The method of claim 1, wherein the breast cancer is ductal adenocarcinoma.

3. The method of claim 1, wherein the difference between the level of the nucleic acid in (a) and the level of the nucleic acid in the second sample is at least 100%.

4. The method of claim 1, wherein the difference between the level of the nucleic acid in (a) and the level of the nucleic acid in the second sample is at least 150%.

5. The method of claim 1, further comprising comparing said level of the nucleic acid in (a) to a level of the nucleic acid in a third sample, said third sample comprising a positive control comprising cancerous breast tissue.

* * * * *

SEQUENCE LISTING

```
<160> NUMBER OF SEQ ID NOS: 7

<210> SEQ ID NO 1
<211> LENGTH: 26642
<212> TYPE: DNA
<213> ORGANISM: Mus Musculus
<220> FEATURE:
<221> NAME/KEY: misc_feature
<222> LOCATION: (1)...(26642)
<223> OTHER INFORMATION: n = A,T,C or G

<400> SEQUENCE: 1

nnnnnnnnnn nnnnnnnnnn nnnnnnnnnn nnnnnnnnnn nnnnnnnnnn nnnnnnnnnn      60

nnnnnnnnnn nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnnnn nnnnnnnnnn     360

nnncctcatg aatgctgaga ctaaaggtgt gcatcacccc tgcccaattt caaaatagtg     420

acccaaggga agaccagatt acaaggtgct gcactacaaa gtgagaaaat gttaacggtt     480

acccttttaaa aactttgctt agagggaaaa aaaaaaaccc acaatcataa ccaaagcaat     540

ggaccaggaa ctattttcct gcctgttttg tcttttcaaa tttctgtcat cttctgctcc     600

tagagaggaa cggctacagt aagatggtct gaagacctgg tagttttttt tttttttttt     660

tttttaagat ttatttattt attatatgta agtacatgta agtaagtaca ttgtagctgt     720

cctcagatac tccagaagag ggcatcagat ttcgttacgg atggttgtga gccaccatgt     780

ggttgctggg atttgaactc gggacctttg gaaaagcagt cggtgctctt aaccactgag     840

ccatctcgcc agcccagacc tggtagttta agcctgcaat ctcagctgtt tggggagggg     900

aagcaggagg gttgcaagct caaagcctga gctacagaat gagttcaaag ccagtgtgaa     960

taacttagca gggctcacag tcttgacatt cagagatggg gaagattatg gggctgagct    1020

cagaccacaa tataaaatga agaaggaaca cagaggagag aagccaagaa ctgtcggggt    1080

ttatgaaatc attacaagac acaagaattt attatttttc cagaattgtt acccaagcat    1140

ttggcatcca tcgccaccta catgtcagtg tccacctgga cagaaatctc aaacttagtc    1200

cagcgtagaa catcttaccc acaggagcgc tcctcatggg actatgtcac catcatccaa    1260
```

-continued

```
ctagaaacac agcagtcatc tcagcctcct tagtcttcct tacagcagca actccatcct   1320
ctaaccaaag catctcccac tgagcacgcc ctcctgcccc cctctctctc tctcccttta   1380
tcgctgctgc agtctacagc agatgcacct ctcagcaggg atcctggagc agccatctag   1440
tgccttatcc cctccagtct ttctacactc caataatgct tcaggtcact aactccttta   1500
tgtaaaaaca attaaggctc agcaagatgg ctcagagggg taaaggcaac ttgctgccaa   1560
acttgatgac ctggggtcaa tctccagtac tgatgtggta ggagagactc aactaccaag   1620
agttatcctc tgacctctac atgtgtgttg tggtacaccc acaaacacag agagagagag   1680
agagagagag agagagagag acagacagac agacagacag acagacagac agagacacac   1740
acagagagaa atgtaacgtt tagagaagaa tccatccata ttctttagca cagaacagaa   1800
ggcacattaa ttataacctg ggcatcctgc cctgtcttcc tcacatccaa ctctatagct   1860
gcttcctcct ctaacaccca aggttgttaa gtcttgtgtc cccttctgta tcttgctcct   1920
tgttctttgg tcacacagtg accaaagtca ctgagtgttg tgcaaacctc ttcttcttga   1980
ctcctgtatc tctctggagc tctacttagg ctccagtacc tgcaagggat taatgccctc   2040
acatgacagg ccccagacag aacccatcct ctttccctct caccaaggtt gggaatgctc   2100
acagctccct gatttctgtg taactcctgt caagcagact gaaacaccga cattacatct   2160
tgctctttat gcttgcctat gtcccattct gtgtcatgac aattcagcca ccaagttctg   2220
ttaactctcc cttggttata tttctctagg atacacattt tcatttctat ggccagaatc   2280
ataaaattac cactagccca ggacctgacc catccctcac ccctctttcc agtatcaaag   2340
ggagacaaac tgtttttatt aaagatgtac tgtatttaaa aaaacctaga atcaaaactt   2400
tgaacaaagt ggggtgtgat ggtatacacc tttaatccca gcacttggga ggcagaggca   2460
ggtggatttc tgagttcaag gccagcctgg tctacaaagt gagttccagg acagccaggt   2520
ctacacagag aaatcctgtc tcgaaaaaac caaccaacca aataaataaa taaataaata   2580
aataaataaa taaataaata caaggtctct ggataaactc cttccaaata gaaatgagaa   2640
gccatctggt gaagctcagt gtgagggtga ggtggcacga gatggaactg ggcaattgga   2700
aagagttagg tattgtagag ccacaggaga gcaggactgt ggtgacttct gtggccctgt   2760
gatgttctca ctcaagagtg acttacatca ggattccatt cttaaataag cacactttat   2820
tagcaactat aactctgtat acattgtgtt tgcttttaat atttaacttt ttgttttcca   2880
aaaagagttc ctgaaacata caacaagcag aaattgtcat tgctgaagga tgcttagcat   2940
gctcatgttt ctgagtgttt actaggcgtg ataaatttga cttttcttgt tttctttcag   3000
ttcactctgt ctgatgctcc tgccccggtc tcctaaatgc agggattata ggtgtgcacc   3060
gccacaccta actgtgtaca gtagatcgta agatgggaaa tcccagagtc agggacctta   3120
ggtggctgac ctatacacag tgacatgccc aggaagtgtt aaatctggca tttgaatcca   3180
cctgtttgac cccagagttt gtcaaagggt aatagtacag cgctcttgca tgacttaaag   3240
agatgctcat tttcccaaga gaaccaagag gttctagtgg ccaaatgtca gtatgaataa   3300
atctgctgag atgcgctgtg cagcgtccgt cgaccttaca ggaggacaga gcaatccttt   3360
tcctttttga ttcatcgctc ctttcagact tgatcctctc accacagatc tctttccttc   3420
cacttcctca ttcaaaatgg ggtcagttcc ccctcagaac aaaagaggaa catgaggcga   3480
agaccctttg cagagggaaa atccacagct gggcgtaggc cgagggagct ttcgctggga   3540
gaagcaggtg agttcggatg aagggaagca actgagagag gcaaggcaga tcctcagacg   3600
gggcgggttg gggggggggc gactcggaga gggagttttc ggggagtcat cagagctggc   3660
```

-continued

```
caggaagaac taggcatgaa catgagtccc agggactccg agggacacat ttctgcttag   3720
gtcccacagt attaacacgg tccactaaaa gcagatacgc tcagcaggat gagcggccac   3780
agaggagagc ctatcagtac tcggtttagt cattaccttt taatacacat gatttatata   3840
agcctgtatg tgtataagac ttaagttata aatggctaat tacattacag aaggactaca   3900
gaaggcagag agagggaggg aggggagggc aagggtgggg aggggaggga aaggaagatg   3960
ctctttacct ataaggttta tctagtatct ttctaattgg tccttttagt ggcaattctg   4020
ttaacattca aatacaccat ggagagggaa gaacagaaaa cccccagatg cctggaactg   4080
gggaagctgt cttaaccctg acctctcttg ggatgctctt ctcatctata aactaatgat   4140
tactttagat cacttctgaa tgaccatggt taagtcctgg tctaactcta tccagccccg   4200
tagacctggt agacaagatg gacctgtgcg taactcttct agggctgatt ccacatggaa   4260
tttacctact tttatttaga gatgaggtct cactgtgtcc ctctggatga gctggaactc   4320
accacacaca ccagggtggc ctcagactca gagatttact tgccagtgct tctcaaatgt   4380
tggggtaaaa agcgtaagcc accacccaca gaccccatga attcatatca attgttattt   4440
gaactaactt gaccttccta ctcccctcag ctcacatcct caaccgtccc tgccttcccc   4500
tccagacttc ctcccccatt tccacgcttt tgctcaagaa gtctcatgat ctcgttcaag   4560
gaagctctcc caggttggct gacctcatag ctggcaacaa aggcaactac tgctaggggt   4620
gaacacaagg ctacagtgca ctcatcctgc acccaaactc agaattgcac caaagtgtgt   4680
gtgtgtgtgt gtgtgtgtgt gtgtgtgtgt gtgtgtgtgt gtgtgtgtgt gtctgtgtct   4740
gtgtctgtgt ctgtgtctgt gtgtctgtgt gtctctgtgt gtgtctgtgt ctgtgtttgc   4800
tttcactgtg tatgcatatg tggagaccag agacgaatga ggagatcata gacatacact   4860
gtcacaccca gcctttctgt ggatgctggg gatccaaact caggtcccca gatccatgca   4920
gcaagtcctt tgcccactag gctgtctccc gagctctgca cctaggctct ttataggacc   4980
agcagtgtgg cctcactgtc ctctatttcc aatctgtgtt tattacaact ccgctgacat   5040
attggggttg atttcttgga gggatgcttt tattctcttg gtgaaatatt tttctgtgca   5100
ctgatggctt gtgaaatttt cttctctgtt gcctcagttc aagccagacg aacaaggagc   5160
tgagattaag cttagtaagt aaagcccagg acctggagga tctggaaact gggtgaaaga   5220
gttgtcctct gttggctagg ttaggttcag ggcagccagg atggagtcag aggggtggct   5280
gacaacaccc aggggccact gtcagctctg tgactttccc tccagaaaaa ggggccagtt   5340
ctgtgcaaac atgttcttgt ccaggagttt ggtttcttct ctctgagcac ctggcacagt   5400
ggcaccaatg tgagcagtca cttggcaggg cagagaaaag caagctagca gtccccaggc   5460
tcaggtgaca gagccaggcc caggagacag ggatattgac tggggcttta acagcactat   5520
tgatgccaat ctcgggcaaa aacctgatat ttccacttgg aataacaaga aacagccaag   5580
aggattggag agaggtcagt ggacaaggag agccctctgc aggtcgtgct gggtgattcc   5640
agaacagaag agggcagccc ctgctggaca gggtctcctg agatgatggt gatggtgacg   5700
gtgatggtaa tagtgatggt gacagggaca atgacagtag tagtggctag gagaaggaaa   5760
aagaagaaag agaaaaacac aatgtcaggc tttaaataaa taatcctcat gaagtagata   5820
ctatttattg tggttttgat atgaaacacc cctcccccaa gggctcgggt attggagatt   5880
tgagccccag cgtgtggtgc tattgagagg tgactttgtt gatggcgact ttgtttgatg   5940
aggagataag aggtggactg taaggaggtg aaagctgtct gaggaagtag gtcaccagtg   6000
gtgtgctctc aaaggtgggt ctcaaccttc ccaatgctgt gacgcttcat ttaacacagt   6060
```

-continued

```
tccttatgtt gtggtggccc ccccaatcat aaaattagtt ttgttgctgc ttcataactg   6120
taattttact actgttataa atcataatgt aaatattttt ggagcttaga ggcttgccaa   6180
aggggtcacg acccacaggt tgagaaccac tgctctagaa ggaagtcacc tcctcttctc   6240
tccttgtcat tctcttttct tcctctccct tacactcccc ttcttctctt ctctctccct   6300
actcctcacc tctccactct ccatgaaatc tgatttcccc tgctatctac cacaatgccg   6360
gatctcatat tcccaagaag aatggagaca aacaaccctg gactggattc ctcctctttt   6420
aagtgtgact tgggtgttct gttacagcaa tgaaaagcta gcaatataag atggctagtc   6480
tcatctctta gatttaaaaa actaacattt tccaaacata gtggctcatg tctgtagaca   6540
cagagccagg gaagcagagg cagaaggatc cactgcaggt ccaaggctgg cctggactat   6600
gtaacaagag agagagagag agagagagag agagtagaga gagagagagg agagattgaa   6660
ggaaagaaag attgaagaaa agaaagatga aagaaagaaa gaaagaaaga aagattgaag   6720
gaaagaaaga gagatttaaa gaaagaaaaa agaaagatga aagaaagaaa agggaagaaa   6780
gattgaagga aagaaaagaa cggaaggaag gaaagaagga aggaaggaag gagtgcaggg   6840
ggaggaggga agaaaagagt ggagggggag gagggagaaa agaaagaaaa ggagactata   6900
tgaagctatt tgctcaaagc catgcatctt ctatcagaga gtagaatttg aactcaagtc   6960
attgcctctg aagcttgtat taccccacac acctgtcata gctcgtgagc acatttcaga   7020
aacttctagt cttctattgt gctgtttctt cctgttcttt ctagttatgt attcttgcag   7080
tgttaaggct taggggattg gatataaaat atcttgtgca taacaatatt ggcaatagta   7140
ataacaccag cttaaattta ttttttatag ctttagtaat ttaatttatg tatatgagtt   7200
catggtagct gtcttcagac acaccagaag agggcatcag atcctattac agatggttgt   7260
gagccaccat gtggttgctg ggaattgaac tcaggactac tggaagaaca gccagtgctc   7320
ttaactgctg caaaatggta cagttactct ggaagacagt ttggcagtca cctgaaaaac   7380
taaacatact ctttccatat gatattgcaa ccatactcct tggtatttac cgcaccccca   7440
aaagctgaaa acttgtctaa ataaaaaccc tgcacacaga tgtttgtagc aactttattt   7500
ggaatcggca aaaactggaa atgaaatgac tttcagtggc tcaatggaca aatgaattgt   7560
ggtactttcc tggccgtgga ccatcattca gtaccaaaat gagatgagct gtggagctaa   7620
aaaagacatg aagcaacctt aaatgcacaa gtggaagaag ccaatccaag gagctgcata   7680
ctgtataatt ccaaccccat ggcatcctgg aaaaggcaga accatggaaa caggttttta   7740
aaaaatcaga gattgccaaa ggctaagggg agagtggatg gctgggggca gcagagagga   7800
aagcacccca caaccatcat ggcggataca catcctcgtg gccgttctgg gtttacagca   7860
agagaaacca caccaagaga aagtcctaat gtgaactaga aaccagtgat catgctgtgc   7920
caagttagat ttgtaagtcg taaacaagct actattctca ctggagatgt ctagagtaga   7980
ggagactgtg tatgccaggc agaaggcatg tggaaactct tagtgccttc tctcagttta   8040
tatgtgtttg tgtgtatgta tacatctttg tgtgtatgtg tgtgcatgta cacgtgcgta   8100
cacacagaag tctgaagtcg atgttttcct atatcactct ccaccttagt ttttcagaca   8160
gggtccctca tgaaacctgg aattcaccag tttgttgggg ctaactggcc agtgagctct   8220
gggcatcctc atgtctctgc cttctcagct gggattccac gtgtttgcca ccacatcctg   8280
catttacacg ggtgctgaga acccaagctc aggtcctcat cagtagggca agcacttaac   8340
tgactgggcc atcttcccag gctcttctct tgctgtacaa ttaaaagtat tctttgaaaa   8400
agtctaatat gcatgcctat atttccagca ccgagtaagt ggagctaacc tgggctagac   8460
```

-continued

```
agtaagaccc ggtcttgggg gtggggaaca cctaacaaaa aaataaaaac aaaacaaaac    8520
aaaacaaaaa ccaaaaacat taaatgaaga gccagggcag tgacaagaca cgtgactcct    8580
caatctctgt ccaactctgg aattcaatag gctacttttt ctgttttcct catccataaa    8640
tagaaaaagg gataactgtc tcacaggatt gtcacagaaa ttaaatgaga tgctgctgga    8700
tggattagca gtaggagcat gtagcagcag acctgtgcaa ctctgtgtct ttccactgat    8760
ggcatcatag gctactgctg ggcaaggacc tattcatttc ataatcgcct ctacctagcc    8820
cagtatgtgg tgtttgagcc ccctgagtct gctgggttga tggtaagaac tagcctagac    8880
ttctctctct ctctgttgga catttgaggg ttttctcaac tttttgctat gagcaaagta    8940
catctcaaaa cccttttatt tacatcacct aatttgatct gcatcccagg tgaagccagc    9000
agaagagggc tgtttgccca cgcccacact ctgagacaga cagaatcact atggctcaga    9060
gaagtgaagg gacctcttcg ggtcacaggt atatcagtga tggtgatgac gatggcggag    9120
cctctggccc tgcttctcta gcccctacct ctgcagacct tttctctct gcctgctgcc    9180
ttctgcatca gaggtctctt aaaaaattgc agccttgtca cgctgggcct ggtccttctg    9240
tccgctgtct ggagggcagc acctttgccc agtggtccct gctggggatt gtgaactgca    9300
aactcccaga tggcctctga aatcaaatat tttatttcca atgcctctat tttcccagaa    9360
tgaggagcac accagttccc ccacacacac acttgctttc gtccctataa agaggtgagg    9420
agatgactct ccgtgtccag gaggaaggac tttggctaaa aatagctgtg gcgtgtggat    9480
tagccagagt ggtacccagg actgggaaag ggagggggac gctgtggagc tgtagccaga    9540
ctggttgcca tagaaacgag agaggagcag gggaacctgg gaagtgggga tgacacagat    9600
accaagtcct agtctgagct gccgttacat tcaggagaaa cagcagtgtc ggcggctccc    9660
aatctcagag ggaacctagg gtactggggg agatggtgtc agggacatgg acgccaaccc    9720
ccaagggtct ctgctgctgg ctactcttct ctccaggctc tgtgagttga gttgtgggac    9780
ttggggtttg ggcccctatt tctgagccaa gaggggtttg ggtggagctg ctcccagagg    9840
gacttctccc cgacagaccc ctttccaaaa gataagcccc ctgtactggc cagcgctctc    9900
tagagggagg tggagtactc caagataatg tggtgctcgg atcttactga aaggggtcac    9960
agcatgccca agaactgtgg tcggaagaac tggagttatt tggagggaag aggaagaaat   10020
gaagacgttg ctcttcaggt ggtggacact gcacaccttt cctgtcccat gaagaagaga   10080
gcttttctcg agatggcaat ggctaggatg tcatcagtag gctccctggg cagtcgtgtt   10140
ctgggaatga tcagacactg ggaatccttc cccattcctg gccgtagatg gaggtcagat   10200
caccttagac cctacgaaga ctgtctagaa gcccacctga agttaatact aggatgaaag   10260
agacctgggg tctcgaggca ctgaaaactt acagatgagg tgcagaggac atcctgggct   10320
gcagagaggg aaaaaacaag cctgcttgct gttgggggag gggaagatct taatctgcca   10380
ttgccgaagt gttcccaggt catgtctcct gacttccatg gaaaataagt gtgtggggtt   10440
acaaaccatc tttttggggt tttttccttg tgcctttctt taacatacac acaccctcca   10500
aaggtctgct ggctacagaa cacttggctc caaagtttaa aaatggaatg tcgggtttgt   10560
gggtatatat tcatgcagtt tctccctagg atctggtcaa acatccaaac catctgagat   10620
ccttatgtca catttctgcc cccacagggc cacctgctct ccccacttcc ccagccttcc   10680
tgccccaccc ctcaccctga atgggaggag atggcaaatc ccaggaaaga gaaaggaagg   10740
ttgatgagtc ttaatcctta ttctacagac ttctgttcat acggtccata tctcctaggg   10800
gaccctgaaa gcctaggaac cgactctggc catccatctc tccgggaaga ttataaccca   10860
```

-continued

```
gagtgcttct caggggggaa gaatttgaag caaaaccagg tgggttttgc ttggaatctg  10920
ggctttgtgt ggaatgtggg ctttgggaca tatggcagga gtgggtgggg ttgctggtag  10980
ggtagtaaat gcaaatcagg aaattggtag ggggggtcga tgtgggtgtt tggtgtttcg  11040
attggtctga tttcttatct cttagaagaa tacgaatctg agagatacta gactagcgta  11100
actctggatg gcctggcgcc tccttcatcc ttgccgtggg cagttgagct cacgcgtggc  11160
ccccaatctc ctattgccca cccttttcag cgtgtctcct gtgggaaaga gccctggcgg  11220
gaaatgggct ggtatcagag catcagtgac cacggtgaag cagttagaat tgccagtggg  11280
aagttcccaa tgctgaggac atccaacctt tgcacactgg aggtttttgt gcacagtctg  11340
cattgctttc tccttgggaa gtctggggtg gaggggaaat gtagcaggag aaagagtgag  11400
gccagggaga acaccgaggg aacagtcttc aggtggggct tctggcagga tgctgaagag  11460
tgctggggga agggataatt gccagggaaa gggctgtgga agtcctcatc gcagggaggg  11520
ctttgcatgg agaaggaact gccaagaagt ctacctcttc agtaccctaa atgtctgatc  11580
cggggtgcct gtgagttgct acatacacca gcttgaggta gtgacgctga gatctgtgac  11640
atcgagatgg ctaatgcctc ttttcttact gaacttcgac acccagtctg tgctctttat  11700
cctgtgtaat ctgtacaact ctctctctct ctctctctct ctctctctct ctctcataat  11760
tctttattct tttttaaaaa gatttattta cttaatgtat atgattacac tgccgctgcc  11820
ttcagacaca tcagaagagg gcataagatc ccattacaga ttgttgtaag ccaccatgtg  11880
gttcctggga attgaactca gaacctctct ggaagtgcag gcagcgctct taaccccgct  11940
gagtcacctc tccagccata caactttttc ttaaccattg ttttatttta tgtaatagtt  12000
tgccctcatg tacgtctgtg cattaccctc ggaggccagc agagtgcgag ttacagccgg  12060
ttgtgagccg acttgtgggt gctgggaatc gaaatcagat ccgctggaag agcaaccagt  12120
gaatcatttg agccatctcc ccagcacttg tgccccaact ttctgagatt tatgggatgt  12180
tagggattat cgttcccaat ccaccagtgg ggaaaaacta aggctaaaga gacaggaagg  12240
gagattgtct cacagcattg gccctgagtt cggggcagat ccatcaactc ggcacacctt  12300
tattaagacc ccgcaggatc cccgctgcgg ccgccatggc gcaggagaac gccgctttct  12360
ctcccgggtc ggaggagccg ccacgccgcc gcggtcgcca gcgctacgtg gagaaggacg  12420
gtcgctgtaa cgtgcagcag ggcaacgtcc gcgagaccta ccgctacctg accgacctgt  12480
tcaccacgct ggtggacctg cagtggcgcc tcagcctgct cttcttcgtg ctcgcctacg  12540
cgctcacttg gctcttcttc ggcgccatct ggtggctcat cgcctacggc cgcggcgacc  12600
tggagcacct ggaggacacc gcgtggaccc cgtgcgtcaa caacctcaac ggcttcgtgg  12660
ccgccttcct cttctccatc gagacggaga ccaccatcgg ctatgggcac cgcgtcatca  12720
ccgaccagtg tcccgagggc atcgtgctgc tgctgctgca ggctatcctg ggctccatgg  12780
tgaacgcttt catggtgggc tgcatgttcg tcaagatctc gcagcccaac aagcgcgccg  12840
ccactctcgt cttctcctcg cacgccgtgg tgtctctgcg cgacgggcgc ctctgtctca  12900
tgtttcgcgt gggcgacctg cgatcctcac acatcgtcga ggcctccatc cgagccaagc  12960
tcatccgctc ccgtcagacg ctcgagggcg agttcatccc tttgcaccag accgacctca  13020
gcgtgggctt tgacacgggg gacgaccgcc tctttctcgt ctcacctctc gtcatcagcc  13080
acgaaatcga tgccgccagc cccttctggg aggcatcgcg ccgcgccctc gagagggacg  13140
acttcgagat cgtagtcatt ctcgagggca tggtggaggc cacgggtgcg ggcaggctgg  13200
aggatgggag cagggatgca ggacaagggc aagaaaagca gccaggggag gcgcagaaag  13260
```

-continued

```
atggacagag aatggagtgt agggtgacag gcctgagggg tagcgggggc cggggagagg  13320
acgggagatg acagggatgg acagggtgac tttgcagagt caagaaaagc ttggaagagg  13380
tctatgaaat ggcactagct tgaggccctg acctgacagc tatgtcactt tgaactacat  13440
tttacatctc tgaattcatt taagcccagc aaagctcccc tggaggttac ttttgactgt  13500
gctcggtttt cagagaatga gtagccccaa agaaaggtcc cataaatagc ccgctgtcac  13560
aagccaataa atagcacagc ctgggttgaa cataggacat ctatcttcag tgtttcctgg  13620
tacagtgttg ggatgaaggt taagtgcagg gttcttgaag cccagaggtc catagctctg  13680
gaatttaact gacctaagta aaagggaggt aggtaggaaa aagactagta ctggagcaaa  13740
aacaggtcct tgaagaggtc ctagccgtca gggagcataa ggaagacgca ggtgaaccaa  13800
gaggccacta ggaggagctg cggagctgct acggacaggc tagctccctg ctgctagcct  13860
tgaaacctgg ctcctgggcc tagacaaaaa catcatcttc tccatggcca cctcaggtct  13920
tcccactccc ctctcctcct tcactccaac taggctggtt ctagcccatg cccattccac  13980
actgctccct ctgtctctgc gctgtccctc tctctgacac aatctcggac aggtttctat  14040
cagggacttt ttcatctgcc ttctcttccc cctctgccac tgcctccact ttgcacctaa  14100
ccctactccc ccaagcccta cctctgcttc tcaggccttc tccctgcaga ggccccggtg  14160
gcctctcttt ccctacgatc cctgatacat cttattccag ctttgccaaa gaataccaat  14220
gaccccaaga tgtctcaggg ccagacttcc gatgtcagag ccggtctctg attagtgaat  14280
gcttactcct ctgtttttga gatggattcc ggtttgggaa gattctgagg taggaacaaa  14340
atgatctgcc ccgaggggag ggtgcacaaa cccaacagag aagacaggac acaggctcag  14400
ggcaagaact gggaaggggc agtgtaaagg acatggggat gggagcttgc ttgacttttc  14460
tagagataag gctgggaagg atggtagtat tttgggattc aaactgcttt tgaaaagcaa  14520
gaataatgag ccaaaaccca acatgatgac atttaagggg aataaatata aaattctaca  14580
tttaggcttt aaaaaaatca cttatgtaag cacagcatgg aaaggctccg gtggagaaag  14640
aactggggggt tttagttggc cactggcttt gctgcagcaa cgtgatgcag cttccaaagg  14700
cgtttatgta atgtaatcat gggcccgctt caccaaagca tctgggcgag aagcaagaga  14760
tagtaagcct tcttttatgc acagataagg ccacagttga aaaagcactt cagatgagcc  14820
cttacctggg cctggtggcc attctgattt gcaatgaaga ttgtaagctt tgggggagtc  14880
agatgaagta agaaatggcc atgagtgttc aatctgagga agagaagatg taagggaacc  14940
ccatatttac actcaagggg gtgtcaggtg gtaagggaat ggaaccaggg gccacgggtc  15000
ctaggagaca gattttagtt tatgtaagag aaaacccaga gccaaagaga tgtctcagct  15060
tgcaaccacg cctgactact gacctgagtt gaattaccag gtctcacatt ggggagtcaa  15120
ctgtctcccc aagttgtcct ctgacctcca catacataca tatgcacgca tatagacaca  15180
taaatgtaaa acacatttgt aaagacgatt ggcacgttgc acaaaggact ggacttttaa  15240
tgagatggtg agctttcaat cctggggtgt aatcagttca gcccattgtc tgggaatgct  15300
tgggggtggg tggaggcggc tctgtgggaa acaggaaggt taggcttaag gttaagcttc  15360
tcaatggaga gtaggggaaa acataggctg gcagatagag aagagggcta actaaaaaga  15420
gaggtgggac tctcagagag agaagagggt tgtgggatga cagacaggag aaggaatcct  15480
ctgtcagggg cccctttgac tgatgccgct tctcctcccc ccacccccca ggaatgacgt  15540
gccaagctcg aagctcgtac ctggtggatg aagtgttgtg gggccaccgg ttcacatccg  15600
tgctcaccct ggaggatggt ttctatgagg tggactacgc cagcttccac gaaacctttg  15660
```

-continued

```
aggtgcccac accctcgtgc agtgctcggg aactggcaga agccgcggcc cgccttgatg  15720
cccatctcta ctggtccatc cccagcaggc tggatgagaa ggtggaggaa gaaggggctg  15780
gggagggggc aggtgcggga gatggagctg acaaggagca caatggctgc ctgccacccc  15840
cagagagtga gtccaaggtg tgactggttt cctcccaccc cctgtggcag accaggggc  15900
cggactcagg tacacagaag ctgcgagtgg aggtggaaga agaggaggca ggcagtgtcc  15960
cgaggaacag ctaaagttgg gagaggcccg ctgagtccag gatcgagtag ggaaggctga  16020
ggtcctggtt tgaagagaga gggttgcagg gcggggtgag agaacatgtc agtctgtctg  16080
tgtttgacct tcacatcggt tcatgggtgg atggatggac agaaggatgg gctcatgggg  16140
gttgatcggg aaggtggagc agatagagac agccaatgga taatcgctca ggtggtaagt  16200
ggcttggcag tcgatgatcg tcacctgcag cacacctttg tgagaaatcc atgggcatcc  16260
ttttcttcca gatataggta gcctcaaacc agggagcgtg gcttagggag caggctgtca  16320
ggtggactac cacccccact cacctcccct caactggcct ccctatgtgt gacacgcctg  16380
cctaactaga gaagagagca ctgggtagag gtgggcacag gtgtgggtgc cctccccagc  16440
atcactgtcc catggcgaga ggtcagaaag gcaaacaagc aatgggggta gatgctgagc  16500
agggaggggc cctgaagcag gacctgggga cagccaagga caactatttt gtgagagagg  16560
aatgaaacct tgcaggtcct gccacagaag caagaagcag aggaaaggcc atggagagac  16620
ttaataaagg gttttacaag ggtacctgga tcccaggggg aagtagttta tccttggggc  16680
acagtggcag ggctcattca gaacggtgag taagtgtcag gtgtgatatt caaagacctg  16740
gttcttaaca cgagagcaca gcgaaggtgg aggtcagaaa taactcccag ccactgaagg  16800
aagtatggct tcagtctgga gagctcagaa aagactcgac cctaggagcc cacacaagcg  16860
gttatagcca caagtgagag ggcattaggg acaggaagct aaggattgag taaggcagtg  16920
gggaatggtg ggagccagca gttacaaagc tttactcacc tggatgggct tgttaaaaca  16980
cagattacca gccccactcc ctgcattctg actcagtagg tccgggacgg aaaccaaaaa  17040
aaaaaaaaaa aaatctgcac gtctaactag ttcccagacc taacaggttc ccagatcgcg  17100
gtgacactgt ctgtctgggg actgcacttg ggtgaagcat ctaagcggaa gagaagctgg  17160
aggaactgaa aagcacccca ggttcctcaa ggaacagaga aacaagaagg gaaatgttgg  17220
ggagagggga cccaggtcca gactcgaagg gcttaactct gggtccaaga aacgtcattg  17280
gtaactggcc agtggcaccc gagagggcaa cagagatagg agaaggccat ttagggaccc  17340
ccaaggaggc agtggggggt ctgtagctga attggcctta ccacaaaaga ccaactctct  17400
taagagactc acaaggcaag actgactagg ggagaaaatg gagcctgtac ctacaggtgt  17460
ctgctgtctg ccacctgtcc tcccaggaca gggcaccctg gagacacatt ccacctccac  17520
tgcatccttg tcttgcccca gtcatcttgg gatggttgag gggacagcaa cagcatggca  17580
atggacctga ggctggcccc cctggagcta agtgtagccc aagtgagcac gtaacctgat  17640
aggactggct cagactctgg ccctggctat acccatccct gccctcgaat aaaagtctgc  17700
tgctctgtcc caggctaaga agccagcatc caatggggca tcgaggcctc cctcccagtg  17760
cccagctcag agtgggtcca cgcagagagg actcaagctg cctgttgcct ctccccttcc  17820
atctagcaat ggccacaggt ttcgggacca gctgggtcac tctcaaagat gaggtccacg  17880
cacatgaacc tgctgggatc ccacgaacac atattggacc tgagcacagg gactgagcag  17940
ggtttgaatt cagagaaaat cgaggagtct agacaagagg ggtggggtgc ttggtatccg  18000
cacacgaagc aatggaatgg agacattgaa gctgttcctg gaggtcactc agggcaccgc  18060
```

-continued

```
tgtccagggc acagccagga gacctgtgtt ctagcaccaa tgctgattgt cactaattac  18120
ctctatgact ctcagcaaga cctattactt ctctgggcct cagcttcctt atctgttaaa  18180
aaaaaatgat atgttggcaa actcaataat gctcaataaa ctttcaacta ctgaatgaaa  18240
aaaggtagac tggatgccgc tcaaagtatt aggacagctg aggctcttag gaccggagaa  18300
ccctttaggc ggggagttgc ggctagccag caggcaagtc ctggcatcag atgtaagcag  18360
atgaggcggc tcttgtgtac acagaggaca caggctctcc caactgctgc tgtccttaag  18420
taggcagccg tgttctgaag ctcctattcg gctgctgtca gagaataatt aagggcagga  18480
ggaaaaagac tgaggcccca gggcctgtgg gaggagtctg gtccaagact agttcaacca  18540
ggagaaatgg accagaggag ggtgtgcccc agtctggaga gctcagaaaa gactcgtccc  18600
ttggagctct gtgaaagggg caaagctcag ctggaactca cccctcctct tcctaggtcc  18660
cccttcccaa atagaagccc cattaggact tggctcagca cagacatttt ggacaacaga  18720
tgggaccccg gcatcccctc atgcagttgg tgggtaacaa ggcccacgaa gggacagatg  18780
gtgtttatgg tgggaagaga ggcccgggtt gtccagcaac caccctacta ccaccccacc  18840
cccaccccccg atgctgcctt ttatagcttc accgcaagag aagacacaac aggcctcgat  18900
tttacaaaac cagtttattc acattttaga aaaactagtt tgaggacagg aactggcctt  18960
cctacaacat gagtgtggga ctaagaacgg cagccaggaa acttgaggga aggtggggac  19020
aggggagcca tgtctcccac tctaggtgat ggctggtcaa ataaattaaa ggtgggctgg  19080
acagagggag agggtatcca ggcaaccaga ggaggggtgg cactggctgg aagacagtca  19140
acacctgcaa gaactggaaa gagcatgtgg agtcggctga ggaagaggct ccctttgacc  19200
cttaccctgc tatacgatcc tgcaggactg tgaagctggc tgcttctccc cctgatggtg  19260
cccaggtaca gctcagcaca ggaagcctga ggaaaggcag ttcctttccc tcaccttggg  19320
gtgctacaga tcaccgcttc cgcatcctct tcataaagca gcaggtgatg gtagccagga  19380
cgctggcgcc ggtaactagg gcgactcctg tacccaccaa caggggcaca aatagggtat  19440
ccacagctgg cagaaaagaa gacaggctct gctcagagag taccacggta tctgacactc  19500
tcccctgcag attttctaga ctcagccctc cccaagggag agctgagcgc cagtcctgcc  19560
tacctacact tcacacacaa acacaaccat cccccatccc ccatccccac cccctcccct  19620
cggtctcagc actcaggccg gcttggggcc cttcatgcaa agggatgtgg aaaaaggatt  19680
gcaagggaag acaggaagat ggaaaggggc aaacagagca ggaacaggtg ggtagatggt  19740
ggctgtcact caccatgcgt gtaggggtag actgtaacag gcccggagcg cgcactgcct  19800
gcctggtacc agctgtagtc cgcatgctgc acccaggcac ttggggcaca gtggtatatg  19860
ccttcatcct caggccccaa gccatgcagt cttagccgat gacttctggg tcccaccagc  19920
tccacactga caggaccccc tccaggccgg actcccagct ctgccacacc gtcctgaccc  19980
actccaccca caagctgagc agggccagag ctcagctcgc cctcctctgg cctctccacc  20040
caccagctgg ctgctagtcg cagccctggg gggccgcccc gcacagagat gttgcatagc  20100
agggaggccg tctctccccg gtacacagtg ccccctgcta gccacgccac ggcctctagc  20160
accacgcctg cagagcaaag aacacggggg ttaccaggtg aaggcccagg ggctaagagg  20220
ttaggaaata aattctataa gttctgaacc ccgtcaaggg ctcaacatcc tcttaccttc  20280
ttctctcaca tgcacaggga gaggccggga acgagcactg gccgcttcac gaagtcgggt  20340
cccagaccct cgaacatagg ctttggcgag gcagcggtag gtacctgcat cagcgggcct  20400
ggcagcctcc agccgcagtc ggtaggttct ggatgctact ttctccatgg caatgtgccg  20460
```

-continued

```
gtcctcatag ccagggccca ggctgcctat accttccgtg tctagctggg ccaccaggcg  20520
gccgggtcca ggagcccctg caggggccat ctcccagccc acagagtacg cagcatgacg  20580
gcctggtggg ggcagtgcac cggacacatt gcacagcagt tctaagggtt cgcctgggcc  20640
aatccgacgt tcaccaggtc ccacggtcac cgccagctgg ctggctgaaa cacagcagga  20700
gatgggagga gtcactgaga tgcctgggcc ccccacctgt aattcttctt tgcagaaatt  20760
tagaggcctc ttatatctcc ctcaccccag gacccgaatt tcacccttcc ccccatagcc  20820
tttgtatctc catgcttgtg cggcactccc gatgcccaac tgagagacac cccccccccc  20880
ccagtgggct atgctgcact cacatagagt ctgcacatca acatgagcca ggactgccct  20940
cttctctgcg acctggaccc aggagccgtc aggatcctga atccactcag cggccgtaca  21000
gtggtaggtg cccgagtctc cagcctgggc acccccaacc accattcggt accgatcagt  21060
cccttccttg ctcagccgaa gctccccaga agctagcctc tcagcgtagg gcgctccagc  21120
ctccaccgcc atgtcggagc gcagtcccac tacttcctgt agagtggctc gccccactgg  21180
cgcctccgga atggctctcc caaaggacac cgacaggtgt gtgtgtttct ttgttttggt  21240
ctgagccagg cagcccagcg caagctcctg cccctcgtgc actgtgaggc gtgaggggga  21300
ggtggcagcc tggcgccctc ggggccctgg aggggcagca gatacctgca gctcatctgg  21360
aagaactgga gagaaaggct ttagtgagag agggcttgga gcagcatccc tcctgtttcc  21420
tgtgcgtatc ctgtttcact acacactctc taggcttcta gaatgtaaga actgtgctct  21480
gtagcttttc ttctataccg cagagatgcc aagcttggtc tgggcacatc aagatattca  21540
ataactactt gctgaacgtc acagagcaag cctactgacc cctactctga tgtctaagac  21600
tgatccattt taaatactca aaaaaagtaa tcctgtcttc cttctctaaa gataaagagg  21660
ctggacctga tggtgccggc ctataatcgc aactacccag gaagctaagg cagaagagtc  21720
aagttcaagg gccgtctggg ctacagaaca agttcagtgc tggtctggtc aacttggaaa  21780
gtttctgatt cagcccatcc cccccccaa aaaaaaaaaa aaaaaactgc tggaaagact  21840
ggcttgatgg cactggagct gacacaatac tgcctgagct acacagtgaa ttgtgggagt  21900
tttgtcacca gtttcaggcc aacctaggct agttgtaagc tagcctgggc tacaagagtg  21960
agccctcaaa aaacaacaca gggaatatag cttagtagag tgctcccttg gtatgttcca  22020
tgctgtaggt tcaatttcca gtactgagaa gatgggggtg gggggagaag aggagaagga  22080
agaagatgac agagaaggag gaagacgaag caaaaataga tctgagcgtg ctggcttata  22140
cctataaccc cagtgcttgt gaggctctct caccacctag ctcagagccc agtacctctc  22200
agctccacct tggcactgta gttgcccagg tactgcgtat ccgtggaggg ggtgtagcac  22260
tcataaaagc cagagtcctg ggcctgcagg cgagcaatct tgagcaccac cgaatctccc  22320
ttcaggcgct gcacctgcag gtcaccagat gccacacgag gcccaaagac agcataggag  22380
aactggctat ccttggtgct gacaatgccc agggacgtag ctggggcctc tggtctgtac  22440
atgaaccact cgaagtcttg ctgggcaggg ccctcatagt cactcacgtt gcaggagata  22500
gagacagcgg tgccagccac ccggtaaaga ggtcccctgg ggacatgcac ctgccgggcg  22560
tagcacctgg ttcctgtggg gtaaaagcag aaagaactgg aatcttttta gagagaacga  22620
gtccccactt gatggccagt atcatcagca ccattcttga ctgctgcctg tgaaggaaag  22680
ggaaacctag ggatggttag aacatagctg ggcaaagaca cagatgggaa cacaagatgg  22740
gacacgagac accagcatcc cagcacatca cgtaggttca gatccacctg aacagaggaa  22800
tactctagct aactagaggc agagcaccta catgaacaga ggagtccatc cggagtctgg  22860
```

-continued

```
ggtatagaca gcccggtaag taaaatgctt tccatgcaag catcaggacc tgagttcaat  22920
tcccggcaac tatggaaaaa gcttggcacg gtggctggtg agtagccaca taagcctgac  22980
aacctgggtt tgagccccac aagggaagga aggaactgaa tcctgaaagt tgtctcctct  23040
ctctctctct ctctctctct ctctctctct ctctctctct ctcacacaca cacacgcaca  23100
cgcacacgca cacgaataaa tgcagtggac ggttcctgag ccatgacccc tgaggttgac  23160
ctctgacctt tacacagaca cctgcaccca tgcatacatg tggaccctca tacgcatgca  23220
attggaaata acaaataaaa gaagcatgcc tgattcccaa ctctccagct cgtggctgga  23280
tctttatcgc tcctaccctg ccatgtgtgg cgtctctccg ggctcagaaa gaacttctag  23340
ctaagggatt ctgagccttt tgctggaggg gagctgacaa catcttacag aaaggctgct  23400
tggcttagct ctgtcacctg ggctagacaa tggagccagt ggcccaggct ggctggggta  23460
ctgcactgga tggggcacca tgctggacag ggcacggacc tagtcagtcc tcactacaca  23520
ataccctccc cactacagct gtgccatgag ctcactgctt ctcccagccc acaaggctac  23580
acaggcagct gtggcttctg gggcaagaac caggctctgc ccaggcctgg ggcagaagat  23640
cccttccccg cccccagaat ctgtcaacct tctcgctaac ccagatgatg cactatgcac  23700
agccccccaa acaaaagctt tcatttacat atgatttgcc tatctgcgca gcatttgcat  23760
agacctcctt ttaataagga gaccccaaac acctgctgcc ccttccccct tctctctctc  23820
tccctccctc cacccatttt accccaccac tgttccaaca gacagccggt tccaaaacct  23880
tggactgttc agcttctttc tcctctccac tacttctagg taagaccgca gaaccctaga  23940
atgcaagacg ggctgtcaat cattcctcag atgagagaaa tgaagaaact cccagagagc  24000
acctctaggg agcattgcca ctaggttcta accacagatg tgagtctaga gctctctccc  24060
agccaacacg gaaggcctgg ccgtgagaac catctctctt ctagatgaga aaagtaaagt  24120
gaaatgtgac attgtggcca agtccctgcc ctctctggag ggcctctaca cacccctgaa  24180
gagggacaaa accaagaagg cggagatgct tccaaggaga gccctggttt acaaaactgt  24240
aatttcccgg atttccaggg gtaagtccac agcttgctac tggccctgga ggaaaccacc  24300
caagagcctg agagcctgct ctacagttct cgctcctttc cttcttctgg ctacgtcacg  24360
cagagaacac atgaccaccg cctgaagcag aggctagagt cagaaagcca acatgagacc  24420
aaccctttcc tctcctggat ctcagtttct atctctcaga actaagagct cccagttctg  24480
atgttgaacc cgtgagtata tgtgtgtgac tcaggcacat atcgctccag gcacatttca  24540
taatcaggag gatggttaag gcagccaagc tgacaccatc ctggctgccc atgggtaaac  24600
tctgctgaga aggtcccctc ccaccttcct ggctccacac aagctgatgc ttggagatcc  24660
ccatgggaaa gttgtcccca cagcctcagg acataggctg ctacaaggtt ctcaatggct  24720
gggctgcctc ctttctaaca gccaaaggtc tgctttgaag tcagttctga gttcaaatcc  24780
acccccaccc tcactggata cacagtggta tttcacgaca tctgtgaagt gaatgccagt  24840
gctggctgca gtgggctaaa atgacattca gctcctctcc cgcccctgaa taacactcac  24900
tcctcccaac cacccctggg ctcatccctg ctcgggttaa gcccaaagga aaagaagcaa  24960
tcgctaggca accaagcccc acagctcctt caactcccta catcactctg cctcccgcct  25020
tgttcccaaa ggagttttca tcctggcccc agaagcccaa ggaaccattc tgtacaacac  25080
tgcacagttc tggtataaac cagagaagga ggttggggtg ccccactata gtatcttctc  25140
catatgcata tcacacacac acacacacac acacacacac acacacacac acacgttcct  25200
ttcaagggct tcagtctcct ggcaactgct ccatgccata tctttcccag accacctcct  25260
```

-continued

```
acagggagcc ctccaagtca gaccccaaac atggtaatgt tagcaacctc cacaggcctc  25320

aacacacaca cactcacact cacacacaca caccagacat gacgcaaggt tggcccagaa  25380

aacacaccat cataaacacc caccaggaca gacactgggt gcttagagat cccaggttca  25440

gtttccatgg agcctagttt ctcctgaggc agggatgttg ggaccaactg agtctgacaa  25500

ccaggcaaat atctgggagc gtggaagggc aaagagggaa ctggcccagg gtggagacac  25560

gtgagggaag aagcctcaga tggtgacatg ttatattggg aggtgggggt gttggggaga  25620

ctttttttcag agatcgtggt cagaatcagc cctgggcct ccagccaact ctgggcaatt  25680

atgaagaccg ccaggcactg cccacgcaga gcaaacaccc aaaaccaggc cttgagccga  25740

gagtggggca gaaggttgtc acggtatttg gtagcaacga ccccagacgc tgggtgtaac  25800

cgatgagaag tggtgcctgc ctccggaggc ccgatggtgt ctcaggggat acctcagtag  25860

gtcgcccata tgccccagct aggaacctag agcgaggaca ccaccaccct ccccataact  25920

gattgggcag acaggcgcaa aaggaagcga gacgccgagc ccagagacag tggaggcacg  25980

tctgttggag aagtagggat gcaaccagct ctgaaatgct aggaaggtgg gctggtgggc  26040

tgcactatgt taggcaccta cccggccggg acagggacgc ggcgaccacc acctggctta  26100

ccaagtatta gcagcagcag caggagcgaa ctcagcggcg tggggctagg gacgcccatt  26160

ctgcgtaggc ggctctgggg agactcctgg gggcggcgta ggctctgggg ggccagggcc  26220

gcggggggcg catgcccagg tggggggcag aaagcggagc agtgaagcgt gggtgcgcag  26280

agcccagccg agcgggagcc gccaactccc cgccctccac ccttcttccc ctcctccctc  26340

cgctcttccc gccctccgca gctcgggaga ccagtcccag ccgcgccccg ctgcccggcc  26400

ccgcccccgc ctcgccccgc cccaggccgt cgcctcggcc agacttcgac cctgatggtg  26460

gctccgcctc tggcctcagg ctgggcgaac tggcggcacc tgggctcctc tatccccatt  26520

tcctcgctca gagggcaccc cgccctgcac ctgccagcct tccagggaga atggggtgct  26580

ttcagggcct ctggggatgc atgatggggt gactgtggtt acgcactcag aatccaattg  26640

gg                                                                 26642
```

```
<210> SEQ ID NO 2
<211> LENGTH: 2267
<212> TYPE: DNA
<213> ORGANISM: Mus Musculus

<400> SEQUENCE: 2

ctgagctgcc gttacattca ggagaaacag cagtgtcggc ggctcccaat ctcagaggga     60

acctagggta ctgggggaga tggtgtcagg gacatggacg ccaaccccca agggtttctg    120

ctgctggcta ctcttctctc caggctctac ttctgttcat acggtccata tctcctaggg    180

gaccctgaaa gcctaggaac cgactctggc catccatctc tccgggaaga ttataaccca    240

gagtgcttct caggggggaa gaatttgaag caaaaccaga ccccgcagga tccccgctgc    300

ggccgccatg gcgcaggaga acgccgcttt ctctcccggg tcggaggagc cgccacgccg    360

ccgcggtcgc cagcgctacg tggagaagga cggtcgctgt aacgtgcagc agggcaacgt    420

ccgcgagacc taccgctacc tgaccgacct gttcaccacg ctggtggacc tgcagtggcg    480

cctcagactg ctcttcttcg tgctcgccta cgcgctcact tggctcttct tcggtgtcat    540

ctggtggctc atcgcctacg gtcgcggcga cctggagcac ctggaggaca ccgcgtggac    600

cccgtgcgtc aacaacctca acggcttcgt ggccgccttc ctcttctcca tcgagacgga    660

gaccaccatc ggctatgggc accgcgtcat caccgaccag tgtcccgagg gcatcgtgct    720
```

-continued

```
gctgctgctg caggctatcc tgggctccat ggtgaacgct ttcatggtgg gctgcatgtt    780

cgtcaagatc tcgcagccca acaagcgcgc cgccactctc gtcttctcct cgcacgccgt    840

ggtgtctctg cgcgacgggc gcctctgtct catgtttcgc gtgggcgacc tgcgatcctc    900

acacatcgtc gaggcctcca tccgagccaa gctcatccgc tcccgtcaga cgctcgaggg    960

cgagttcatc cctttgcacc agaccgacct cagcgtgggc tttgacacgg gggacgaccg   1020

cctctttctc gtctcacctc tcgtcatcag ccacgaaatc gatgccgcca gccccttctg   1080

ggaggcatcg cgccgcgccc tcgagaggga cgacttcgag atcgtagtca ttctcgaggg   1140

catggtggag gccacgggaa tgacgtgcca agctcgaagc tcgtacctgg tggatgaagt   1200

gttgtgggga caccggttca catccgtgct caccctggag gatggtttct atgaggtgga   1260

ctacgccagc ttccacgaaa cctttgaggt gcccacaccc tcgtgcagtg ctcgggaact   1320

ggcagaagcc gcggcccgcc ttgatgccca tctctactgg tccatcccca gcaggctgga   1380

tgagaaggtg gaggaagaag gggctgggga ggggggcagg tgcgggagat ggagctgaca   1440

aggagcacaa tggctgccac ccccagagag tgagtccaag gtgtgactgg tttcctccca   1500

ccccctgtgg cagaccaggg ggccggactc aggtacacag aagctgcgag tggaggtgga   1560

agaagaggag gcaggcagtg tcccgaggaa cagctaaagt tgggagaggc ccgctgagtc   1620

caggatcgag tagggaaggc tgaggtcctg gtttgaagag agagggttgc agggcggggt   1680

gagagaacat gtcagtctgt ctgtgtttga ccttcacatc ggttcatggg tggatggatg   1740

gacagaagga tgggctcatg gggttgatc gggaaggtgg agcagataga gacagccaat   1800

ggataatcgc tcaggtggta agtggcttgg cagtcgatga tcgtcacctg cagcacacct   1860

ttgtgagaaa tccatgggca tccttttctt ccagatatag gtagcctcaa accagggagc   1920

gtggcttagg gagcaggctg tcaggtggac taccaccccc actcacctcc cctcaactgg   1980

cctccctgat gtgtgacacg cctgcctaac tagagaagag agcactgggt agaggtggac   2040

acaggtgtgg ctgccctccc cagtatcact gtcccatggc gagaggtcag aaaggcaaac   2100

aaacaatggg ggtagatgct gagcagggag gggccctgaa gcaggacctg gggacagcca   2160

aggacaacta ttttgtgaga gaggaatgaa accttgcagg tcctgccaca gaagcaagaa   2220

gcagaggaaa ggccatggag agacttaata aagggtttta caaggga                 2267


<210> SEQ ID NO 3
<211> LENGTH: 1131
<212> TYPE: DNA
<213> ORGANISM: Mus Musculus

<400> SEQUENCE: 3

atggcgcagg agaacgccgc tttctctccc gggtcggagg agccgccacg ccgccgcggt     60

cgccagcgct acgtggagaa ggacggtcgc tgtaacgtgc agcagggcaa cgtccgcgag    120

acctaccgct acctgaccga cctgttcacc acgctggtgg acctgcagtg gcgcctcaga    180

ctgctcttct tcgtgctcgc ctacgcgctc acttggctct tcttcggtgt catctggtgg    240

ctcatcgcct acggtcgcgg cgacctggag cacctggagg acaccgcgtg gaccccgtgc    300

gtcaacaacc tcaacggctt cgtggccgcc ttcctcttct ccatcgagac ggagaccacc    360

atcggctatg ggcaccgcgt catcaccgac cagtgtcccg agggcatcgt gctgctgctg    420

ctgcaggcta tcctgggctc catggtgaac gctttcatgg tgggctgcat gttcgtcaag    480

atctcgcagc ccaacaagcg cgccgccact ctcgtcttct cctcgcacgc cgtggtgtct    540
```

-continued

```
ctgcgcgacg ggcgcctctg tctcatgttt cgcgtgggcg acctgcgatc ctcacacatc    600

gtcgaggcct ccatccgagc caagctcatc cgctcccgtc agacgctcga gggcgagttc    660

atccctttgc accagaccga cctcagcgtg ggctttgaca cgggggacga ccgcctcttt    720

ctcgtctcac ctctcgtcat cagccacgaa atcgatgccg ccagcccctt ctgggaggca    780

tcgcgccgcg ccctcgagag ggacgacttc gagatcgtag tcattctcga gggcatggtg    840

gaggccacgg gaatgacgtg ccaagctcga agctcgtacc tggtggatga agtgttgtgg    900

ggacaccggt tcacatccgt gctcaccctg gaggatggtt tctatgaggt ggactacgcc    960

agcttccacg aaacctttga ggtgcccaca ccctcgtgca gtgctcggga actggcagaa   1020

gccgcggccc gccttgatgc ccatctctac tggtccatcc ccagcaggct ggatgagaag   1080

gtggaggaag aaggggctgg ggaggggggc aggtgcggga gatggagctg a            1131
```

```
<210> SEQ ID NO 4
<211> LENGTH: 27684
<212> TYPE: DNA
<213> ORGANISM: Homo Sapiens

<400> SEQUENCE: 4

ggagtaggag aaagctatgg cattttagga aaattaatcg ggaggtgaca aaatagtttg     60

aaccaagtgg atatagtagg caagtagacg atagaaaata attgcaataa tataagcatg    120

aagagatgac agcccaaatc agcgtggcaa tggtgaaaag tggaacacag aaaatgaatt    180

ggagtacaga aaaatcaaaa gaaaatgaaa aaagtttgaa gccaacttga catgttgagc    240

aaaagaggga agcttcagag atcatactag agtctcaagt caggtgatca gaactgcgag    300

gtcattcacg ggcatagggg agcctggggg ggatcacacc tggtgaggag actgaggtgg    360

gggaagagga agtgatgagt tcagagctgg aagctgtgga gaggggtcag aaccagagag    420

agaaaggagg tcattgctgc cagggcagtg tgagttgaag ctatgagaac agggtagatc    480

ccaacaaaga ctgcacagag aaatgagagc ctggcacaga gagtgaggaa cacctatgtt    540

taggggatgg gaagaagaag gacccccaaa gagtgaaaga gaatccacca gacaggcagg    600

aaggagacaa agaaagtgag atgtcatgga gctaaggaag gagagactgt taaggaggag    660

gttctaacag tgccaacaag tacagagaga agaggcattg ggtttggcag tgacaaagtc    720

tctagtgaca tttgagagca atttcagaag agtgagcaag gtgggaacca gattacaagt    780

taccactaga aagtgagaaa ctgtcagcaa gtataggtta cacttttgag aactctactc    840

atagagagga gagaaataga aaccagacaa tgtactagaa acaggccagg ccaggtggct    900

catgcctgta atcccagcac tttgggaggc caaggtgggt ggatcacctg aggtcaggag    960

tttgagacca gcctggccaa catggcaaaa acccatctct actaaaaata caaaaattag   1020

ccgggcctgg tggcacgcgc ctgtaatccc agctacttgg gagactgagg catgtgaatc   1080

gcttgaacct gggaggcaga ggttgcagtg agccgagatc acgccactgc actccagcct   1140

gggggacaga gctagactct gtctccaaaa acaaaacaaa acaaaacaca aaataaaaag   1200

aaaaagaaac agtcttccag tttttcttct tcacactccg aatgccctct cttcctaagt   1260

caatatggat gaggggctgt ggtgaggtgg tctgagggcc agcctgcaag actggtataa   1320

gacctttaag tttcaaaaaa taggacatcc aaaagatcct taagggggcc acagtcttga   1380

cattcacaga cagagaggac ttaggcaggg gtgtccaatt ttttggtttc cctgggccac   1440

attggaagaa gaagaattgt cttgggccac acataaaata cactaacact aacagtagct   1500

gatgagcttt aaaaaaaaaa aatcacaaaa aaaaccctca tgatgtttta agaaagttta   1560
```

-continued

```
caaatttgtg ttgggcctca ttcaaagctg tcctgggctg catgcagccc acaggcggtg   1620
ggttggacaa gcttagcttg gaggctctgg tggaactcca aaataaacat gaagaacacc   1680
acagaagaga aagcaaaggg actgtaatga tttatggatc attaacagac atttattgtg   1740
cacttattat ttttccaaaa atgttatcca tccatttagc ttcaactacc acccatgtgt   1800
caatatgtcc agcccacccg gatatccatt tcaaactcaa catatttaaa gtcgaacatg   1860
tcaccttgct cacaagagtg ctcctctcca tttattctct accatggtag atacactatc   1920
atcacccaac cagaaacatg gcagccatcc tagattcttc aatcttcctc acctcatctc   1980
ccttattgaa tcaatgcatc tgtattctaa atagcctcaa tattgtcccc ttcctctcta   2040
ttccactatc attgctgtag tctaggacac cattacctct caccaggtaa taatagtttg   2100
gatctttgat cctgctcaaa tttcatgctg gattttaatg ccaatgctgg acatgggcct   2160
ggtgggaggt gttttgatca tgggggcagg tccctcagcg gcttggtgct atcttcatga   2220
tagtgagttc ttgtgagatc tgggtgttta aaagtatatg gcaacatccc ccatcatcaa   2280
ctctctcttg ctcctgcttt tgccatgtga tgtgcctgct cctgctttgc cttccaccac   2340
gagtaaaagc ttcctgaggt ctcctgagaa gctgagcaga tgtcagcacc atgcttcctg   2400
taaatcctgc agaactgtgt gccaattaaa cctttttttct ttataaatta cccactctct   2460
gggttttttt ttttttaatt tttaatcttt tttttttttt tgagacaggg tttcactctg   2520
tcccctaagc tggagtgcag tggtgtgatc acagctcact tgtacccctg aactcctgtg   2580
ctgaagtagt cttcctgcct caacctcaaa cgtagctgga actacaggtg ttcaccatta   2640
cacccagcta tttttttttt tttttaactt tcagtagaga cgaagaatcg ctatgtagat   2700
caggatggtc ttgaacttgt gagctcaagc agtcctccca cctcagcctc ccaaaatgct   2760
ggattacagg cttgagccac catggcctat ctcaggtatt tcattatagc aatgcaagaa   2820
tggcctaata caccagggct actgcagcag ccttctaact actctccctg cctccagtct   2880
tcctccactc taataattct ttggattatg aatttcttta tttgaaagta attaagcacc   2940
agtaaagtac atctctctga aacacacatc tgaccgtacc acttccaagt tttaaaacct   3000
tcagtaactg ccaactatct ataagtaaag tccgagttcc tttccctgga agagaaggcc   3060
tattataacc tggacctggt gccattccag ccttatcttc ttccactgcc cctatacacc   3120
caaagctaca gctacttctt ttaacactca aggttcagcc ttatgttctc tttctgtgtc   3180
ttgcccccttg agcctttgtc atttacatag ctccaacgat tgtccctgag tgatgcccaa   3240
atctctatct tcaatcctac actctctttg gagctccata tttctagttg cttgcagggg   3300
atttccatct tgacttgaca ggccccaaac tgaactcagt accttcctcc ccaaaggtgg   3360
aagtgctcgt gacttcctta gttctgtgtt actcctggtc aattagaata aaaaactaca   3420
agtgaccttt actcttcacc gttgccttgg gcccattcct ggacatgtca aataagccaa   3480
caaatgctgt caagtctccc tttctttcat ctgtttgcaa tgtgcttttt cattcctatg   3540
accactatca gaatcagaaa gatcaggacc tgacccatcc ttcacctttc tctccagtct   3600
caaaggaaga ggcaacctgt tttcatcatg tcggtccctg tgcccttgtt ttaaaacccc   3660
aaacagttgc ctcgtgctta caggtcacag tgaaggaggt cttcaccaca gaagacctag   3720
aaaaaaaaaa aagaagataa aaaacgtgac aggccctcag actgaactcg gcatctttct   3780
ctctgaggct ggaagtgctc atgacttcct taattctatg ttacttctgg tcaatcagac   3840
taaaaaacta caagtgatct acagaagtgt cctctactaa caatcagagt gaggatagag   3900
tcgggtggga ctgggcagtt agaaagactt tataagtcct tgaacagcag ggtgggagc    3960
```

-continued

```
ttgtggaaaa gtacacaggt agcttcaaca gcactgtaat gttctgaatt taaaagagtg   4020
acttaaattg agtttttgtt cttaaattat gctttataac atatagacat atgtccacca   4080
tctatattct tttgtacata tcaaatgtca ggttttcatt tttaaatttg tttgcaaaag   4140
agaagtccta ggacagtctc taggagccca gtagggaatc agtaataagg ggcataggac   4200
actaatattt gtgagtgttt actacatcag atagatcaga agatggggaa actgaagttc   4260
tgaggagtta agtggtttgc ctatggtaac atagctggaa agtgttttga gatttgaatc   4320
cacatatatt tgaccccaaa gcttgtctca gaataatgcc agagggaatt tgcacgtttt   4380
aaacacaatc ttgccaacca gaggctatga cccctgagta catgttggta tgaaaaattc   4440
cccagaatta caacatccaa tgtccaccat gaaacatgac agaggaaact tctctttttg   4500
aagacccctc tctcttcttt cagtttccca acttgcgtct tccttattct cctccatttc   4560
tcctttcaga ctcactgctt ccagctttgg cctcatctct acttttactt catttgtaat   4620
ggggcagagg ctacctcaga gcagaggagg aggagagttg gggcgtgtca cctgttttag   4680
aaagaatcca caagtgggca gcagtctgag gggcttgcgc tgggcaaagc agatgtggac   4740
agagggaatc aggaaagctt tgggttggga ggcatgatag agactcagaa tagtcagtat   4800
ttaacaagtc aggggaagtg gctagaaaga acagagacac tggcatggct caccacagga   4860
ttcaggattc caagtggcgt tttggtgctc acatcccaca gtgcggaaca aattccatta   4920
gtagtggagc atctcatagc tgaatgactc aggccgcaga ggagaaatcc aagagaagga   4980
ctgagctaca ttcccctagt cactaacgaa tcattatgta agtagatcac cccctttaaa   5040
taaatgcaat atacacaaac ccacatttat aagacataat ttagggaata cttagttacc   5100
tactaaagaa ttctttcctt taaaaaagaa aaacatggcc aggcacggtg gctcatgcct   5160
gtaatcccag cactttggga agccaaggtg ggtggatcac ctaaggtcag gagttcaaga   5220
ccagcctggc caacatggtg aaaccccatc tctactgaaa atacaaaaaa aaaaaaaaaa   5280
ttagccaggc atagtggtgt gtgcctgtaa tctcagctac tcaggagggc gaggcaagag   5340
aatcacttga atccgggcgg tgggggttgc agtgagcgga gatcgcgcca ctgcactcca   5400
gcctgggcaa cagagcggaa ctctgtctca aaaaggaata aaaaaaaagg aaaaaagaaa   5460
aaaacaaatt tctctaacta gggacttcta gtacctttcc agttgggtcc aattgataga   5520
aattccatta acatccaatg cactgtgata ggagggaggc aactgggaat aaagaaacac   5580
gaggaatctc gagtcgggtg gcctgagtct tagtcctgac tatgttcttg ggacctattc   5640
ctacctgtaa agtaagggct aatcctgtac cacctctaac cgtcatataa cttttaaatc   5700
ttagcctatc tctacccagt cctataaagc aagatagaac tctgtgtgaa ggcttctgat   5760
cctcctgctc tgctgaaagt agccagaaag gcagcaagct cctcagcctc aggaacccag   5820
cctgaggcga ggggctggct gaaattgcct ccgtctggcc tggagctgtg ctctgcttct   5880
ccccatttca ctctaatctt cagcttcagt catttgccac atctactcct tcaaccatat   5940
ctttcctctg ctctgagttt tctagagccc catccccctt gaatttatac aaatttttgc   6000
aatcaaccag attggcctcc ctgctccact aaactcatat cctcaactgt ctgctgtctt   6060
ccccatcatg cttcctcttc cacttgccag attttgcaca agatgtctca tgatcttgtc   6120
cagggaagcc tccccagttt ggctgatctc agggctgcca caaaggcacc tgctgatggg   6180
gcaagttgag gactgaactg cattcagctt gccaattcct gcacccagct cagagctgtg   6240
tctgctggag gaagggaacc ttttattttc tcccaaaagt atcacctgtt ccctgttctc   6300
caagtgacag gccacagtag gctcttttta agctcttttc ctattttgca ccacggttcc   6360
```

-continued

```
cttttttttt tttttttttt tttttttttt tttatgagac aaggtctcac tctgttgtcc   6420
aggctggagt gcagtggcgc aatcacggct cactgcagcc ttgagctccc aggctcaggt   6480
gatcctccca cctcaacctc caaggtggct gggaccacat gcacatacca ctacacccat   6540
ctaattttgt attttttgta gagacagggt ttcgccatgt tgcccaggct ggtctccatc   6600
tcctgggttc aagcgatccg tgcacctcag cctcccaaag tgctgggatt ataggttcga   6660
gccaccgtgc caagccaaaa gctagaatct tgtctatgct tttgtgtcct ggtgcctggg   6720
aaaacttttt ttctcctgcc tcagttcagc tcagtgataa ataaggaact gaggttagat   6780
aacaggtaaa gtctaggacc tgcaggatga gtgaatcagg tgagggagtg gtagtcttct   6840
tccttgtcag ccaggctagg ttcaggggca cctggactga ggcgaggggc tggctgaaat   6900
tgccttgtgg agggccctgc cagtgatgcc ccctccagca aatagggcca gctctatgca   6960
aatgtgttct tgcccaggag tttggtttct tctctctgag ctcctggcac agtggaacca   7020
atgtgagcag ctgcttggca ggacagagaa gggcaggcta gcagtcccaa agctcgggtg   7080
acaggaccag gcccaggaga cggggatgtt gactggggct ttaacagcac tcttgatgcc   7140
aatctcgggc tgaaaactcg atatttccac ttggaacaac aagaatcacc agcaagagag   7200
ctgaggagag ggcagtatac cgggggcgcc ccctgcaggc ctcacagggt ggtgccagaa   7260
cagaggaagg tggcacaggc agggtggggc tttcaggaca tccctgagat gatggtgatg   7320
acggtgacaa tgatgatgac catgaagaag acaatgagga ggaggaagag gaagacagta   7380
gctagcattt actgagtact aacaatgtgt caggcattgc cttatgtagt cttcatgaca   7440
accctctaag agatgaataa tatggttttc tttttttag atgaagaatc tgaggtttaa   7500
cgggttaaat aattgctcag gttcacccag ctagtagtgg acagaggtgg gatttgaacc   7560
caagtcattg cctcctgagc ttatattatc cagtaccgaa tttcccacct tgccaggtca   7620
ttccaggagc ttctagccct ccgtgtccat ctctatgtct tcctgctcct ctagctcata   7680
ttttcttgat ccaaatttaa aggatctgga taagaataga tccatatctg ggatataata   7740
atactgataa caacagcaac aacactttgc gtttgtaaac cactttcttc tcttcattat   7800
ttccctgggg aaaaataaac aataagatat ttctgtttct ccaaattttg ttctgatttt   7860
tatcagtgtt cctgaagcta tttcaatata gtcatgatca atttctaaga atatttttag   7920
gttctgcttt tttatgtaac agtgtgttat atacacattc acatatttaa acacagcaat   7980
tattatggct ttacagtaac ccatgatatt aatattccac agatattaca ttactgaggc   8040
acactaggct aaggctgaca acaccaaatg ctggcaggaa tgtggagcaa caggaacagg   8100
aattcgtggc tgatgggaat gcaaaatggt acagctactt tggaagaaag tgtggcagtt   8160
tcctaaaaaa ctaaacatac tcttaccata cgatccagga atcatgctcc ttggtatcta   8220
cccaaaggag atgaaaactt acgtccacat gaaaatctgc cgatggatgt ttatagcagc   8280
tgtattcatc atggccaaat cttgaaagca accgagatgt ccttcagtag gtaaatagat   8340
aaataaacca tggccatcct gaaatggaat attattcagt gccaaaaaga aatgaactac   8400
aaagccatga aaagacatgg aggaacctta aatttacatt actaagtgaa agaagccaat   8460
ttgaaatggc tacatattgt acaattccaa cgacatgaca ttctggaaaa ggaaaattat   8520
ggaaacagga aaaagagcag ttgttgccag gggttaggga agggggattg actaggcaga   8580
gcatagagga cttttacagc aatgagacta taatggtgga tacacatcat tatatatttg   8640
tccaaaccca cagagtgtac aacaccaaaa gtgaacccta atgtcagcta tggactttgg   8700
gcgattatga tgtcaatgta gcttcatcac ttgtaacaaa tgtgccattc tggtggatgt   8760
```

-continued

```
gtggggacag ggggcatacg gaaaatctct ataactttcc tctcagtttt gctctgaatc   8820
taaaactacc ctttaagaag tcttctttta aaacaattta caaagcatga ggtgatacag   8880
atgtgggagt ttggctcctg tctctgccca actctgtgac attcgataaa ttacttaaca   8940
tgtctctgtt tcagtttcct catctataac tgggaaaaat aacacctgtc ttatagagtt   9000
gccatgggga tgacatgagg catgtgtctc gttcatatcc catgctcagt gaattagtag   9060
cagcagccac tgtgtgtttg tgtgtcttta tccctcctgg gttaatgagc tccttgtggg   9120
cagggactca cccattctgt aaccacccca tctaacacac tgcctggcac ttgggctccg   9180
cagaagtttg ccgagtgaat acttagtaag ccctaaccta ggcttttctc tctggtggac   9240
atttgggttg tttctagggt ttttgctatg aataaaacac atttcaaagc cctttgtggt   9300
ttttttggtt tttgtttgtt tgttttttct tcgtttgatc tgctgactct gtgaagcagg   9360
cagaaagggg atatttgctc ttgtccacac cctggtacag atggaataac tgtggctcag   9420
ggaagtgaag tgactcctat gggacacagt gcaaatcagt ggcaataatt agaacccctg   9480
accctgcctc ccttccttta gtagatctat tttccttcta gctaccgcct tctggatcca   9540
tggcctctcc aaaactagac catgatggtc agcctgacct gagagcagca cctgcacgca   9600
gagacccatg ttgaaggtgg tgagctgcca gctaccagat ggccctctga aaccccaggg   9660
aacctagcac cttattctca aatacatgag ggcttgtatt ttcccccagg aaggagcttc   9720
ttaggaaaga gccagcgtgc cagctttgtt tttctttctt cttctttttt tttttttcct   9780
atgagggggt gaggagccaa gctctgagtt gtccaggagg agggactttg gctaaaaata   9840
gctatggcgt gtggtttgga tcaaccccta gtggtaccca ggactgggga ggggaggggg   9900
atgctctgga gctgtcgcca gactggttgc cgtggaaaca agagaggagc aggggagcct   9960
gggaagtagg gatgacacag atagcaagtc ctagtcagag ctgccgctac atttaggaga  10020
aacagcggtg tctgcggctc ccacccttcg gggggcccgt ggggggggcg gtgtcagggg  10080
catggacgcc aaccccccagg ggtctctgct gccggctact ctcctctcca cgtgctgtga  10140
gttgagttgc gggggacttg gggtttgggc ccctatttcc aaggcaagtg ggggtttggg  10200
aggagctggt tcttggggga gttttcacca ggtctctcct tccaaaaaat gagccccctt  10260
actccccagc tctctagagg gaggaagagg ggcccaggaa aagtggtatt gcaatcttct  10320
gcaaaggggt catagcatgc acaagaaatg aggagtaggt tggaggaact gaaattcttg  10380
gagggaagat ggagaaatca agtccttgat cttgagatag aggtaacaat ttcacacttt  10440
tccttcccct gagaaaagtg cagtccccca ctcaggaaga caggatgtgg gacacattca  10500
aaataaggtt tacctagatc cctggggcaa tggagagtga gagagttctg ggggtgatcc  10560
gacatcgggg ttccttcccc atccctgggc agagagatct gtctaggcaa gccgactggg  10620
ggtcagatta cctaagaccc tgagagaaca tctggaagcc cacctgggac taaagctagg  10680
ataatgggag cagggtcgtt ttctgcatga cctggggtct ctgagccagt caatgcttac  10740
tcttcctgag gacatctgag cttcaggaaa ggaaaaggaa gcccattgtt gggggcaggg  10800
gaaaccctaa tcttccattg ccatggggct cttggaccct gtgtcccctg actccatgga  10860
caataaatgc agggggtgcc cctaagctca aagccatttc attttgattt ctcttcctac  10920
cttctctacc ccaagacaca caaacacaca cacacacacc ctctccagag tgctgactgc  10980
agaggacctc accccagaac ataagatgct ggagtgctag gtttagagtc acatacccag  11040
gcagtttctc cccaggacct ggtcaaccat ccaggccatc tgtggttcct atggcacact  11100
cctccatccc ccacccacta gccagcccac gtttccgtgg agtgggagga gaggatcatt  11160
```

-continued

```
cccaggaaag agaagggaag gtggaagagt cccaaatcct attctaaacc tttccctgta  11220
tggtccatat ctcctagagg accctgggtg ctttggggaa gggctctgga cctctctcag  11280
agcagattgc agctcagaga gctcctcaga ggcaagcatg tgaagaaaaa tcaggtgggc  11340
ttcgcttgga atgtgggctt tggggcatat ggcaggtggg ggcggggctg gtgttaggat  11400
agtccatggg aagtaagagg ctgggggaaa atataactag agggagtggg gaaataaatg  11460
tgggtgctta gtgcttcacc tgatctgatt ccatgtctct catgaagaat aggatcccag  11520
agggatacga gcctaactct ttataactct gggcttcctt tcccaggctt ctgtgttggg  11580
atcttccagt tcccctcccc atttgcaggc tgtctccact aggagaaaaa acccaaggga  11640
aatgaggctg gcccaagagc agcagtgatc gtgggtaggt ctcagggagg atttctagtg  11700
ggaatttcct aatgttccac ccttgtgcac tggagggttt ccactgactt tccacagctt  11760
tcatttcttt ctcgtttgta agcatgttga ggggagggaa tggagcggag tgagtgaggt  11820
ccaaggaggg aagaatgaga aagactgtgt atcagtcttg gggtgaactt caaaacagcc  11880
tgcgaggaga gccattggtg gctgcactgg ctacagctgg ggaagggatg gtggaagtcc  11940
ttagggcagg gagggctcca ttacccgcct gccccccctcc ccaaaaagcc cccagtctat  12000
tgatttcagg aaatcactag gggatctgg gcctgggtct ttggccccgg ggctgcccct  12060
gaggtgctgc acaccccagc tggaggtgat ggcaccaaaa tatctggtac ctccttcccc  12120
tgaaaatcat cgtggaactt gcacagttct atccagttca ggtacatcat tccatttgac  12180
cctcacaact ttctgagcct ggggggcagt tagggctgaa tgtgttattc ccagaaatag  12240
aggccaggca acacgaaggg actcgcccag ggccccccag ggctcggtgc tggccctgat  12300
gccccgtgcc tccccatctc ccgaggggcc actcattcgg caaacccttta ttaagcccct  12360
ccaggacccc cgacgccgcc taggcgccca gcgacgcgcg gcaggtggca gcagctcggg  12420
cccccgccgc actccaggcg cccgcagcgc tcgccctgac gcggccgcca tggcgcagga  12480
gaacgcggcc ttctcgcccg ggcaggagga gccgccgcgg cgccgcggcc gccagcgcta  12540
cgtggagaag gatggccggt gcaacgtgca gcagggcaac gtgcgcgaga catacccgcta  12600
cctgacggac ctgttcacca cgctggtgga cctgcagtgg cgcctcagcc tgttgttctt  12660
cgtcctggcc tacgcgctca cctggctctt cttcggcgcc atctggtggc tgatcgccta  12720
cggccgcggc gacctggagc acctggagga caccgcgtgg acgccgtgcg tcaacaacct  12780
caacggcttc gtggccgcct tcctcttctc catcgagacc gagaccacca tcggctacgg  12840
gcaccgcgtc atcaccgacc agtgccccga gggcatcgtg ctgctgctgc tgcaggccat  12900
cctgggctcc atggtgaacg ccttcatggt gggctgcatg ttcgtcaaga tctcgcagcc  12960
caacaagcgc gcagccacgc tcgtcttctc ctcgcacgcc gtggtgtcgc tgcgcgacgg  13020
gcgcctctgc ctcatgttcc gcgtgggcga cttgcgctcc tcacacatag tggaggcctc  13080
catccgcgcc aagctcatcc gctcgcgcca gacgctggag ggcgagttca tcccgctgca  13140
ccagaccgac ctcagcgtgg gcttcgacac gggagacgac cgcctcttcc tcgtctcgcc  13200
gctggttatc agccacgaga tcgacgccgc cagcccccttc tgggaggcgt cgcgccgtgc  13260
cctcgagagg gacgacttcg agatcgtcgt tatcctcgag ggcatggtgg aagccacggg  13320
tgcgagcagg cctggggagg ggagcggggt tggcagaggg tgggcgggac cgaggaaggc  13380
aggggcgaga ctaggggcca ggggagctgg ggaggatgga tggaggggct ggtggaggat  13440
gagacagtga ggtgagacag gggtcggagg cgggagtgga accgagcaac gccgcagaag  13500
gccaagagaa agcttggagg aattctccga aatggcactg gcgtggggcc ctgggcccag  13560
```

-continued

```
aggaatgtgt cacttggaat agggacagta ataatagcta gtgctcgccc agtattcacc  13620
ctgtgtcatg cgcagttcca aagcactttc tacctctgag tcgatttaat cctaacaaga  13680
accctctgaa ggtaacttct tgttattgtg ctcacttttt agagatgaga ttgctccaat  13740
gagaaattaa ggaagttgtc cactttccta agccaataag tggccatgcc tggattggac  13800
acaggcaatg tggcttcaat gtttagtggt cccgagttgg aaggaggggt taggttcagg  13860
ggttttctca ctgcagtcag gttcaggccc ctggaatttg acggtgaagg ttttccattg  13920
cctgagttat ttctaggccg gatcttgagg ggagtttaat acctagtctc acttgtacct  13980
cggtttccca attcatccat ttccactgac aagggatata gatgatgtta ccttttctag  14040
ctcttttcca aaaggaactg gcaactcatc tgtgatgtca ataagtccaa cccagaccta  14100
cacagtgaag gctttgggag caggtgaaaa aagaccagtg ttacaggagt cgcaaaggag  14160
gtcacttagg acttgagatc tagaggatag atgaggatga ggaaactgcg ggtggaggac  14220
caaaggccca ctagggggcg ccgcagtccc tcctctgacg ccagagctgc tgatgctccc  14280
tgccggcttc gctgacaagc tggtgccttc agatcctttc cctggcccct ttaggctgag  14340
actccgcttc acaccccaac cccagctccg catcactgtt cccattcctg cttcaccccg  14400
actctttcct cttcccccac tcaccccgtt ccctttcctc tctctccagc tgtcactcct  14460
tttctgccag tatctcaggc aggcccctca ccctccaggg aagttgctgc ccggccctct  14520
tttctctttg tacccccagc cctgccctct cctcctcgaa gcccttctct ccccagtgtc  14580
ccttatgcct ctttctcttc tctcccactg gatactttct attccaactt caccgaggaa  14640
taccaatgtc tcagcgccag gctttccgag ttgacagcca ctctccggtt agctaatgtt  14700
cactcttctg tttccccttg ttccgagatg gatatgggtt gggggcaaga ccctgtggca  14760
gaaaggagaa tgacctgccc tgaggggtgc accagcccaa caggaagata ggacacaagc  14820
cccgggcagg gaggaccagg acagaggaga tgaggatagg aatctgtctg tttttctaga  14880
gagataaagc tggaaaggat ggtaatattt tgggtgagac agtcaggatt caaaacgctt  14940
ttgaaaagca agaataatga gccaaaaccc agcaagatga catttaaaat gaataaatat  15000
aaaattctac atttaggctt taaaaaaatc acttatgtaa gcacagcatg gaagagcact  15060
ggtgaaaaaa gaactgggag ttttagttgg ctacagtctt gatgtcgtag caatgtgatg  15120
cagcctccaa aatgattatg taatgttatc ctgggcccta ttagtgaaag catcatggcc  15180
agaagagaga gatggtgcgc gctctcttat gcacggagca ggccacagtt ggaaaattta  15240
ctatactcaa aatgcttaaa gggccctcct tggccattct ggcttgtaat caaaaaagta  15300
gagttctgga aaaccaggtc aaatgaggaa tcgtggagga agccagggat gttaagtcaa  15360
gagagaaaac atgagggaat ctgagactcc tgttttcaga tactcagagg actgtgaagt  15420
gggaggggaa tgaagccaag agttggaaat cccagggtac aggttttagc tctgtataaa  15480
gaacaaccca actattagag ctatcataca aaggagtggg ccctttatga agtggtgagc  15540
tatcaatcct gggaggtaat caagtataag ctagatgccc attgttagaa atgctccttt  15600
ggggagccct gtatggagtg agaagttgga ctagaggatc cctaaggtta gtttcaaggt  15660
taagcttttt ttggttggca tcaccaaatg acaggagggg aaaaaagagc tggacattaa  15720
gaggagttgg ggcaaatgga gaagacacga gggagctggg taagaacagg agctagggag  15780
ggggggaaat ggactggacc aaagggaggt gggagccctt aggaaggaat agaagggagg  15840
gtgctgggag tagggttgtg gaatgagaag aggagaggga agcctggagc tgagattccc  15900
cctgaccggt gcccctcctc ccaggaatga catgccaagc tcggagctcc tacctggtag  15960
```

-continued

```
acgaggtgct gtggggccac cgcttcacgt cagtgctgac tctggaggac ggcttctacg  16020
aagtggacta tgccagcttt cacgagactt ttgaggtgcc cacaccttcg tgcagtgctc  16080
gagagctggc agaggctgcc gcccgccttg atgcccatct ctactggtcc atccccagcc  16140
ggctggatga gaaggtggag gaggaggggg cgggggaggg ggcgggtggg gaagctgggg  16200
ctgacaagga gcagaatggc tgcctgccac ccccagagag tgagtccaag gtgtgaccag  16260
cttcctccag acccctgtgg cagaccgggg gccagacaca gatacatggg gaactgcata  16320
tcggaggtgg tggaggagga ggaggaggag gaaggcaaag cccctggaaa tgtgctaaag  16380
ttggaaagtc cccgtccccc agaacctcaa gtctagaaac cagtatggaa gggaggggtc  16440
ctgatttcag ggaaatggag ggtggggccg ggtgaaaatg ccagtctgtg tttgaccttc  16500
acatttgttc atgagtggat ggatggacag aatgatggac ttttggggt tggatgggaa  16560
gatggtagca gataaagaca gctgacagat acatagatgg accagtagac aactggtcca  16620
ctcagggctg ccactaacct gtagaacacc cctgtgcaaa ttttaaaaag gaaccctttt  16680
cctccagaca gatacagccc caaaccaggg tgcatggctt ggggagcaga gtataggatg  16740
gattgcagtc cccagtcacc tcttctgcca gcctccccac atatggcaca actgtctaat  16800
gacacggtag gccaagctga agtgaaggag aaaggagccg gaccaagatg ggcacatgag  16860
gagggtgccc tcctagctcc accctcacca ggatgaaggc gtgcaagggg ctcagcaagg  16920
tgtgaatgac cttagtccgc aagttcaggg aagcaggcag agcggggagg tgcctgagct  16980
ggggcctgga gaggggcctg ggaaaggaaa accagggata gctattttct tacagtggag  17040
tgagatctta caggtatcag gcacaggcag gaagagagag agagaggttc tggggaggaa  17100
gggccaggag agagatctag aaagtgggtt cactagagct gggaaacagg gagcccctag  17160
gaaagcagtg tgtccttggg gcacagtcat tcacatcact gattgggtgc catgtggagt  17220
ggacattcaa aaacctggtt cctgtcctca aaataagggg cacctgggaa aacagaggaa  17280
tctacctgtg gtgactgaac gagggataat tcaaactgac aacctgtgca gtcccgtgga  17340
gggtagggga gtgtgggtga tcagaaggct ggggccagtg taaggcatag ggaatatgta  17400
agtcaggagt tagaaatctc cagtgtgcgt tggaatcacc tggagggctt ggtaaaacac  17460
agatttttgg gctccactcc aagggtttct gacccaagag gtggggacca aaaccatgca  17520
ttcctaagaa gtccccaggt catgctgctg ttgctggact gaggaccaca ctttgagaac  17580
ctgtgctcta agtgaatact tggaagtcgt ttcaggacat ggggcataga aactgaggag  17640
tagctgagag gaagatgaag agaagctgag aagaagctga ggatcctcac aggagcagac  17700
agagaaatgt gaagggtggg gttttatgtg tgggaaaggg acccgaagcc caggctgaag  17760
agtttaactt tgggcccaga aactcaacca tcaatggaaa cagggcagtg acaagtggag  17820
ggggtgtctg gaagctgagc aggcccgaca gagagatgaa gccatcagaa ggacttgagg  17880
gggctcctgg ggaggtcggg gggaggtgga gcaggaagag ttttaggggc aaaggacaga  17940
acccccttgta ggactggagg caagattgaa tgtgggagaa aatcggagag aagcgatagg  18000
agttagaaca tctggatgtg tctgcagcct gctgtcagcc caattgggcc agggggtccc  18060
aaagacgcat attctcaccc cacctccacc tgcttcctga tcacatccca gtcaccagcg  18120
gcagcttcct ggatagtgag ggagaacaac tgcaagttga gagaggcaga ggggtggaag  18180
ggacctgaag ctggcctgga gaaaagcata ggcccaggag agcctgccct gggacagcgc  18240
ctgtctccca cacagcagca ctggcccagc aaggacctcc tcccttggcc ctggccacat  18300
cccactcctg ccctttcata agcccctgg ggaaagcact ccagtcttct ctgttccagg  18360
```

-continued

```
ctgggcagat agggtcctat ggggcacagc cagggtccta tgggcatagc cagggcccta  18420
tgggtcctct ggaagcaaga aagggggcca tggaagcagc ccagacagct ggggttcact  18480
cagagaggac ccaagtccca gtcccttcct ttcagtcaaa acacggatat ctttgcctca  18540
ggtcacaggg ccactggggc cctgtcatca aagatgagat tcctgaagcc tggcattgac  18600
tggtccccta agaacagatg ttgggatgga gaatggggat tcatttgggt ttcagtaaaa  18660
caggggggtc tggacaagag cgggtgggct acttggtatc cacacacacg cactcacaca  18720
ggagccaacc cattgcagct gaacaagcag agaaactcag tctggaaagg cccctcctgc  18780
ctgctgaagt cactgagacc ctgccacacc tctcctcgcc actgtcacca ctcagggcac  18840
cactgtacag tgcaacaagt caggagacct aggtcctact cctgacactt gctaattagc  18900
tctatgactc tgggcaaatc gcatatctgg gcctcagttt cctcatctgt aaaaatgaca  18960
gcaaactcgt aatgctcaat aaatgtttaa ataacaactg aaggaggcct gccagatgcc  19020
tcttaaggtg ccgtgcaggt aagaatttta ggatcagaga atccttaggc aagaaaattc  19080
atgaaactcc tggggcactg gaggaggggt gaagctgaag ggtgggaggg aggagacccc  19140
agggtaggta caggcaggtg aagcgggtat atgcaggtgt agtgggtata tgcgggtaga  19200
gggtatatgc aggtacagcg agtacatgtg ggtgcaatgg ctctgtggac acacaggccc  19260
tcccctgact gcctgttgtc ccagcctgag tatcagttgt gttctgaggc ttctattctg  19320
ctgctatggg tcagaaggaa caacaatttc agccccaggg cctagtggga ggagtcaggt  19380
ccaagactag cctgaccagg agaatgagac gtgggaagag ttggggaaag tctgggaagc  19440
tcagaaaagg cactgcccct ggaggcccat gccctttaac atgggagaag ctggtgcggg  19500
ggtgaccaca ggcagctgga acctaccctc cttttctatg cttccctccc caagtaggag  19560
tccaatcagg agttgtctca gccccgacag ttcaggctgc agatggaacc caggtgtccc  19620
ctcctggggt gggtggcatg gcccatggag gccagatggt gtttgtggtg ggaagagagg  19680
cctgggtcat ccagaatagg ttgtcaatcc ccaaccacct ccctactatg caccctgagc  19740
gttttacagt ctcatggtag ggaagacaca gccaagcctg ctttttataa aacaagttta  19800
ttcacatttt agaaaaacta attccaggac aggaaatggc ctccctatag gatccctaag  19860
agatcaagaa cagaaggcca gagggagggg cttgggaggg aaggagtggg gaaggggagg  19920
cacgtctccc attctgggta gtgggaggtc aaataaatta aaggaagagt ggacagaggg  19980
agagggtgtc caggcaacca gaggagggct tggagctggg ccggaagaca gtcgacacct  20040
gcaagacctg aaaagggtgc ccggtgtggg ctaaggacag agagccctga gtggggctcc  20100
ctcgcggcct ccacccctta acagggccct gtggatctga gctgcctact cctcctccag  20160
gtggggcctg ggagggagca gcttggttca ggacttgggg gtgggaagcc caatgaaaac  20220
aaggttgggg ggttcttttc cctcacctgg ggagtaaggg atcaccgttt tcgaagcctc  20280
ttcatgaagc agcaagtgat ggtaccaagg acagtggcac cagtgactag ggccacccct  20340
gtacccacca gcagaggcac aaatagggtg tccagggctg ggggagagag gatgactgtt  20400
cagagaggat gccatcatcc tccacccata cacttgcctc tgcgctttcc ccatcaagtt  20460
ctctgaaccc accttctcca ttcacagaca cccccatccc tgcccacagc ctgccccctc  20520
agcatgcaag tcagcatcaa ccacagagga ccccgtgcag gtgggcactg cagggctgga  20580
agttggattt tttgagactt catgtgacat aatgtggagg agagagatag tagcaggagg  20640
gtcagaagat gggaagggaa ggccagtggc agaggccagg aggaaggcag agtgaggagg  20700
gtggaggggg tgtcactcac catgcatgta ggggtagact gtaacaggcc ctgagcgggc  20760
```

-continued

```
actgcccgcc tggtaccagc tgtagtcggc atgctgcacc caggcgctgg gggcacagtg  20820
gtacacgcct tcatcctcgg gccccaagct gtgtagtctc agccgatggc ttcggggccc  20880
caccagctct acgctgacag ggcctcctcc aggccggact cccagctctg ccacaccatc  20940
ctggcctacg ccacccacca gctgggcagg gacagagctg agctctccgt cctctggtcg  21000
ctccacccac cagctggcgg ccagccgcag tcctgggggg ccaccccgca cagagatgtt  21060
gcacagcagg gaggcagtct ccccgcggta cactgtgcct cctgctagcc atgccacagc  21120
ctccagcacc acacctgcag aacaaaggac atggggtcag agggtgcagg gccagggagc  21180
atggggttag ggctgccgcc aagcaccgcc ccaggaaact cagggtattc ccacaatctt  21240
ggtagaagag gagcgtgagg ctgtggcctg caaacagctg acggagaggg aggggtcatg  21300
gaaacagaag gaaaaggggt tgacaatcct cgaaccccgt ccagggccca gccccctctc  21360
accttcctcc cgcacatgta cagggagagg ccgggaacgg gcactggctg cttcacgaag  21420
ccgggtccca gaccctcgaa cataggcttt ggcgaggcag cggtaggtgc ccgcatcacc  21480
aggcctggca gcctctagcc gtagccggta tgttctggat gccaccttct ccatggcaat  21540
gtgtcggccc tcatagccag ggcccaggct gcccacaccc tctgtgtcca gctgggctac  21600
caggcggccg ggccccaggt gcccccgcag gtgccatctc ccaacctaca gagtatgcag  21660
catgacggcc tgctggggga agtgcccctg acacattgca cagcagttcc aagggctccc  21720
ctgggccgat ccgacgttca ccaggcccca ctgtcactgc cagctggctg gctgaaacac  21780
aggtagggga agaggtgtca tggaggcagg aggggacaca gaggcacccg attccccaac  21840
ttcctgtttc ctacttgaca gcagcaactt caaaacctcc tgtctccccc tcactaggta  21900
tgaccatctt tctatttagg ggcttgaatc tcacccctca gcatgggcct cctatctcta  21960
tacccaattt ctgagcagag aaaacccatc aagggccggg ggagagaaat gctagcaagg  22020
ctgctcactc tgtggaagat gagttccttg gagtcagatg atggctatct ggtacccccct  22080
gtggccacag tgcccaccag gatactgtcc ctcccagctc ccacagtggg atgtataagt  22140
ggcacttaca cagcgtctgc acatccacgt gggccaggac ggccctttttc tctgcaatct  22200
gggcccagct gccatcagga tcctgaatcc actcagcggc agtgcagtgg taggtgcctg  22260
cgtcccctgc ctgggcaccc cctactacca tgcggtaccg atcggtccct tccttgccca  22320
gacgaagctc ccctgcagcc aatcgctcag catagggagc tccagcctcc acggccaagt  22380
ctgaccggat tcccaccact tcctgcagag ttgaccgccc aactggtgcc tcgggcacag  22440
atcgcccaaa ggacactgcc aggtgtgtgt gcttctgtgt gcttgtcctc gccaggcagc  22500
ccagtgccag ctcctgcccc tcatgcaccg tcatgcgtgg gggtgaggtt ggggcctggc  22560
ggcctcgggg ccctgggggg gcagcagaca cctggaggac atctggaaga actggagaga  22620
acagctggag tgagggaggg ctgggagctg gcagcccttg ttactgtttc ctgtgtatag  22680
cctatctccc taaataaact gtgagctccc agagggcaaa gatcgcatgt tgtattattt  22740
cttctgtaac tcagtggtgc caagggcagt actgggcaca gcacaggcgc tcaataaata  22800
cttgtagaat ttcatagaac cagcccatcg cctactcacc cttatgtttg agactgacct  22860
ctgtttgaaa tactgagaaa agcggctctt tcttctcaga agacaaagaa acttaagaga  22920
gtgagaatgt cacatggtct aactccttcc ctaactctac tctctttccc agatctgggt  22980
cctgtactgt ccaggagtag aggctattca acccaacagt cttcttcgtt cttgggaatg  23040
gaaagtggac tggacaactt aaggacattt cttctcccag gaggggtctt aatatgataa  23100
gatgagcact ggcctgggtg aggaactctg ggtttgagtc ccacatcagc cactgagtta  23160
```

-continued

```
ttgggtgact ttgtgcaaat cacttaacct ctttgggcct caagttcctt ggctacaaaa  23220
cctaaggggc aactagatag gtcacttgtg gccttgactt tctgccttga gagggtgtgt  23280
ggctccaccc cgtcccaggg cccagtacct ctcagctcca ccttgccgct gtagctgccc  23340
aggtagcggg tatcagtgga gggggtgtgg cactcataaa tgccggcatc ctgggcctgc  23400
aggcgggcaa tcttgagcac cacggcatca ccttgtaggc gctgcacctg cacctcaccc  23460
gccaccactc gggacttgaa gacagcatag gagaactggg tatccttggt actgacaatg  23520
cccagtgcag tatctggggc ctcgggccta tacaggaacc actcgaagtt ctgctgggca  23580
gggccctcat agccggtcac attgcaggag atggagacag ctgtgccagc cacgcggtac  23640
aagggcccct cggggaccag cacctcccgg gcccagcatc ccattcctgt agggaaaggc  23700
agaaggagtt ggagatgcct ggttcctcat tccatgccct ctgccgccac aagcaccatt  23760
cttgatctct gcctacaaaa ggaaaggaga cctgggaaag cttgtccaca gcttggaccc  23820
tgttctgaga ataggaaagg gatgctgtga tataagacac ctggatctca aggaggtggc  23880
atgggcccag gattgccttg gcatccagat gcatcccatt tctggcggac tagaagcaga  23940
gcacctgaag gcagaaagga gtacatctga ttcctgacct aaccaggcct tggttccaac  24000
tgaaccttga tctgtccctg ccactcaccc acctccatgt ctgccattcc ttcctcagca  24060
cctggcaagg ggagccttct ggctagggga ctctgagact acatgtccct ctcctttgct  24120
tgaggggagc tggcagtctt gctcagaagt gctagttggc tcagctgtgt cacctgggcg  24180
agacaatgga gccagtgacc ctagctggaa agggcacagg cccagtcagt tctcaccaca  24240
caatgccctc ccctctccag ctgcgccatg agctcactgc ttctctcacc ccacagggct  24300
gcccaggcag ctggggcttc tggggcaaga tccaggctct gccctggcca ttgggggcag  24360
aagatcccct cctccagtgc ctgccaacct tccgggctag cccagcagat acagaaggtg  24420
cctgccccag ttccttaaca aaagccttca tttgcacatg gtatgcattc atttacatat  24480
atggctctct ttctgtaggg aggcactaaa tccccagctg ccccttctca tctctctccc  24540
ttcagaaagg ccaaacctct cttcttcacc ctactccacc cctatgccca accctacccc  24600
agcagatact cctggcagac ttagagggct tagctcctcc cttctttcct tccatagctc  24660
ccactagata agatcacaga acctcaatgt aaagagggct aggccacccc tccccacctc  24720
tcccaatttt acagatgaga aaggtaaggc aggaaaagta taatatgtta gccaagatca  24780
tgctgtccct agatggcttc cacacactcc tccagagggg caaaaccaga gaggaagatg  24840
gggaaactcc aaggccaggc ctgaagggac tgacctcacc aaccagagtg tcacttttag  24900
gcctcccagg gggataccat ggactttctg caggagctag aggaaaatgc ccaggagtct  24960
gtggtcaaac tctaccctcc agcttctcta gaacggctcc tctgaacttc cccacccctg  25020
cttctgggct cctagcccct tccttcatcc tctggctggg tcacagggag aactcatggt  25080
ctgttgttaa gggcacagct gccagtcagg aagtgggatt ccagcaccat ccccatgccc  25140
agctgtgtgg cctgggatcc agtctctttc tgtcctaggc ctcagtttcc acactggagg  25200
agaactaaga gctccagctc tgaccatgtg tgagtgcgta tgtgactcag gagagccctg  25260
ccccaggcca ggcaagtttc ataatcagag tgacggtgga gacagccaag ctgacacctt  25320
ccctgactgc ctcagggcag actgctcaga aggccccctc ccattttcct ggctccacaa  25380
ctgctgatgc ttggagatgc ccatgggaaa gtcacctcca cagccttagg aaatcagttg  25440
ccacacagct ctctctcccc tcctctgtat cagtcgcagc aaggaaaggg acagcaaaga  25500
ggcctgcttt ggaatcagat ctgtgttcaa atcctagccc caacactcac taaatgtgct  25560
```

-continued

```
ctctggggca agttacttca ttttcctcat ttgtgaaatg aatgtaagtg cccacaggca  25620

gtgggtgctc agacctctgc gtgctccttt ttcaaacaca ggccagcact tccccacctc  25680

cctgggctcc tccctgctcc atgctgccca ctggggaaaa cacaccaagt gctaggcaac  25740

ccaggcccca cagcgccttc ctctctgtac atcctcctgc cacctgccca gggaccaggg  25800

agaggactca tcctaaccct gcagggccca gggacctgca gcaggggaag gctttgcttg  25860

gtgccactgt ggagctctgg tctagaaaca ggcagctggg gctaccttca gcctctgcct  25920

tgacgacagc agctctgaag tcaccatccc cacccccacg cttcactctc atttcaaggg  25980

cttcagcctc atcaacatct gtactggcag tttcactgtc tccatgccat actcttcccc  26040

agaccacctc ctacagggag ccctccagtt caggccaaaa acaattccac tgtcattatc  26100

cccatgcatc catgcaagat tggcccagaa caccccacca tgaacaccca ccacagcagg  26160

cacaaggtgc ttggagatcc caggatcagt ctccatggaa cctggtttct cctgaggcaa  26220

ggaagctgga actaagcggt gtgaaaactg atgggtggct gcagagccaa gtgccatttg  26280

ggagacagga agaagggcaa agagggaccc aacccagggt ggagatgggg gtgagagagg  26340

gaactgcccc cagttgatga agtgcgtgga gcgcaactgg gagagactta cttcaaagat  26400

cgtgggcaga actggcctct gggcctccag ccaactctgg ggcaattatg aagctgggca  26460

ggcactgccc tcgtagggcg ggcacccaag gccaggcctg gagctgagtg tggggcagaa  26520

aggagtcgca gcatttggtg cagcgacccc agtacgtggg tatgctagct gagatgtgtg  26580

gcctgccccg ggaggccgag cagtgcctgg ggcagcacct tagtgggtcc tctctacgcc  26640

ccagtccctg gcttagagct ggggagcctg cactcttccc aagactggct cggcggacag  26700

ccacaaagcg cagctggacg ccgaccccgg ggaggctgga ggtacccctg acggaggagg  26760

atgtgaggag ccccgaaatg ctaggggggt gctggatggc aggcacctgc ccggcagggc  26820

cgggaaccgg aacgggggcc tggcttacct agcattagca gcagcagcag cggcagcgaa  26880

ggcggcagca gcgtgggcct gagggcgccc atcctgcgcg gccagctctg gggaggctcc  26940

gggggatggc gcgggttctg gggggccgga agggtggggg gcgcatgccc aggttgaggg  27000

caggaagcgg ggcagcgagg cgtgggtgcg ccgagcgagc tgaactggag ctgccgaatc  27060

ccctccctcc gcccctcccg ctgctttccc tccagccctc ggcagttctg aaaccattct  27120

cgccccggcc cgccccggca ccgccccttc caccgccccg tctaggcccg ccaggactac  27180

agtcggactc caatcctggc tcctccccgg gccccggccc cgccccagtc ccaagccgca  27240

cccccttcccc gtccccgcag ggctaacgtc agcctccaat cctggctccg ccctggaccc  27300

cggcctcgcc ccgcccctgg ccctggctcc gcccgaggcc cccgcaggag tgagctaact  27360

gcacctctgc gcatcgaaat tcccacccac cctcgcacag agcgcattcc accccgcacc  27420

tgccagcctt tcctggagag ttgggtgcag ggtccctggg attggcgagg tgactgtgac  27480

cacgcattta gaattcagtt atttgctctg agccatagtc ctcgctgcaa accctgctga  27540

agtaggggtt ggcggaagcc aggagttcct gaatgcgaag ggtttgagct gaagggcgct  27600

tccaggatcc agaaggtcac tggagacctg tttttcaccc cctcagaggg caaaaccaaa  27660

agaaaaatgg attaggagag gggg                                        27684
```

<210> SEQ ID NO 5
<211> LENGTH: 3029
<212> TYPE: DNA
<213> ORGANISM: Homo Sapiens

<400> SEQUENCE: 5

```
acatttagga gaaacagcgg tgtctgcggc tcccaccctt cggggggccc gtgggggggg     60
cggtgtcagg ggcatggacg ccaccccca ggggtctctg ctgccggcta ctctcctctc    120
cacgtgctcc cctccaggac ccccgacgcc gcctaggcgc ccagcgacgc gcggcaggtg    180
gcagcagctc gggcccccgc cgcactccag gcgcccgcag cgctcgccct gacgcggccg    240
ccatggcgca ggagaacgcg gccttctcgc ccgggcagga ggagccgccg cggcgccgcg    300
gccgccagcg ctacgtggag aaggatggcc ggtgcaacgt gcagcagggc aacgtgcgcg    360
agacataccg ctacctgacg gacctgttca ccacgctggt ggacctgcag tggcgcctca    420
gcctgttgtt cttcgtcctg gcctacgcgc tcacctggct cttcttcggc gccatctggt    480
ggctgatcgc ctacggccgc ggcgacctgg agcacctgga ggacaccgcg tggacgccgt    540
gcgtcaacaa cctcaacggc ttcgtggccg ccttcctctt ctccatcgag accgagacca    600
ccatcggcta cgggcaccgc gtcatcaccg accagtgccc cgagggcatc gtgctgctgc    660
tgctgcaggc catcctgggc tccatggtga acgccttcat ggtgggctgc atgttcgtca    720
agatctcgca gcccaacaag cgcgcagcca cgctcgtctt ctcctcgcac gccgtggtgt    780
cgctgcgcga cgggcgcctc tgcctcatgt tccgcgtggg cgacttgcgc tcctcacaca    840
tagtggaggc ctccatccgc gccaagctca tccgctcgcg ccagacgctg gagggcgagt    900
tcatcccgct gcaccagacc gacctcagcg tgggcttcga cacgggagac gaccgcctct    960
tcctcgtctc gccgctggtt atcagccacg agatcgacgc cgccagcccc ttctgggagg   1020
cgtcgcgccg tgccctcgag agggacgact tcgagatcgt cgttatcctc gagggcatgg   1080
tggaagccac gggaatgaca tgccaagctc ggagctccta cctggtagac gaggtgctgt   1140
ggggccaccg cttcacgtca gtgctgactc tggaggacgg cttctacgaa gtggactatg   1200
ccagctttca cgagactttt gaggtgccca caccttcgtg cagtgctcga gagctggcag   1260
aggctgccgc ccgccttgat gcccatctct actggtccat ccccagccgg ctggatgaga   1320
aggtggagga ggaggggggcg ggggagggggg cgggtgggga agctggggct gacaaggagc   1380
agaatggctg cctgccaccc ccagagagtg agtccaaggt gtgaccagct tcctccagac   1440
ccctgtggca gaccgggggc cagacacaga tacatgggga actgcatatc ggaggtggtg   1500
gaggaggagg aggaggagga aggcaaagcc cctggaaatg tgctaaagtt ggaaagtccc   1560
cgtcccccag aacctcaagt ctagaaacca gtatggaagg gaggggtcct gatttcaggg   1620
aaatggaggg tggggccggg tgaaaatgcc agtctgtgtt tgaccttcac atttgttcat   1680
gagtggatgg atggacagaa tgatggactt ttgggggttg gatgggaaga tggtagcaga   1740
taaagacagc tgacagatac atagatggac cagtagacaa ctggtccact cagggctgcc   1800
actaacctgt agaacacccc tgtgcaaatt ttaaaaagga acccttttcc tccagacaga   1860
tacagcccca aaccagggtg catggcttgg ggagcagagt ataggatgga ttgcagtccc   1920
cagtcacctc ttctgccagc ctccccacat atggcacaac tgtctaatga cacggtaggc   1980
caagctgaag tgaaggagaa aggagccgga ccaagatggg cacatgagga gggtgccctc   2040
ctagctccac cctcaccagg atgaaggcgt gcaaggggct cagcaaggtg tgaatgacct   2100
tagtccgcaa gttcagggaa gcaggcagag cggggaggtg cctgagctgg ggcctggaga   2160
ggggcctggg aaaggaaaac cagggatagc tattttctta cagtggagtg agatcttaca   2220
ggtatcaggc acaggcagga agagagagag agaggttctg gggaggaagg gccaggagag   2280
agatctagaa agtgggttca ctagagctgg gaaacaggga gcccctagga aagcagtgtg   2340
```

-continued

```
tccttggggc acagtcattc acatcactga ttgggtgcca tgtggagtgg acattcaaaa   2400

acctggttcc tgtcctcaaa ataaggggca cctgggaaaa cagaggaatc tacctgtggt   2460

gactgaacga gggataattc aaactgacaa cctgtgcagt cccgtggagg gtaggggagt   2520

gtgggtgatc agaaggctgg ggccagtgta aggcataggg aatatgtaag tcaggagtta   2580

gaaatctcca gtgtgcgttg gaatcacctg gagggcttgg taaaacacag atttttgggc   2640

tccactccaa gggtttctga cccaagaggt ggggaccaaa accatgcatt cctaagaagt   2700

ccccaggtca tgctgctgtt gctggactga ggaccacact ttgagaacct gtgctctaag   2760

tgaatacttg gaagtcgttt caggacatgg ggcatagaaa ctgaggagta gctgagagga   2820

agatgaagag aagctgagaa gaagctgagg atcctcacag gagcagacag agaaatgtga   2880

agggtggggt tttatgtgtg ggaaagggac ccgaagccca ggctgaagag tttaactttg   2940

ggcccagaaa ctcaaccatc aatggaaaca gggcagtgac aagtggaggg ggtgtctgga   3000

agctgagcag gcccgacaga gagatgaag                                      3029
```

<210> SEQ ID NO 6
<211> LENGTH: 1182
<212> TYPE: DNA
<213> ORGANISM: Homo Sapiens

<400> SEQUENCE: 6

```
atggcgcagg agaacgcggc cttctcgccc gggcaggagg agccgccgcg gcgccgcggc     60

cgccagcgct acgtggagaa ggatggccgg tgcaacgtgc agcagggcaa cgtgcgcgag    120

acataccgct acctgacgga cctgttcacc acgctggtgg acctgcagtg gcgcctcagc    180

ctgttgttct tcgtcctggc ctacgcgctc acctggctct tcttcggcgc catctggtgg    240

ctgatcgcct acggccgcgg cgacctggag cacctggagg acaccgcgtg gacgccgtgc    300

gtcaacaacc tcaacggctt cgtggccgcc ttcctcttct ccatcgagac cgagaccacc    360

atcggctacg ggcaccgcgt catcaccgac cagtgccccg agggcatcgt gctgctgctg    420

ctgcaggcca tcctgggctc catggtgaac gccttcatgg tgggctgcat gttcgtcaag    480

atctcgcagc ccaacaagcg cgcagccacg ctcgtcttct cctcgcacgc cgtggtgtcg    540

ctgcgcgacg ggcgcctctg cctcatgttc cgcgtgggcg acttgcgctc ctcacacata    600

gtggaggcct ccatccgcgc caagctcatc cgctcgcgcc agacgctgga gggcgagttc    660

atcccgctgc accagaccga cctcagcgtg ggcttcgaca cgggagacga ccgcctcttc    720

ctcgtctcgc cgctggttat cagccacgag atcgacgccg ccagcccctt ctgggaggcg    780

tcgcgccgtg ccctcgagag ggacgacttc gagatcgtcg ttatcctcga gggcatggtg    840

gaagccacgg gaatgacatg ccaagctcgg agctcctacc tggtagacga ggtgctgtgg    900

ggccaccgct tcacgtcagt gctgactctg gaggacggct tctacgaagt ggactatgcc    960

agctttcacg agacttttga ggtgcccaca ccttcgtgca gtgctcgaga gctggcagag   1020

gctgccgccc gccttgatgc ccatctctac tggtccatcc ccagccggct ggatgagaag   1080

gtggaggagg agggggcggg ggagggggcg ggtggggaag ctggggctga caaggagcag   1140

aatggctgcc tgccaccccc agagagtgag tccaaggtgt ga                       1182
```

<210> SEQ ID NO 7
<211> LENGTH: 5
<212> TYPE: PRT
<213> ORGANISM: Unknown

-continued

```
<220> FEATURE:
<223> OTHER INFORMATION: Cytokine receptor extracellular motif found in
      many species
<220> FEATURE:
<221> NAME/KEY: VARIANT
<222> LOCATION: 3
<223> OTHER INFORMATION: Xaa = Any Amino Acid

<400> SEQUENCE: 7

Trp Ser Xaa Trp Ser
 1               5
```